United States Patent
Feinstein et al.

(10) Patent No.: US 10,781,449 B2
(45) Date of Patent: *Sep. 22, 2020

(54) DOUBLE-STRANDED OLIGONUCLEOTIDE MOLECULES TARGETING P53 AND METHODS OF USE THEREOF

(71) Applicant: QUARK PHARMACEUTICALS, INC., Fremont, CA (US)

(72) Inventors: Elena Feinstein, Rehovot (IL); Sharon Avkin-Nachum, Nes Zionna (IL); Hagar Kalinski, Rishon-le-Zion (IL); Igor Mett, Rehovot (IL)

(73) Assignee: QUARK PHARMACEUTICALS, INC., Fremont, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/942,587

(22) Filed: Apr. 2, 2018

(65) Prior Publication Data

US 2019/0040385 A1    Feb. 7, 2019

Related U.S. Application Data

(63) Continuation of application No. 14/421,845, filed as application No. PCT/US2013/059349 on Sep. 12, 2013, now Pat. No. 9,932,578.

(60) Provisional application No. 61/699,885, filed on Sep. 12, 2012.

(51) Int. Cl.
*C12N 15/11* (2006.01)
*C12N 15/113* (2010.01)

(52) U.S. Cl.
CPC ........ *C12N 15/113* (2013.01); *C12N 15/1135* (2013.01); *C12N 15/1136* (2013.01); *C12N 2310/14* (2013.01); *C12N 2310/317* (2013.01); *C12N 2310/319* (2013.01); *C12N 2310/321* (2013.01); *C12N 2310/3521* (2013.01); *C12N 2320/30* (2013.01)

(58) Field of Classification Search
None
See application file for complete search history.

(56) References Cited

U.S. PATENT DOCUMENTS

| 6,365,577 B1 | 4/2002 | Iversen |
| 2013/0035368 A1 | 2/2013 | Avkin-Nachum et al. |

FOREIGN PATENT DOCUMENTS

| WO | 2010/080452 | 7/2010 |

OTHER PUBLICATIONS

Vickers et al, Efficient Reduction of Target RNAs by Small Interfering RNA and RNase H-dependent Antisense Agents, 2003, The Journal of Biological Chemistry, vol. 278, 9: 7108-7118.

*Primary Examiner* — Ekaterina Poliakova-Georgantas
(74) *Attorney, Agent, or Firm* — JMB Davis Ben-David

(57) ABSTRACT

The present application relates to nucleic acid compounds, compositions comprising same and methods of use thereof for treatment of various diseases, disorders and conditions. The compounds are preferably chemically synthesized and modified double-stranded nucleic acid molecules which down regulate expression of a p53 gene.

11 Claims, No Drawings
Specification includes a Sequence Listing.

DOUBLE-STRANDED OLIGONUCLEOTIDE MOLECULES TARGETING P53 AND METHODS OF USE THEREOF

CROSS-REFERENCE TO RELATED APPLICATIONS

This is a Continuation of U.S. patent application Ser. No. 14/421,845, filed Feb. 16, 2015, which is the US national stage of International Patent Application No. PCT/US2013/059349, filed Sep. 12, 2013, which claimed the benefit of U.S. Provisional Application No. 61/699,885 filed Sep. 12, 2012. The foregoing patent applications are incorporated herein by reference in their entirety.

SEQUENCE LISTING

This application incorporates-by-reference nucleotide and/or amino acid sequences which are present in the file named "247-PCT1_ST25.txt", which is 29 Kbytes in size, and which was created on Sep. 3, 2013.

FIELD OF THE INVENTION

The present disclosure relates to nucleic acid molecules, pharmaceutical compositions comprising same and methods of use thereof for down-regulation of a p53 gene. The compounds and compositions disclosed herein are useful for treating a subject suffering from or at risk for the development of a disease or a disorder associated with a p53 gene expression. Examples of such diseases/disorders include, without being limited to, ischemia-reperfusion injury, a hearing impairment, a hearing disorder, a balance impairment, a hearing loss, chemotherapy-induced alopecia (hair loss), radiation therapy-induced alopecia, an acute renal failure, an acute kidney injury, a chronic kidney disease (CKD), a side effect associated with anti-cancer therapy, Delayed Graft Function (DGF) in a kidney transplant patient, a spinal cord injury, a brain injury, a seizure, a stroke, a neurodegenerative disorder, Parkinson's disease, Alzheimer's disease, a tumor, a burn, a wound, hyperthermia, hypoxia, ischemia, organ transplantation, myocardial infarction/heart attack, cardiotoxicity and acute liver failure.

BACKGROUND OF THE INVENTION siRNA and RNA Interference

RNA interference (RNAi) is a phenomenon involving double-stranded (ds) RNA-dependent gene specific post-transcriptional silencing.

U.S. patent application Ser. No. 13/508,493, US Patent Applications publication Nos. 20060069056, 20100029746, 20100222409, 20110142917, 20120184597, 20120141378 and U.S. Pat. Nos. 7,825,099, 7,842,674, 7,910,566, 8,148,342, all to the assignee of the present application, relate to double-stranded RNA compounds and compositions useful in down-regulating a p53 gene and to use of such compounds and compositions for treating a patient suffering from or at risk for the development of a disease or a disorder associated with p53 gene expression.

U.S. Pat. Nos. 6,982,277, 7,008,956, 7,012,087, assigned to The Board of Trustees of the University of Illinois, relate to a method of reversibly inhibiting p53 for a sufficient time to allow normal cells in a host to recover from a stress-inducing event affecting the cell, to a method of reducing hair loss associated with a cancer therapy comprising administering a therapeutically effective dose of a reversible p53 inhibitor to a mammal in need thereof in conjunction with the cancer therapy; and to a method of reducing cell death in a mammal attributable to a stress-inducing event in a central nervous system affecting the cell, said method comprising administering to the mammal a therapeutically effective amount of a temporary p53 inhibitor to reversibly inhibit p53 activity.

US Application Publication Nos 2010/0292301 and 2011/0112168, and PCT Patent Publication Nos. WO 2011/066475, WO 2011/084193, WO 2011/085056 and WO 2012/078536 to the assignee of the present invention and hereby incorporated by reference in their entirety, disclose nucleic acid sequences and modifications useful in generating dsRNA molecules.

US Application Publication Nos. 2011/0142917, 2011/0229557 and 2012/0141378 to the assignee of the present invention and hereby incorporated by reference in their entirety, disclose compositions and methods of use of double-stranded RNA compounds targeting a p53 gene.

Molecules, compositions, methods and kits useful in treating or attenuating a condition, a disease or a disorder associated with expression of a p53 gene and which exhibit at least one of increased bioavailability, improved biodistribution, increased serum circulation time, increased serum stability, decreased serum clearance, improved cellular uptake, reduced off target activity, reduced immunogenicity, improved endosomal release, improved specific delivery to target tissue or cell and increased knock down activity when compared to unmodified dsRNA counterparts are needed.

SUMMARY OF THE INVENTION

Nucleic acid molecules for down-regulating expression of p53 gene, compositions and kits comprising same and methods of use thereof are provided herein. The compositions, methods and kits may involve use of nucleic acid molecules (for example, short interfering nucleic acid (siNA), short interfering RNA (siRNA), double-stranded RNA (dsRNA), micro-RNA (miRNA) or short hairpin RNA (shRNA)) that bind a nucleotide sequence (such as an mRNA sequence) or portion thereof, encoding p53, for example, the mRNA coding sequence (SEQ ID NO:1-7) for human p53, encoding one or more proteins or protein subunits. In certain preferred embodiments, the molecules, compositions, methods and kits disclosed herein down-regulate or inhibit expression of the p53 gene. In various embodiments the nucleic acid molecule is selected from the group consisting of unmodified or chemically modified dsRNA compound such as a siRNA or shRNA that down-regulates the expression of a p53 gene.

In some embodiments the nucleic acid molecule is a synthetic, unmodified double stranded RNA (dsRNA) compound that down-regulates p53 expression.

In some preferred embodiments the nucleic acid molecule is a synthetic, chemically modified double-stranded RNA (dsRNA) compound that down-regulates p53 expression. In certain preferred embodiments, "p53" refers to human p53 gene. In certain preferred embodiments, "target gene" refers to human p53 gene.

The chemically modified nucleic acid molecules and compositions provided herein exhibit beneficial properties, including at least one of increased serum stability, improved cellular uptake, reduced off-target activity, reduced immunogenicity, improved endosomal release, improved specific delivery to target tissue or cell and increased knock down/down-regulation activity when compared to corresponding unmodified nucleic acid molecules.

Further disclosed herein are methods for treating or preventing the incidence or severity of a disorder, disease, injury or condition in a subject in need thereof wherein the disease or condition and/or a symptom or pathology associated therewith is associated with expression of the p53 gene. In some embodiments, such as a disorder, disease, injury, condition or pathology is selected from a group comprising a disorder, disease, injury, condition or pathology of the inner ear; a disorder, disease, injury, condition or pathology of the kidney; a disorder, disease, injury, condition or pathology of the central nervous system (CNS); a disorder, disease, injury, condition or pathology of the heart, a disorder, disease, injury, condition or pathology of the liver; a disorder, disease, injury, condition or pathology of the heart; a disorder, disease, injury, condition or pathology affecting an organ transplant patient; a disorder, disease, injury, condition or pathology experienced by a patient undergoing anti-cancer treatment. In some embodiments, such as a disorder, disease, injury, condition or pathology in selected from a group comprising ischemia-reperfusion injury, a hearing impairment, a hearing disorder, a balance impairment, a hearing loss, chemotherapy-induced alopecia, radiation therapy-induced alopecia, an acute renal failure, an acute kidney injury, a chronic kidney disease (CKD), a side effect associated with anti-cancer therapy, Delayed Graft Function (DGF) in a kidney transplant patient, a spinal cord injury, a brain injury, a seizure, a stroke, Parkinson's disease, Alzheimer's disease, a tumor, a burn, a wound, hyperthermia, hypoxia, ischemia, organ transplantation, myocardial infarction/heart attack, cardiotoxicity and acute liver failure.

In particular embodiments, chemically modified dsRNA compounds that target p53, compositions and kits comprising same and methods of use thereof in the treatment of a condition or pathology involving apoptosis, that is apoptotic (programmed) death of cells, are provided herein. Other conditions to be treated include any condition in which p53 expression is detrimental, and are treated with the compounds and compositions provided herein.

In one aspect, provided herein are oligonucleotide sequences (SEQ ID NO: 8-33) useful for generation of nucleic acid compounds that target and down-regulate the p53 gene.

In another aspect, provided are nucleic acid compounds that target and down-regulate the p53 gene, or pharmaceutically acceptable salts of such compounds. In some preferred embodiments the nucleic acid molecules disclosed herein have a double-stranded structure. In some embodiments the nucleic acid compounds have a double-stranded structure and each of the strands comprises an oligonucleotide sequence selected form the sequences set forth in Table 1 below (SEQ ID NO: 8-33). In some embodiments of nucleic acid compounds having a double-stranded structure, the oligonucleotide sequence of one of the strands is selected from one of SEQ ID NOS: 8-20 and the oligonucleotide sequence of the other strand is selected from one of SEQ ID NOS: 21-33.

In some embodiments, provided are nucleic acid molecules, or pharmaceutically acceptable salts of such molecules, having a double-stranded structure in which (a) the nucleic acid molecule is a duplex which includes a sense strand and a complementary antisense strand; (b) each strand of the nucleic acid molecule is 19 nucleotides in length; (c) a 19 nucleotide sequence of the antisense strand is complementary to a consecutive sequence of a mRNA encoding mammalian p53 (e.g., SEQ ID NO: 1-7) or portion thereof; and (d) the sense strand and antisense strand are selected from the oligonucleotide sequences set forth in Table 1 below (SEQ ID NO: 8-33).

TABLE 1

Selected sense strand and antisense strand oligonucleotide sequences for nucleic acid compounds targeting p53

| SEQ ID NO | Sense strand (5'>3') | SEQ ID NO | Antisense strand (5'>3') |
|---|---|---|---|
| 8 | 5' CAGACCUAUGGAAACUACU 3' | 21 | 5' AGUAGUUUCCAUAGGUCUG 3' |
| 9 | 5' GGAUGUUUGGGAGAUGUAA 3' | 22 | 5' UUACAUCUCCCAAACAUCC 3' |
| 10 | 5' GACUCAGACUGACAUUCUA 3' | 23 | 5' UAGAAUGUCAGUCUGAGUC 3' |
| 11 | 5' GGGUUGGUAGUUUCUACAA 3' | 24 | 5' UUGUAGAAACUACCAACCC 3' |
| 12 | 5' GGGAUGUUUGGGAGAUGUA 3' | 25 | 5' UACAUCUCCCAAACAUCCC 3' |
| 13 | 5' GGAUCCACCAAGACUUGUA 3' | 26 | 5' UACAAGUCUUGGUGGAUCC 3' |
| 14 | 5' GAGGGAUGUUUGGGAGAUA 3' | 27 | 5' UAUCUCCCAAACAUCCCUC 3' |
| 15 | 5' GGGCCUGACUCAGACUGAA 3' | 28 | 5' UUCAGUCUGAGUCAGGCCC 3' |
| 16 | 5' GACUCAGACUGACAUUCUU 3' | 29 | 5' AAGAAUGUCAGUCUGAGUC 3' |
| 17 | 5' GCAUUUGCACCUACCUCAA 3' | 30 | 5' UUGAGGUAGGUGCAAAUGC 3' |
| 18 | 5' GGAUGUUUGGGAGAUGUAU 3' | 31 | 5' AUACAUCUCCCAAACAUCC 3' |
| 19 | 5' GGGCCUGACUCAGACUGAU 3' | 32 | 5' AUCAGUCUGAGUCAGGCCC 3' |
| 20 | 5' CAGACCUAUGGAAACUACA 3' | 33 | 5' UGUAGUUUCCAUAGGUCUG 3' |
| 34 | 5' CCGAGUGGAAGGAAAUUUG 3' | 35 | 5' CAAAUUUCCUUCCACUCGG 3' |
| 36 | 5' GAGAAUAUUUCACCCUUCA 3' | 37 | 5' UGAAGGGUGAAAUAUUCUC 3' |

All positions given in Table 1 are 5'>3' on the sense strand and on the antisense strand.

In another embodiment, provided are nucleic acid compounds (e.g., dsRNA molecules), or pharmaceutically acceptable salts of such compounds, in which (a) the nucleic acid molecule is a duplex which includes a sense strand and a complementary antisense strand; (b) each strand of the nucleic acid molecule is 19 nucleotides in length; (c) a 19 nucleotide sequence of the antisense strand is complementary to a consecutive sequence of a mRNA encoding mammalian p53 (e.g., SEQ ID NO: 1-7) or portion thereof; and (d) the sense strand and antisense strand comprise sequence pairs set forth in Table 2 below.

According to one embodiment provided are modified nucleic acid molecules having a structure (A), set forth below:

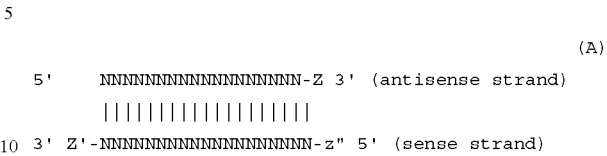

TABLE 2

Selected pairs of sense and antisense strands for generating double-stranded nucleic acid compounds targeting p53

| Pair Name | SEQ ID NO | Sense strand (5'>3') | SEQ ID NO | Antisense strand (5'>3') |
|---|---|---|---|---|
| p53_13 | 8 | 5' CAGACCUAUGGAAACUACU 3' | 21 | 5' AGUAGUUUCCAUAGGUCUG 3' |
| p53_34 | 9 | 5' GGAUGUUUGGGAGAUGUAA 3' | 22 | 5' UUACAUCUCCCAAACAUCC 3' |
|  | 9 | 5' GGAUGUUUGGGAGAUGUAA 3' | 31 | 5' AUACAUCUCCCAAACAUCC 3' |
| p53_35 | 10 | 5' GACUCAGACUGACAUUCUA 3' | 23 | 5' UAGAAUGUCAGUCUGAGUC 3' |
| p53_36 | 11 | 5' GGGUUGGUAGUUUCUACAA 3' | 24 | 5' UUGUAGAAACUACCAACCC 3' |
| p53_37 | 12 | 5' GGGAUGUUUGGGAGAUGUA 3' | 25 | 5' UACAUCUCCCAAACAUCCC 3' |
| p53_38 | 13 | 5' GGAUCCACCAAGACUUGUA 3' | 26 | 5' UACAAGUCUUGGUGGAUCC 3' |
| p53_39 | 14 | 5' GAGGGAUGUUUGGGAGAUA 3' | 27 | 5' UAUCUCCCAAACAUCCCUC 3' |
| p53_40 | 15 | 5' GGGCCUGACUCAGACUGAA 3' | 28 | 5' UUCAGUCUGAGUCAGGCCC 3' |
| p53_41 | 16 | 5' GACUCAGACUGACAUUCUU 3' | 29 | 5' AAGAAUGUCAGUCUGAGUC 3' |
| p53_42 | 17 | 5' GCAUUUGCACCUACCUCAA 3' | 30 | 5' UUGAGGUAGGUGCAAAUGC 3' |
| p53_43 | 18 | 5' GGAUGUUUGGGAGAUGUAU 3' | 31 | 5' AUACAUCUCCCAAACAUCC 3' |
|  | 18 | 5' GGAUGUUUGGGAGAUGUAU 3' | 22 | 5' UUACAUCUCCCAAACAUCC 3' |
| p53_44 | 19 | 5' GGGCCUGACUCAGACUGAU 3' | 32 | 5' AUCAGUCUGAGUCAGGCCC 3' |
|  | 19 | 5' GGGCCUGACUCAGACUGAU 3' | 28 | 5' UUCAGUCUGAGUCAGGCCC 3' |
| p53_45 | 20 | 5' CAGACCUAUGGAAACUACA 3' | 33 | 5' UGUAGUUUCCAUAGGUCUG 3' |
|  | 20 | 5' CAGACCUAUGGAAACUACA 3' | 21 | 5' AGUAGUUUCCAUAGGUCUG 3' |

All positions given in Table 2 are 5'>3' on the sense strand and on the antisense strand.

In preferred embodiments of the double-stranded nucleic acid molecule disclosed herein, the sense strand and the antisense strand are selected from the group consisting of a sense strand SEQ ID NO: 16 and an antisense strand SEQ ID NO: 29, a sense strand SEQ ID NO: 19 and an antisense strand SEQ ID NO: 32 and a sense strand SEQ ID NO: 19 and an antisense strand SEQ ID NO: 28.

The nucleic acid molecules provided herein are preferably double-stranded nucleic acid molecules that possess modifications, which may increase activity, increase stability, and/or minimize toxicity when compared to the corresponding unmodified dsRNA compound. These molecules, when admixed with a pharmaceutical vehicle that effects delivery of the nucleic acid to the target organ, provide effective, safe and patient compliant therapeutic compounds useful in treating a variety of disorders associated with the p53 gene. The nucleic acid compounds are designed to down-regulate p53 gene expression and attenuate p53 gene function. In various embodiment the p53 gene is human p53 gene transcribed into any one of the mRNA polynucleotides set forth in SE ID NOS:1-7.

wherein each N is independently any one of A, C, G, U and is independently an unmodified ribonucleotide, a modified ribonucleotide, or an unconventional moiety;

wherein each "|" represents base pairing between each N of the antisense and the corresponding N of the sense strand;

wherein each of Z and Z' is independently present or absent, but if present is independently 1-5 consecutive nucleotides, 1-5 consecutive nucleotide analogues or 1-5 consecutive non-nucleotide moieties or a combination thereof, or a conjugate moiety, covalently attached at the 3' terminus of the strand in which it is present;

wherein z" may be present or absent, but if present is a capping moiety, or a conjugate moiety covalently attached at the 5' terminus of the sense strand; and wherein the sequence of the sense strand is complementary to the sequence of the antisense strand; with the proviso that not each N and N' is an unconventional moiety.

According to one embodiment provided are modified nucleic acid molecules having a structure (A1), set forth below:

5' (N)x-Z 3' (antisense strand)

3' Z'-(N')y-z" 5' (sense strand)  (A1)

wherein each N and N' is independently a ribonucleotide which may be an unmodified ribonucleotide, a modified ribonucleotide, or an unconventional moiety;
wherein each of (N)x and (N')y is an oligonucleotide in which each consecutive N or N' is joined to the adjacent N or N' by a covalent bond;
wherein each of Z and Z' is independently present or absent, but if present independently comprises 1-5 consecutive nucleotides, 1-5 consecutive nucleotide analogues or 1-5 consecutive non-nucleotide moieties or a combination thereof, or a conjugate moiety, covalently attached at the 3' terminus of the strand in which it is present;
wherein z" may be present or absent, but if present is a capping moiety, or a conjugate moiety covalently attached at the 5' terminus of (N')y;
wherein each of x and y is independently an integer between 18 and 40;
wherein the sequence of (N')y is complementary to the sequence of (N)x; and
wherein (N)x comprises an antisense sequence and (N')y comprises a sense sequence; with the proviso that not each N and N' is an unconventional moiety.

In various embodiments of structure (A1) x=y. In preferred embodiments of structure (A1) x=y=19.

According to one embodiment provided are modified nucleic acid molecules having a structure (A2), set forth below:

5' N1-(N)x-Z 3' (antisense strand)

3' Z'-N2-(N')y-z" 5' (sense strand)  (A2)

wherein each N1, N2, N and N' is independently an unmodified ribonucleotide, a modified ribonucleotide, or an unconventional moiety;
wherein each of (N)x and (N')y is an oligonucleotide in which each consecutive N or N' is joined to the adjacent N or N' by a covalent bond;
wherein each of x and y is independently an integer between 17 and 39;
wherein N2 is covalently bound to (N')y;
wherein N1 is covalently bound to (N)x and is mismatched to the target RNA (SEQ ID NO:1-7) or is a complementary DNA moiety complementary to the target RNA;
wherein N1 is a moiety selected from the group consisting of a natural uridine, a modified: uridine, deoxyribouridine, ribothymidine, deoxyribothymidine, natural adenosine, modified adenosine, deoxyadenosine, adenosine pyrazolotriazine nucleic acid analogue, deoxyadenosine pyrazolotriazine nucleic acid analogue, an abasic ribose moiety and an abasic deoxyribose moiety;
wherein z" may be present or absent, but if present is a capping moiety, a vitamin or a drug moiety covalently attached at the 5' terminus of N2-(N')y;
wherein each of Z and Z' is independently present or absent, but if present is independently 1-5 consecutive nucleotides, 1-5 consecutive nucleotide analogues, 1-5 consecutive non-nucleotide moieties or a combination thereof, or a conjugate moiety, covalently attached at the 3' terminus of the strand in which it is present;
wherein the sequence of (N')y is complementary to the sequence of (N)x;
wherein at least a portion of the sequence of (N)x is complementary to a consecutive sequence in the target RNA; and
wherein the sequence of N1-(N)x comprises an antisense sequence and N2-(N')y comprises a sense sequence; with the proviso that not each N and N' is an unconventional moiety.

In various embodiments of structure (A2) x=y. In preferred embodiments of structure (A2) x=y=18.

In preferred embodiments of structures (A), (A1) and (A2) the sense strand and the antisense strand are selected from the group consisting of a sense strand SEQ ID NO: 16 and an antisense strand SEQ ID NO: 29, a sense strand SEQ ID NO: 19 and an antisense strand SEQ ID NO: 32 and a sense strand SEQ ID NO: 19 and an antisense strand SEQ ID NO: 28.

In various embodiments of structures (A), (A1) and (A2), the modified ribonucleotide comprises a modification at the 2' position of the sugar moiety. In some preferred embodiments the modified ribonucleotide is a 2'-O-methyl sugar modified ribonucleotide.

In various embodiments of structures (A), (A1) and (A2), the unconventional moiety is selected from the group consisting of a mirror nucleotide, an unmodified deoxyribonucleotide, a modified deoxyribonucleotide, a threose nucleic acid (TNA), a nucleotide analogue and a ribonucleotide joined to an adjacent ribonucleotide by a 2'-5' internucleotide phosphate bond (5'>3'). In some preferred embodiments the nucleotide analogue is a pyrazolotriazine (PT) nucleotide analogue. In some preferred embodiments the unconventional moiety a ribonucleotide joined to an adjacent ribonucleotide by a 2'-5' internucleotide phosphate bond (5'>3').

In various embodiments of structures (A), (A1) and (A2) both Z or Z' are absent. In some embodiments at least one of Z or Z' is present. In some embodiments both of Z and Z' are present. In some embodiments both of Z and Z' are present and are 1-5 consecutive nucleotides. In some embodiments both of Z and Z' are present and are 2 consecutive nucleotides. In some embodiments both of Z and Z' are present, both Z and Z' are 2 consecutive nucleotides, each nucleotide is a dT, and each of Z and Z' comprises two consecutive nucleotides (dTdT). In some embodiments both of Z and Z' are present and each of Z and Z' is 1-5 consecutive non-nucleotide moieties. In some embodiments both of Z and Z' are present and each of Z and Z' is 1-2 consecutive non-nucleotide moieties.). In some preferred embodiments each non-nucleotide moiety is a 1,3-Propanediol, mono(dihydrogen phosphate) (C3) [CAS RN: 13507-42-1]. In some preferred embodiments both of Z and Z' are present, Z is one C3 non-nucleotide moiety (C3) and Z' is two consecutive C3 non-nucleotide moieties (C3-C3).

In some embodiments of structures (A), (A1) and (A2) z" is absent. In some embodiments of structures (A), (A1) and (A2) z" is present. In various embodiments of structures (A), (A1) and (A2) z" is present and is selected from the group consisting of an abasic ribose moiety, an abasic deoxyribose moiety, an inverted abasic ribose moiety, an inverted deoxyribose moiety, an inverted deoxyabasic moiety (idAb), amino-C6 moiety (AM-c6), C6-amino-Pi, a non-nucleotide moiety, a mirror nucleotide, a 5,6,7,8-tetrahydro-2-naphthalene butyric phosphodiester (THNB), a vitamin and a drug moiety. In some embodiment z" is present and is a 1,3-Propanediol, mono(dihydrogen phosphate) (C3) non-nucleotide moiety.

In some embodiments of structures (A), (A1) and (A2) the nucleotide at the 3' terminus and at the 5' terminus in each of the antisense strand and the sense strand is phosphorylated. In some embodiments the nucleotide at the 3' terminus and at the 5' terminus in each of the antisense strand and the sense strand is non-phosphorylated. In some embodiments in each of the antisense strand and the sense strand the ribonucleotide at the 3' terminus is phosphorylated and the ribonucleotide at the 5' terminus is non-phosphorylated. In some embodiments the sense strand is either phosphorylated or non-phosphorylated at both the 3' terminus and the 5' terminus. In some embodiments the antisense strand is either phosphorylated or non-phosphorylated at both the 3' terminus and the 5' terminus.

According to one embodiment provided is a modified nucleic acid compound (1) having a sense strand and an antisense strand set forth below:

```
5' cap-GACUCAGACUGACAuucuu-C3-pi 3'
(sense strand; SEQ ID NO: 16)

5' AAGAAUgUCAGUCUGAGUC-C3-C3 3'
(antisense strand; SEQ ID NO: 29)
``` wherein each of A, U, G and C is an unmodified ribonucleotide;
wherein each of U, G and C is a 2'-O-methyl sugar modified ribonucleotide;
wherein each of u, c and g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or a pharmaceutically acceptable salt of such compound.

According to one embodiment of compound (1), the 5' cap covalently attached at the 5' terminus of the sense strand is 1,3-propanediol, mono(dihydrogen phosphate) (C3), the ribonucleotide at the 5' terminus of the antisense strand is phosphorylated (phos) and the overhang at the 3' terminus of the antisense strand is phosphorylated (—C3-C3-pi).

According to one embodiment provided is a modified nucleic acid compound (2) having a sense strand and an antisense strand set forth below:

```
5' cap-GACUCAGACUGACAUUCUU-C3-pi 3'
(sense strand; SEQ ID NO: 16)

5' AAGAAUgUCAGUCUGAGUC-C3-C3 3'
(antisense strand; SEQ ID NO: 29)
``` wherein each of A, U, G and C is an unmodified ribonucleotide;
wherein each of U, G and C is a 2'-O-methyl sugar modified ribonucleotide;
wherein g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or a pharmaceutically acceptable salt of such compound.

According to one embodiment provided is a modified nucleic acid compound (3) having a sense strand and an antisense strand set forth below:

```
5' cap-GACUCAGACUGACAUUCUU-C3-pi 3'
(sense strand; SEQ ID NO: 16)

5' AAGAAUgUCAGUCUGAGUC-C3-C3 3'
(antisense strand; SEQ ID NO: 29)
``` wherein each of A, U, G and C is an unmodified ribonucleotide;
wherein each of U, G and C is a 2'-O-methyl sugar modified ribonucleotide;
wherein g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound (4) having a sense strand and an antisense strand set forth below:

```
5' cap-GACUCAGACUGACAUUCUU-C3-pi 3'
(sense strand; SEQ ID NO: 16)

5' AAGAAuGUCAGUCUGAGUC-C3-C3 3'
(antisense strand; SEQ ID NO: 29)
``` wherein each of A, U, G and C is an unmodified ribonucleotide;
wherein each of U, G and C is a 2'-O-methyl sugar modified ribonucleotide;
wherein u is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;

wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or a pharmaceutically acceptable salt of such compound.

According to one embodiment provided is a modified nucleic acid compound (5) having a sense strand and an antisense strand set forth below:

```
5' GACUCAGACUGACAUUCUA-dTdT 3'
(sense strand; SEQ ID NO: 16)

5' AAGAAUGUCAGUCUGAGUC-dTdT 3'
(antisense strand; SEQ ID NO: 29)
``` wherein each of A, U, G and C is an unmodified ribonucleotide;
wherein in the antisense strand and in the sense strand, each consecutive ribonucleotide is joined to the next ribonucleotide by a phosphodiester bond;
wherein each of the sense strand and the antisense strand comprises a two nucleotide thymidine-thymidine (dTdT) overhang covalently attached at the 3' terminus of the strand; and
wherein the 3' terminus of the sense strand and of the antisense strand is non-phosphorylated; or a pharmaceutically acceptable salt of such compound.

According to one embodiment provided is a modified nucleic acid compound (6) having a sense strand and an antisense strand set forth below:

```
5' C3-GACUCAGACUGACAUUCUU-C3-pi 3'
(sense strand; SEQ ID NO: 16)

5' phos-AAGAAUgUCAGUCUGAGUC-C3-C3-pi 3'
(antisense strand; SEQ ID NO: 29)
``` wherein each of A, U, G and C is an unmodified ribonucleotide;
wherein each of U, G and C is a 2'-O-methyl sugar modified ribonucleotide;
wherein g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand and wherein the overhang is phosphorylated (C3-pi);
wherein the sense strand comprises a C3 5' cap covalently attached at the 5' terminus of the strand;
wherein the antisense strand comprises a phosphorylated C3-C3 non-nucleotide overhang (—C3-C3-pi) covalently attached at the 3' terminus of the strand; and
wherein in the antisense strand the ribonucleotide at the 5' terminus is phosphorylated (phos); or a pharmaceutically acceptable salt of such compound.

According to one embodiment provided is a modified nucleic acid compound (7) having a sense strand and an antisense strand set forth below:

```
5' C3-GACUCAGACUGACAuucuu-C3-pi 3'
(sense strand; SEQ ID NO: 16)

5' phos-AAGAAUgUCAGUCUGAGUC-C3-C3-pi 3'
(antisense strand; SEQ ID NO: 29)
``` wherein each of A, U, G and C is an unmodified ribonucleotide;
wherein each of C is a 2'-O-methyl sugar modified ribonucleotide;
wherein each of u, c and g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand and wherein the overhang is phosphorylated (C3-pi);
wherein the sense strand comprises a C3 5' cap covalently attached at the 5' terminus of the strand;
wherein the antisense strand comprises a phosphorylated C3-C3 non-nucleotide overhang (—C3-C3-pi) covalently attached at the 3' terminus of the strand; and
wherein in the antisense strand the ribonucleotide at the 5' terminus is phosphorylated (phos); or
a pharmaceutically acceptable salt of such compound.

According to one embodiment provided is a modified nucleic acid compound (8) having a sense strand and an antisense strand set forth below:

```
5' C3-GACUCAGACUGACAUUCUU-C3-pi 3'
(sense strand; SEQ ID NO: 16)

5' phos-AAGAAUgUCAGUCUGAGUC-C3-C3-pi 3'
(antisense strand; SEQ ID NO: 29)
``` wherein each of A, U, G and C is an unmodified ribonucleotide;
wherein each of U and C is a 2'-O-methyl sugar modified ribonucleotide;
wherein g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand and wherein the overhang is phosphorylated (C3-pi);
wherein the sense strand comprises a C3 5' cap covalently attached at the 5' terminus of the strand;
wherein the antisense strand comprises a phosphorylated C3-C3 non-nucleotide overhang (—C3-C3-pi) covalently attached at the 3' terminus of the strand; and
wherein in the antisense strand the ribonucleotide at the 5' terminus is phosphorylated (phos); or
a pharmaceutically acceptable salt of such compound.

According to one embodiment provided is a modified nucleic acid compound (9) having a sense strand and an antisense strand set forth below:

```
5' cap-GGGCCUGACUCAGACUGAU-C3-pi 3'
(sense strand; SEQ ID NO: 19)
```

-continued
```
5' AUCAGUcUGAGUCAGGCCC-C3-C3 3'
(antisense strand; SEQ ID NO: 32)
``` wherein each of A, U, G and C is an unmodified ribonucleotide;

wherein each of U and C is a 2'-O-methyl sugar modified ribonucleotide;

wherein c is a ribonucleotide joined to an adjacent ribonucleotide (5'>3') by a 2'-5' internucleotide phosphate bond;

wherein in the antisense strand and in the sense strand, each consecutive ribonucleotide is joined to the next ribonucleotide by a phosphodiester bond;

wherein the sense strand comprises a 1,3-propanediol, mono (dihydrogen phosphate) (C3) non-nucleotide overhang covalently attached at the 3' terminus of the strand;

wherein the sense strand comprises a 5' cap covalently attached at the 5' terminus of the strand;

wherein the antisense strand comprises a C3-C3 non-nucleotide overhang covalently attached at the 3' terminus of the strand; and wherein the 3' terminus of the sense strand is phosphorylated (pi); or a pharmaceutically acceptable salt of such compound.

According to one embodiment of a modified nucleic acid compound (9) the 5' cap covalently attached at the 5' terminus of the sense strand is 1,3-propanediol, mono(dihydrogen phosphate) (C3); the ribonucleotide at the 5' terminus of the antisense strand is phosphorylated (phos) and the overhang at the 3' terminus of the antisense strand is phosphorylated (—C3-C3-pi)

According to one embodiment provided is a modified nucleic acid compound (10) having a sense strand and an antisense strand set forth below:

```
5' cap-GGGCCUGACUCAGAcugau-C3-pi 3'
(sense strand; SEQ ID NO: 19)

5' AUCAGuCUGAGUCAGGCCC-C3-C3 3'
(antisense strand; SEQ ID NO: 32)
``` wherein each of A, U, G and C is an unmodified ribonucleotide;

wherein each of U and C is a 2'-O-methyl sugar modified ribonucleotide;

wherein each of a, a, c: and g is a ribonucleotide joined to an adjacent ribonucleotide (5'>3') by a 2'-5' internucleotide phosphate bond;

wherein in the antisense strand and in the sense strand, each consecutive ribonucleotide is joined to the next ribonucleotide by a phosphodiester bond;

wherein the sense strand comprises a 1,3-propanediol, mono (dihydrogen phosphate) (C3) non-nucleotide overhang covalently attached at the 3' terminus of the strand;

wherein the sense strand comprises a 5' cap covalently attached at the 5' terminus of the strand;

wherein the antisense strand comprises a C3-C3 non-nucleotide overhang covalently attached at the 3' terminus of the strand; and wherein the 3' terminus of the sense strand is phosphorylated (pi); or a pharmaceutically acceptable salt of such compound.

According to one embodiment provided is a modified nucleic acid compound (11) having a sense strand and an antisense strand set forth below:

```
5' cap-GGGCCUGACUCAGACUGAU-C3-pi 3'
(sense strand; SEQ ID NO: 19)

5' AUCAGuCUGAGUCAGGCCC-C3-C3 3'
(antisense strand; SEQ ID NO: 32)
``` wherein each of A, U, G and C is an unmodified ribonucleotide;

wherein each of U and C is a 2'-O-methyl sugar modified ribonucleotide;

wherein u is a ribonucleotide joined to an adjacent ribonucleotide (5'>3') by a 2'-5' internucleotide phosphate bond;

wherein in the antisense strand and in the sense strand, each consecutive ribonucleotide is joined to the next ribonucleotide by a phosphodiester bond;

wherein the sense strand comprises a 1,3-propanediol, mono (dihydrogen phosphate) (C3) non-nucleotide overhang covalently attached at the 3' terminus of the strand;

wherein the sense strand comprises a 5' cap covalently attached at the 5' terminus of the strand;

wherein the antisense strand comprises a C3-C3 non-nucleotide overhang covalently attached at the 3' terminus of the strand; and wherein the 3' terminus of the sense strand is phosphorylated (pi); or a pharmaceutically acceptable salt of such compound.

According to one embodiment provided is a modified nucleic acid compound (12) having a sense strand and an antisense strand set forth below:

```
5' cap-GGGCCUGACUCAGACUGAU-C3-pi 3'
(sense strand; SEQ ID NO: 19)

5' AUCAGUcUGAGUCAGGCCC-C3-C3 3'
(antisense strand; SEQ ID NO: 32)
``` wherein each of A, U, G and C is an unmodified ribonucleotide;

wherein each of U and C is a 2'-O-methyl sugar modified ribonucleotide;

wherein c is a ribonucleotide joined to an adjacent ribonucleotide (5'>3') by a 2'-5' internucleotide phosphate bond;

wherein in the antisense strand and in the sense strand, each consecutive ribonucleotide is joined to the next ribonucleotide by a phosphodiester bond;

wherein the sense strand comprises a 1,3-propanediol, mono (dihydrogen phosphate) (C3) non-nucleotide overhang covalently attached at the 3' terminus of the strand;

wherein the sense strand comprises a 5' cap covalently attached at the 5' terminus of the strand;

wherein the antisense strand comprises a C3-C3 non-nucleotide overhang covalently attached at the 3' terminus of the strand; and wherein the 3' terminus of the sense strand is phosphorylated (pi); or a pharmaceutically acceptable salt of such compound.

According to one embodiment provided is a modified nucleic acid compound (13) having a sense strand and an antisense strand set forth below:

```
5' C3-GGGCCUGACUCAGAcugau-C3-pi 3'
(sense strand; SEQ ID NO: 19)

5' phos-AUCAGUcUGAGUCAGGCCC-C3-C3-pi 3'
(antisense strand; SEQ ID NO: 32)
``` wherein each of A, U, G and C is an unmodified ribonucleotide;

wherein each of U and C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand and wherein the overhang is phosphorylated (C3-pi);
wherein the sense strand comprises a C3 5' cap covalently attached at the 5' terminus of the strand;
wherein the antisense strand comprises a phosphorylated C3-C3 non-nucleotide overhang (—C3-C3-pi) covalently attached at the 3' terminus of the strand; and
wherein in the antisense strand the ribonucleotide at the 5' terminus is phosphorylated (phos); or
a pharmaceutically acceptable salt of such compound.

According to one embodiment provided is a modified nucleic acid compound (14) having a sense strand and an antisense strand set forth below:

```
5' C3-GGGCCUGACUCAGAcugau-C3-pi 3'
(sense strand; SEQ ID NO: 19)

5' phos-AUCAGUcUGAGUCAGGCCC-C3-C3-pi 3'
(antisense strand; SEQ ID NO: 32)
``` wherein each of A, U, G and C is an unmodified ribonucleotide;
wherein C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand and wherein the overhang is phosphorylated (C3-pi);
wherein the sense strand comprises a C3 5' cap covalently attached at the 5' terminus of the strand;
wherein the antisense strand comprises a phosphorylated C3-C3 non-nucleotide overhang (—C3-C3-pi) covalently attached at the 3' terminus of the strand; and
wherein in the antisense strand the ribonucleotide at the 5' terminus is phosphorylated (phos); or
a pharmaceutically acceptable salt of such compound.

According to one embodiment provided is a modified nucleic acid compound (15) having a sense strand and an antisense strand set forth below:

```
5' C3-GGGCCUGACUCAGACUGAU-C3-pi 3'
(sense strand; SEQ ID NO: 19)

5' phos-AUCAGUcUGAGUCAGGCCC-C3-C3-pi 3'
(antisense strand; SEQ ID NO: 32)
``` wherein each of A, U, G and C is an unmodified ribonucleotide;
wherein each of U and C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand and wherein the overhang is phosphorylated (C3-pi);
wherein the sense strand comprises a C3 5' cap covalently attached at the 5' terminus of the strand;
wherein the antisense strand comprises a phosphorylated C3-C3 non-nucleotide overhang (—C3-C3-pi) covalently attached at the 3' terminus of the strand; and
wherein in the antisense strand the ribonucleotide at the 5' terminus is phosphorylated (phos); or
a pharmaceutically acceptable salt of such compound.

According to one embodiment provided is a modified nucleic acid compound (16) having a sense strand and an antisense strand set forth below:

```
5' cap-GGGCCUGACUCAGACUGAU-C3-pi 3'
(sense strand; SEQ ID NO: 19)

5' UUCAGuCUGAGUCAGGCCC-C3-C3 3'
(antisense strand; SEQ ID NO: 28)
``` wherein each of A, U, G and C is an unmodified ribonucleotide;
wherein each of U and C is a 2'-O-methyl sugar modified ribonucleotide;
wherein u is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to various embodiments of modified nucleic acid compound (1), (2), (3), (4), (9), (10), (11), (12) and (16) the C3-C3 non-nucleotide overhang covalently attached at the 3' terminus of the antisense strand is phosphorylated (—C3-C3-pi).

According to various embodiments of modified nucleic acid compound (1), (2), (3), (4), (5), (6), (7), (8), (9), (10), (11), (12), (13), (14), (15), (16) and (17) the 5' cap is selected from the group consisting of an abasic ribose moiety, an abasic deoxyribose moiety, an inverted deoxyribose moiety, an inverted deoxyabasic moiety (idAb), amino-C6 moiety (AM-c6), C6-amino-pi, a non-nucleotide moiety, a mirror nucleotide, a 5,6,7,8-tetrahydro-2-naphthalene butyric phosphodiester (THNB) and a conjugate moiety. In various embodiments of modified nucleic acid compound (1), (2), (3), (4), (5), (6), (7), (8), (9), (10), (11), (12), (13), (14), (15), (16) and (17) the 5' cap is a non-nucleotide moiety. In some embodiments of modified nucleic acid compound (1), (2), (3), (4), (5), (6), (7), (8), (9), (10), (11), (12), (13), (14), (15), (16) and (17) the 5' cap non-nucleotide moiety is a 1,3-Propanediol, mono(dihydrogen phosphate) (C3).

According to various embodiments of modified nucleic acid compound (1), (2), (3), (4), (5), (6), (7), (8), (9), (10), (11), (12), (13), (14), (15), (16) and (17) the ribonucleotide at the 5' terminus in the antisense strand is phosphorylated (phos).

According to various embodiments of modified nucleic acid compound (1), (2), (3), (4), (5), (6), (7), (8), (9), (10), (11), (12), (13), (14), (15), (16) and (17) the ribonucleotide at the 5' terminus in the antisense strand is non-phosphorylated ($).

In another aspect, provided are pharmaceutical compositions that include a nucleic acid molecule (e.g., an siNA molecule) as described herein, or a pharmaceutically acceptable salt of such molecule, in a pharmaceutically acceptable carrier. In certain embodiments, the pharmaceutical formulation includes, or involves, a delivery system suitable for delivering nucleic acid molecules (e.g., siNA molecules) to an individual such as a patient; for example delivery systems described in more detail below. In certain embodiments the nucleic acid molecule as described herein, or a pharmaceutically acceptable salt of such compound, or a composition comprising such compound, or a composition comprising the pharmaceutically acceptable salt of such compound, are for use in treating or preventing a disease or disorder associated with expression of p53 in a subject.

In another aspect provided are methods for treating, including preventing, the incidence or severity of a disorder, disease, injury, condition or pathology in which expression of the p53 gene is associated with the etiology or progression of the disorder, disease, injury, condition or pathology. In another embodiments the disorder, disease, injury, condition or pathology involves apoptotic (programmed) cell death. In some embodiments provided is a method for treatment of a subject suffering from a diseases or disorder selected from, without being limited to, ischemia-reperfusion injury, a hearing impairment, a hearing disorder, a balance impairment, a hearing loss, chemotherapy-induced alopecia (hair loss), radiation therapy-induced alopecia, an acute renal failure, an acute kidney injury, a chronic kidney disease (CKD), a side effect associated with anti-cancer therapy, Delayed Graft Function (DGF) in a kidney transplant patient, a spinal cord injury, a brain injury, a seizure, a stroke, a neurodegenerative disorder, Parkinson's disease, Alzheimer's disease, a tumor, a burn, a wound, hyperthermia, hypoxia, ischemia, organ transplantation, myocardial infarction/heart attack, cardiotoxicity, a p53-positive cancer and acute liver failure. In various embodiments the method comprises administering to the subject a nucleic acid compound described herein or a pharmaceutically acceptable salt thereof, in an amount sufficient to down-regulate expression of p53. In various embodiments the method comprises administering to the subject an effective amount of a nucleic acid molecule disclosed herein, or a pharmaceutically acceptable salt of such molecule, thereby treating the disease of disorder.

In some embodiments the subject is suffering from a p53-positive cancer in a subject and the nucleic acid compound, or the pharmaceutically acceptable salt of such compound, or the composition comprising such compound, or the composition comprising the pharmaceutically acceptable salt of such compound, is administered in an amount effective to down-regulate expression of a p53 gene and thereby sensitize the p53-positive cancer to chemotherapy.

In some embodiments the nucleic acid compound disclosed herein, or a pharmaceutically acceptable salt of such compound, or a composition comprising such compound, or a composition comprising the pharmaceutically acceptable salt of such compound, is for use in hematopoietic progenitor expansion or in stimulation of hematopoiesis.

In some embodiments the nucleic acid compound disclosed herein, or a pharmaceutically acceptable salt of such compound, or a composition comprising such compound, or a composition comprising the pharmaceutically acceptable salt of such compound, is for use in homing of p53-null Hematopoietic Stem Cell (HSC).

The preferred methods, materials, and examples that will now be described are illustrative only and are not intended to be limiting; materials and methods similar or equivalent to those described herein can be used in practice or testing of the invention. Other features and advantages of the invention will be apparent from the following detailed description, and from the claims.

DETAILED DESCRIPTION OF THE INVENTION

Provided herein are molecules and compositions which down-regulate expression of a human p53 gene. Inhibition of expression of a p53 gene, was shown to be beneficial in treatment and/or prevention of various diseases and disorders. The present application relates in particular to double-stranded nucleic acid molecules which down-regulate expression of the p53 gene, and to the use of these molecules in the treatment and/or prevention of various diseases and disorders. A non-limiting list of such diseases/disorders is provided herein. Sense strands and complementary antisense strands useful in generating double-stranded nucleic acid molecules are set forth in Table 1, supra. Certain double-stranded nucleic acid compounds are set forth in Tables A, B and E below.

Compounds, compositions and methods for inhibiting p53 are discussed herein at length, and any of said compounds, or pharmaceutically acceptable salts of such compounds, or compositions may be beneficially employed in the treatment of a patient suffering from a disease/a disorder associated with elevated expression of p53 gene.

Accordingly, in one aspect the present disclosure relates in general to nucleic acid compounds which down-regulate expression of p53 gene, and to the use of these novel compounds in the treatment of a subject suffering from a disease, a disorder, or an injury associated with expression of the p53 gene, such as, without being limited to, diseases and disorders described herein.

The nucleic acid compounds disclosed herein possess structures and modifications which may, for example increase activity, increase stability, and or minimize toxicity of the compound.

According to one aspect the present disclosure provides inhibitory oligonucleotide compounds comprising unmodified and modified nucleotides and or unconventional moieties.

In some embodiments a nucleic acid compound disclosed herein includes at least one modified nucleotide selected from the group consisting of a sugar modification, a base modification and an internucleotide linkage modification and may further include DNA, and modified nucleotides or unconventional moieties including LNA (locked nucleic acid), ENA (ethylene-bridged nucleic acid), PNA (peptide nucleic acid), arabinoside, PACE, mirror nucleotide, a nucleotide joined to an adjacent nucleotide by a 2'-5' internucleotide bond or a nucleotide with a 6 carbon sugar.

In various embodiments of a nucleic acid molecule (e.g., dsRNA molecule) as disclosed herein, the antisense strand may be 18-40 nucleotides in length. In some embodiments of a nucleic acid molecule (e.g., dsRNA molecule) as disclosed herein, the antisense strand is 19 nucleotides in length. Similarly the sense strand of a nucleic acid molecule (e.g., dsRNA molecule) as disclosed herein may be 18-40 nucleotides in length. In some preferred embodiments of a nucleic acid molecule (e.g., dsRNA molecule) as disclosed herein, the sense strand is 19 nucleotides in length.

In some embodiments of a nucleic acid molecule (e.g., dsRNA molecule) as disclosed herein, each of the antisense strand and the sense strand are 19 nucleotides in length. In various embodiments of a nucleic acid compound (e.g., dsRNA molecule) as disclosed herein, the duplex region of the compound is 19 nucleotides in length.

In certain embodiments, the sense strand and the antisense strand of a nucleic acid compound (e.g., an dsRNA nucleic acid molecule) as provided herein are separate oligonucleotide strands. In some embodiments, the separate sense strand and antisense strand form a double stranded structure, also known as a duplex, via hydrogen bonding, for example, Watson-Crick base pairing. In some embodiments one or more nucleotide pairs form non-Watson-Crick base pairing. In some embodiments the sense strand and the antisense strand are two separate strands that are covalently linked to each other. In other embodiments, the sense strand and the antisense strands are part of a single oligonucleotide having both a sense and antisense region; in some preferred embodiments the oligonucleotide has a hairpin structure.

In certain embodiments, the nucleic acid molecule is a double stranded nucleic acid (dsRNA) molecule that is symmetrical with regard to overhangs, and has a blunt end on both ends. In other embodiments the nucleic acid molecule is a dsRNA molecule that is symmetrical with regard to overhangs, and has a nucleotide or a non-nucleotide or a combination of a nucleotide and non-nucleotide overhang on both ends of the dsRNA molecule. In some embodiments a symmetrical dsRNA molecule has a 3'-overhang on one side of a duplex occurring on the sense strand; and a 3'-overhang on the other side of the molecule occurring on the 3'-end of the antisense strand. In certain preferred embodiments, the nucleic acid molecule is a dsRNA molecule that is asymmetrical with regard to overhangs, and has a blunt end on one end of the dsRNA molecule and an overhang on the other end of the dsRNA molecule. In some embodiments an asymmetrical dsRNA molecule has a 3'-overhang on one side of a duplex occurring on the sense strand, a blunt end occurring on the 5'-end of the antisense sense strand and a blunt end on the other side of the molecule occurring on both the 5'-end of the sense strand and the 3'-end of the antisense strand. In some embodiments the overhangs are nucleotide overhangs, in other embodiments the overhangs are non-nucleotide overhangs.

In various embodiments the nucleic acid molecule further comprises a capping moiety covalently attached at the 5' end of the sense strand. In some embodiments the dsRNA molecule has a 3'-overhang on one side of a duplex occurring on the sense strand; a 3'-overhang on the other side of the molecule occurring on the 3'-end of the antisense strand and a capping moiety covalently attached at the 5' end of the sense strand. In some embodiments the dsRNA molecule has a 3'-overhang occurring on the sense strand, a capping moiety covalently attached at the 5' end of the sense strand, a blunt end occurring on the 5'-end of the antisense sense strand and a blunt end occurring on the 3'-end of the antisense strand. In some embodiments the overhangs are nucleotide overhangs, in other embodiments the overhangs are non-nucleotide overhangs. In various embodiments the capping moiety is selected from an abasic ribose moiety; an abasic deoxyribose moiety; an inverted abasic ribose moiety; an inverted abasic deoxyribose moiety; a C6-imino-Pi; a mirror nucleotide including L-DNA and L-RNA; a 5' OMe nucleotide; a nucleotide analog, such as without being limited to, a 4',5'-methylene nucleotide; 1-(β-D-erythrofuranosyl)nucleotide; 4'-thio nucleotide, a carbocyclic nucleotide, an alpha-nucleotide; a threo-pentofuranosyl nucleotide; an acyclic 3',4'-seco nucleotide; a 3,4-dihydroxybutyl nucleotide, a 3,5-dihydroxypentyl nucleotide; 5'-aminoalkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; 5'-5'-inverted abasic moiety; 1,4-butanediol phosphate; 5'-amino; bridging or non bridging methylphosphonate and 5'-mercapto moieties. In some preferred embodiments the capping moiety covalently attached to the 5' terminus of the sense strand is selected from an inverted abasic deoxyribose moiety, AM-c6, a C3 non-nucleotide moiety and THNB.

In some embodiments, the nucleic acid molecule has a hairpin structure (having the sense strand and antisense strand on one oligonucleotide), with a loop structure on one end and a blunt end on the other end. In some embodiments, the nucleic acid molecule has a hairpin structure, with a loop structure on one end and an overhang end on the other end; in certain embodiments, the overhang is a 3'-overhang; in certain embodiments the overhang is a 5'-overhang; in certain embodiments the overhang is on the sense strand; in certain embodiments the overhang is on the antisense strand.

In various embodiments, the nucleic acid molecule (e.g., dsRNA molecule) disclosed herein may include one or more modifications or modified nucleotides such as described herein. For example, a nucleic acid molecule (e.g., dsRNA molecule) as provided herein may include a modified nucleotide having a modified sugar; a modified nucleotide having a modified nucleobase; or a modified nucleotide having a modified phosphate group. Similarly, a nucleic acid molecule (e.g., dsRNA molecule) as provided herein may include a modified phosphodiester backbone and/or may include a modified terminal phosphate group.

A nucleic acid molecule (e.g., dsRNA molecules) as provided herein may have one or more nucleotides that include a modified sugar moiety, for example as described herein. In some embodiments the modified sugar moiety is selected from the group consisting of 2'-O-methyl, 2'-methoxyethoxy, 2'-deoxy, 2'-fluoro, 2'-allyl, 2'-O-[2-(methylamino)-2-oxoethyl], 4'-thio, 4'-(CH$_2$)$_2$—O-2'-bridge, 2'-locked nucleic acid, and 2'-O—(N-methylcarbamate). In some preferred embodiments the nucleic acid comprises at least one 2'-O-methyl sugar modified ribonucleotide.

A nucleic acid molecule (e.g., dsRNA molecule) as provided herein may have one or more modified nucleobase(s), for example as described herein.

A nucleic acid molecule (e.g., dsRNA molecule) as provided herein may have one or more modifications to the phosphodiester backbone, for example as described herein.

A nucleic acid molecule (e.g., dsRNA molecule) as provided herein may have one or more modified phosphate group(s), for example as described herein.

A nucleic acid molecule as provided herein may comprise unmodified nucleobases, no modifications to the phosphodiester backbone and unmodified phosphate groups for example as described herein.

In various embodiments, the provided nucleic acid molecule (e.g., dsRNA molecule) may include an unmodified antisense strand and a sense strand having one or more modifications. In some embodiments the provided nucleic acid molecule (e.g., dsRNA molecule) may include an unmodified sense strand and an antisense strand having one or more modifications. In preferred embodiments the provided nucleic acid molecule (e.g., dsRNA molecule) may include one or more modified nucleotides in the both the sense strand and the antisense strand.

A nucleic acid molecule (e.g., dsRNA molecules) as provided herein may include a phosphate group at the 5' end of the sense and/or the antisense strand (i.e. a 5'-terminal phosphate group). In some embodiments a dsRNA molecule disclosed herein may include a phosphate group at the 5' terminus of the antisense strand.

A nucleic acid molecule (e.g., dsRNA molecules) as provided herein may include a phosphate group at the 3' end of the sense and/or the antisense strand (i.e. a 3'-terminal phosphate group). In some embodiments a dsRNA molecule disclosed herein may include a phosphate group at the 3' terminus of the antisense strand.

In some embodiments a nucleic acid molecule (e.g., dsRNA molecules) disclosed herein may include a phosphate group at the 3' terminus of the antisense strand and at the 3' terminus of the sense strand.

In some embodiments a nucleic acid molecule (e.g., dsRNA molecules) disclosed herein includes a phosphate group at the 3' terminus of the antisense strand and at the 3' terminus of the sense strand and is non-phosphorylated at the 5' terminus of the antisense strand and at the 5' terminus of the sense strand.

In some embodiments a nucleic acid molecule (e.g., dsRNA molecules) disclosed herein includes a phosphate group at the 3' terminus of the antisense strand, at the 3' terminus of the sense strand and at the 5' terminus of the antisense strand, and is non-phosphorylated at the 5' terminus of the sense strand.

In some embodiments a nucleic acid molecule (e.g., dsRNA molecules) disclosed herein includes a phosphate group at the 3' terminus of the sense strand and at the 5' terminus of the antisense strand, and is non-phosphorylated and at the 5' terminus of the sense strand and at the 3' terminus of the antisense strand.

In some embodiments a nucleic acid molecule (e.g., dsRNA molecules) disclosed herein the antisense strand and the sense strand of the nucleic acid molecule are non-phosphorylated at both the 3' terminus and at the 5' terminus.

According to one embodiment provided are modified nucleic acid molecules having a structure (A), set forth below:

```
5'    NNNNNNNNNNNNNNNNNNNN-Z 3'  (antisense strand)
      ||||||||||||||||||||
3' Z'-NNNNNNNNNNNNNNNNNNNN-z" 5' (sense strand)
```
(A)

wherein each N is independently any one of A, C, G, U and is independently an unmodified ribonucleotide, a modified ribonucleotide, or an unconventional moiety;
wherein each "|" represents base pairing between each N of the antisense and the corresponding N of the sense strand;
wherein each of Z and Z' is independently present or absent, but if present is independently 1-5 consecutive nucleotides, 1-5 consecutive nucleotide analogues or 1-5 consecutive non-nucleotide moieties or a combination thereof, or a conjugate moiety, covalently attached at the 3' terminus of the strand in which it is present;
wherein z" may be present or absent, but if present is a capping moiety, or a conjugate moiety covalently attached at the 5' terminus of the sense strand; and wherein the sequence of the sense strand is complementary to the sequence of the antisense strand; with the proviso that not each N and N' is an unconventional moiety.

According to one embodiment provided are modified nucleic acid molecules having a structure (A1), set forth below:

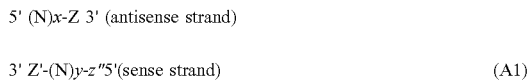

(A1)

wherein each N and N' is independently a ribonucleotide which may be an unmodified ribonucleotide, a modified ribonucleotide, or an unconventional moiety;
wherein each of (N)x and (N')y is an oligonucleotide in which each consecutive N or N' is joined to the adjacent N or N' by a covalent bond;
wherein each of Z and Z' is independently present or absent, but if present independently comprises 1-5 consecutive nucleotides, 1-5 consecutive nucleotide analogues or 1-5 consecutive non-nucleotide moieties or a combination thereof, or a conjugate moiety, covalently attached at the 3' terminus of the strand in which it is present;
wherein z" may be present or absent, but if present is a capping moiety, or a conjugate moiety covalently attached at the 5' terminus of (N')y;
wherein each of x and y is independently an integer between 18 and 40;
wherein the sequence of (N')y is complementary to the sequence of (N)x; and
wherein (N)x comprises an antisense sequence and (N')y comprises a sense sequence; with the proviso that not each N and N' is an unconventional moiety.

According to one embodiment provided are modified nucleic acid molecules having a structure (A2), set forth below:

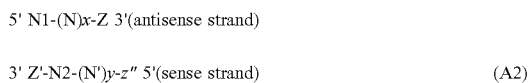

(A2)

wherein each N1, N2, N and N' is independently an unmodified ribonucleotide, a modified ribonucleotide, or an unconventional moiety;
wherein each of (N)x and (N')y is an oligonucleotide in which each consecutive N or N' is joined to the adjacent N or N' by a covalent bond;
wherein each of x and y is independently an integer between 17 and 39;
wherein N2 is covalently bound to (N')y;
wherein N1 is covalently bound to (N)x and is mismatched to the target RNA (SEQ ID NO:1-7) or is a complementary DNA moiety complementary to the target RNA;
wherein N1 is a moiety selected from the group consisting of a natural uridine, a modified: uridine, deoxyribouridine, ribothymidine, deoxyribothymidine, natural adenosine, modified adenosine, deoxyadenosine, adenosine pyrazolotriazine nucleic acid analogue, deoxyadenosine pyrazolotriazine nucleic acid analogue, an abasic ribose moiety and an abasic deoxyribose moiety;
wherein z" may be present or absent, but if present is a capping moiety, a vitamin or a drug moiety covalently attached at the 5' terminus of N2-(N')y;
wherein each of Z and Z' is independently present or absent, but if present is independently 1-5 consecutive nucleotides, 1-5 consecutive nucleotide analogues, 1-5 consecutive non-nucleotide moieties or a combination thereof, a conjugate moiety, covalently attached at the 3' terminus of the strand in which it is present;

wherein the sequence of (N')y is complementary to the sequence of (N)x;

wherein at least a portion of the sequence of (N)x is complementary to a consecutive sequence in the target RNA; and wherein the sequence of N1-(N)x comprises an antisense sequence and N2-(N')y comprises a sense sequence; with the proviso that not each N and N' is an unconventional moiety.

In various embodiments of structures (A), (A1) and (A2) the sense strand and the antisense strand are selected from SEQ ID NOS:8-33. In preferred embodiments of structures (A), (A1) and (A2) the sense strand and the antisense strand are selected from the group consisting of a sense strand SEQ ID NO: 16 and an antisense strand SEQ ID NO: 29, a sense strand SEQ ID NO: 19 and an antisense strand SEQ ID NO: 32 and a sense strand SEQ ID NO: 19 and an antisense strand SEQ ID NO: 28.

In some embodiments of Structure (A2), N1 and N2 form a Watson-Crick base pair. In other embodiments N1 and N2 form a non-Watson-Crick base pair. In some embodiments a base pair is formed between a ribonucleotide and a deoxyribonucleotide. In some embodiments of Structure (A2), x=y=18, x=y=19 or x=y=20. In preferred embodiments x=y=18. When x=18 in N1-(N)x, N1 refers to position 1 and positions 2-19 are included in (N)18. When y=18 in N2-(N')y, N2 refers to position 19 and positions 1-18 are included in (N')18.

In some embodiments of Structure (A2), N1 is covalently bound to (N)x and is mismatched to the target mRNA set forth in SEQ ID NO:1-7. In various embodiments N1 is covalently bound to (N)x and is a DNA moiety complementary to the target mRNA set forth in SEQ ID NO:1-7.

In some embodiments of Structure (A2), the sequence of N2-(N')y is fully complementary to the sequence of N1-(N)x and the sequence of (N)x has complementarity to a consecutive sequence in a target RNA (SEQ ID NOS:1-7).

In some embodiments of Structure (A2), N1 is covalently bound to (N)x and mismatched to the target RNA (SEQ ID NOS:1-7) or is a DNA moiety complementary to the target RNA.

In some embodiments of Structure (A2), N1 is selected from the group consisting of adenosine and deoxyadenosine when the corresponding nucleotide in the target RNA sequence is adenosine. In some embodiments of Structure (A2), N1 is selected from the group consisting of adenosine, deoxyadenosine, deoxythymidine and deoxyuridine when the corresponding nucleotide in the target RNA sequence is cytidine. In some embodiments of Structure (A2), N1 is selected from the group consisting of adenosine, deoxyadenosine, deoxythymidine, uridine and deoxyuridine when the corresponding nucleotide in the target RNA sequence is guanosine. In some embodiments of Structure (A2), $N^1$ is selected from the group consisting of uridine and deoxyuridine when the corresponding nucleotide in the target RNA sequence is uridine. In some embodiments of Structure (A2), N1 and N2 form a base pair between natural or modified: uridine or deoxyuridine, and adenosine or deoxyadenosine. In other embodiments N1 and N2 form a base pair between natural or modified: deoxyuridine and adenosine.

In some embodiments of Structure (A2), the double stranded nucleic acid molecule is a siRNA, siNA or a miRNA. The double stranded nucleic acid molecules as provided herein are also referred to as "duplexes". In some embodiments of nucleic acid molecules according to Structure (A2) as disclosed herein, the double stranded nucleic acid molecule is a chemically modified dsRNA.

In some embodiments of Structure (A2), N1 is selected from a natural uridine and a modified uridine. In some embodiments, N1 is a natural uridine.

In some embodiments of Structure (A2), x=y=18 and N1-(N)x comprises an antisense oligonucleotide and N2-(N')y comprises a sense oligonucleotide present in sequence pairs set forth in Table 1, SEQ ID NOS:8-33.

In some embodiments of Structure (A2), x=y=18 and N1 is selected from a natural or modified uridine, a natural or modified adenine, and a natural or modified thymidine.

In some embodiments of Structure (A2), N1 is a 2' OMe sugar-modified uridine or a 2' OMe sugar-modified adenosine. In certain embodiments of structure (A2), N2 is a 2' OMe sugar modified ribonucleotide or deoxyribonucleotide.

In some embodiments of Structures (A), (A1) and (A2), each N consists of an unmodified ribonucleotide. In some embodiments of Structures (A1) and (A2) each N' consists of an unmodified ribonucleotide. In some preferred embodiments at least one of N and/or N' comprises a chemically modified ribonucleotide, an unmodified deoxyribonucleotide, a chemically modified deoxyribonucleotide or an unconventional moiety, with the proviso that not each N and N' is a deoxyribonucleotide. In some embodiments the unconventional moiety is selected from a mirror nucleotide, an abasic ribose moiety and an abasic deoxyribose moiety. In some embodiments the unconventional moiety is a mirror nucleotide, preferably an L-DNA moiety. In some embodiments at least one of N or N' comprises a 2' OMe sugar-modified ribonucleotide.

In some embodiments of Structures (A1) and (A2) the sequence of (N')y is fully complementary to the sequence of (N)x. In other embodiments of Structures (A1) and (A2) the sequence of (N')y is substantially complementary to the sequence of (N)x.

In some embodiments of Structures (A1) and (A2) (N)x includes an antisense sequence that is fully complementary to about 17 to about 39 consecutive nucleotides in a target mRNA set forth in any one of SEQ ID NO:1-7. In other embodiments of Structures (A1) and (A2) (N)x includes an antisense that is substantially complementary to about 17 to about 39 consecutive nucleotides in a target mRNA set forth in any one of SEQ ID NO:1-7. In some embodiments of Structures (A1) and (A2), the double-stranded nucleic acid compound is blunt ended, for example, wherein each of z", Z and Z' is absent. In an alternative embodiment, at least one of z", Z or Z' is present.

In various embodiments Structures (A), (A1) and (A2), each of Z and Z' is independently present or absent, but if present independently comprises 1-5 consecutive nucleotides, 1-5 consecutive nucleotide analogues or 1-5 consecutive non-nucleotide moieties or a combination thereof, or a conjugate moiety, covalently attached at the 3' terminus of the strand in which it is present. In various embodiments of Structures (A), (A1) and (A2), Z and Z' independently include one or more covalently linked modified and or unmodified nucleotides, including deoxyribonucleotides and ribonucleotides, or one or more (preferably 1-5, most preferable 1-2) unconventional moieties for example inverted abasic deoxyribose moiety or abasic ribose moiety or a mirror nucleotide; one or more (preferably 1-5, most preferable 1-2) non-nucleotide C3 moiety or a derivative thereof, non-nucleotide C4 moiety or a derivative thereof or non-nucleotide C5 moiety or a derivative thereof, an non-nucleotide amino-C6 moiety or a derivative thereof, as defined herein, and the like.

In some embodiments of Structures (A), (A1) and (A2) Z' is absent and Z is present and includes one or more (preferably 1-5, most preferable 1-2) non-nucleotide C3 moieties. In some embodiments Z is absent and Z' is present and includes one or more (preferably 1-5, most preferable 1-2) non-nucleotide C3 moieties. In some embodiments each of Z and Z' independently comprises one or more (preferably 1-5, most preferable 1-2) non-nucleotide C3 moieties or one or more non-nucleotide amino-C6 moieties.

In some embodiments of Structures (A), (A1) and (A2) each of Z and Z' includes an abasic moiety, for example a deoxyriboabasic moiety (referred to herein as "dAb") or riboabasic moiety (referred to herein as "rAb"). In some embodiments each of Z and/or Z' comprises two covalently linked abasic moieties and is for example dAb-dAb or rAb-rAb or dAb-rAb or rAb-dAb, wherein each moiety is covalently attached to an adjacent moiety, preferably via a phospho-based bond. In some embodiments the phospho-based bond includes a phosphorothioate, a phosphonoacetate or a phosphodiester bond. In preferred embodiments the phospho-based bond is a phosphodiester bond.

In some embodiments of Structures (A), (A1) and (A2) each of Z and/or Z' independently includes an alkyl moiety, optionally propane [(CH$_2$)$_3$] moiety (C3) or a derivative thereof including propanol (C3OH) and phospho derivative of propanediol ("C3Pi"). In some embodiments each of Z and/or Z' includes two alkyl moieties and in some examples is C3Pi-C3OH. In the example of C3Pi-C3OH, the 3' terminus of the antisense strand and/or the 3' terminus of the sense strand is covalently attached to a C3 moiety via a phospho-based bond and the C3 moiety is covalently bound to a C3OH moiety via a phospho-based bond. In some embodiments the phospho-based bonds include a phosphorothioate, a phosphonoacetate or a phosphodiester bond. In preferred embodiments the phospho-based bond is a phosphodiester bond.

In some embodiments of Structures (A), (A1) and (A2), Z comprises C3Pi-C3OH. In specific embodiments of Structures (A), (A1) and (A2), Z' comprises C3Pi or C3OH. In some embodiments of Structures (A), (A1) and (A2), a double stranded nucleic acid molecule includes a C3Pi-C3OH moiety covalently attached to the 3' terminus of the antisense strand and a C3Pi or C3OH moiety covalently attached to the 3' terminus of the sense strand.

In some embodiments of Structures (A), (A1) and (A2) z" is present and is selected form the group consisting of an abasic ribose moiety, an abasic deoxyribose moiety, an inverted abasic ribose moiety, an inverted deoxyribose moiety, an inverted deoxyabasic moiety (idAb), amino-C6 moiety (AM-c6), C6-amino-Pi, a non-nucleotide moiety, a mirror nucleotide, a 5,6,7,8-tetrahydro-2-naphthalene butyric phosphodiester (THNB), and a conjugate moiety. In some embodiments conjugate moiety is a vitamin or a drug moiety. In some embodiments of Structures (A), (A1) and (A2) z" is present and is selected from a mirror nucleotide, an abasic moiety and an inverted abasic moiety.

In some embodiments of (A), (A1) and (A2) each N consists of an unmodified ribonucleotide. In some embodiments of Structures (A1) (A2) each N' consists of an unmodified ribonucleotide. In preferred embodiments, at least one of N and/or N' is a chemically modified ribonucleotide, an unmodified deoxyribonucleotide, a chemically modified deoxyribonucleotide or an unconventional moiety, with the proviso that not each N and N' is a deoxyribonucleotide.

In some embodiments a nucleic acid compound of Structures (A), (A1) and (A2) includes at least one ribonucleotide modified in its sugar residue. In some embodiments the compound comprises a modification at the 2' position of the sugar residue. In some embodiments the modification in the 2' position comprises the presence of an amino, a fluoro, an alkoxy or an alkyl moiety. In certain embodiments the 2' modification includes an alkoxy moiety. In preferred embodiments the alkoxy moiety is a methoxy moiety (also referred to as 2'-O-methyl; 2'OMe; 2'OMe; 2'-OCH$_3$). In some embodiments a nucleic acid compound includes 2' OMethyl sugar modified alternating ribonucleotides in one or both of the antisense strand and the sense strand. In other embodiments a compound includes 2' OMe sugar modified ribonucleotides in the antisense strand, (N)x or N1-(N)x, only. In some embodiments, the 2' OMethyl sugar modified ribonucleotides alternate with unmodified nucleotides. In certain embodiments the middle ribonucleotide of the antisense strand; e.g. ribonucleotide in position 10 in a 19-mer strand, is unmodified. In various embodiments the nucleic acid compound includes at least 5 alternating 2' OMe sugar modified ribonucleotides and unmodified ribonucleotides. In additional embodiments a compound of Structure (A1) and/or (A2) includes modified ribonucleotides in alternating positions wherein each ribonucleotide at the 5' terminus and at the 3' terminus of (N)x or N1-(N)x is modified in its sugar residue, and each ribonucleotide at the 5' terminus and at the 3' terminus of (N')y or N2-(N)y is unmodified in its sugar residue. In various embodiments the ribonucleotides in alternating positions are modified at the 2' position of the sugar residue.

In some embodiments of Structures (A), (A1) and (A2), neither of the sense strand nor the antisense strand is phosphorylated at the 3' terminus and at the 5' terminus. In other embodiments one or both of the sense strand and/or the antisense strand are phosphorylated at the 3' termini. In other embodiments one or both of the sense strand and/or the antisense strand are phosphorylated at the 5' terminus.

In some embodiments of Structures (A1) and/or (A2) (N)x and/or (N')y comprises at least one unconventional moiety selected from a mirror nucleotide and a nucleotide joined to an adjacent nucleotide by a 2'-5' internucleotide phosphate bond. In some preferred embodiments the unconventional moiety is a nucleotide joined to an adjacent nucleotide (5'>3') by a 2'-5' internucleotide phosphate bond. In some embodiments the unconventional moiety is a mirror nucleotide. In various embodiments the mirror nucleotide is selected from an L-ribonucleotide (L-RNA) and an L-deoxyribonucleotide (L-DNA). In some embodiments the mirror nucleotide is L-DNA.

In further embodiments of Structures (A1) and/or (A2) (N')y comprises 1-8 modified ribonucleotides wherein the modified ribonucleotide is a deoxyribose (DNA) nucleotide. In certain embodiments (N')y comprises 1, 2, 3, 4, 5, 6, 7, or up to 8 DNA moieties.

In a presently preferred embodiment the inhibitor provided herein is a synthetic, chemically modified double-stranded nucleic acid compound that down-regulates p53 expression and includes an oligonucleotide pair selected from Table 1, SEQ ID NOS:8-33.

In some embodiments the nucleic acid compound includes an antisense strand 5' AGUAGUUUCCAUAGGUCUG 3' (SEQ ID NO: 21) and a sense strand 5' CAGACCUAUGGAAACUACU 3' (SEQ ID NO: 8), identified in Table 1 by the pair name p53_13.

In some embodiments the nucleic acid compound includes an antisense strand 5' UUACAUCUCCCAAACAUCC 3' (SEQ ID NO: 22) and a sense strand 5' GGAUGUUUGGGAGAUGUAA 3' (SEQ ID NO: 9), identified in Table 1 by the pair name p53_34.

In some embodiments the nucleic acid compound includes an antisense strand 5' UUACAUCUC-CCAAACAUCC 3' (SEQ ID NO: 22) and a sense strand 5' GGAUGUUUGGGAGAUGUAU 3' (SEQ ID NO: 18).

In some embodiments the nucleic acid compound includes an antisense strand 5' UAGAAUGUCAGUCUGA-GUC 3' (SEQ ID NO: 23) and a sense strand 5' GACUCA-GACUGACAUUCUA 3' (SEQ ID NO: 10), identified in Table 1 by the pair name p53_35.

In some embodiments the nucleic acid compound includes an antisense strand 5' UUGUAGAAACUAC-CAACCC 3' (SEQ ID NO: 24) and a sense strand 5' GGGUUGGUAGUUUCUACAA 3' (SEQ ID NO: 11), identified in Table 1 by the pair name p53_36.

In some embodiments the nucleic acid compound includes an antisense strand 5' UACAUCUC-CCAAACAUCCC 3' (SEQ ID NO: 25) and a sense strand 5' GGGAUGUUUGGGAGAUGUA 3' (SEQ ID NO: 12), identified in Table 1 by the pair name p53_37.

In some embodiments the nucleic acid compound includes an antisense strand 5' UACAAGUCUUGGUG-GAUCC 3' (SEQ ID NO: 26) and a sense strand 5' GGAUC-CACCAAGACUUGUA 3' (SEQ ID NO: 13), identified in Table 1 by the pair name p53_38.

In some embodiments the nucleic acid compound includes an antisense strand 5' UAUCUCCCAAACAUCC-CUC 3' (SEQ ID NO: 27) and a sense strand 5' GAGGGAU-GUUUGGGAGAUA 3' (SEQ ID NO: 14), identified in Table 1 by the pair name p53_39.

In some embodiments the nucleic acid compound includes an antisense strand 5' UUCAGUCUGAGUCAG-GCCC 3' (SEQ ID NO: 28) and a sense strand 5' GGGC-CUGACUCAGACUGAA 3' (SEQ ID NO: 15), identified in Table 1 by the pair name p53_40.

In some embodiments the nucleic acid compound includes an antisense strand 5' UUCAGUCUGAGUCAG-GCCC 3' (SEQ ID NO: 28) and a sense strand 5' GGGC-CUGACUCAGACUGAU 3' (SEQ ID NO: 19).

In some embodiments the nucleic acid compound includes an antisense strand 5' AAGAAUGUCAGUCUGA-GUC 3' (SEQ ID NO: 29) and a sense strand 5' GACUCA-GACUGACAUUCUU 3' (SEQ ID NO: 16), identified in Table 1 by the pair name p53_41.

In some embodiments the nucleic acid compound includes an antisense strand 5' UUGAGGUAGGUG-CAAAUGC 3' (SEQ ID NO: 30) and a sense strand 5' GCAUUUGCACCUACCUCAA 3' (SEQ ID NO: 17), identified in Table 1 by the pair name p53_42.

In some embodiments the nucleic acid compound includes an antisense strand 5' AUACAUCUC-CCAAACAUCC 3' (SEQ ID NO: 31) and a sense strand 5' GGAUGUUUGGGAGAUGUAU 3' (SEQ ID NO: 18), identified in Table 1 by the pair name p53_43.

In some embodiments the nucleic acid compound includes an antisense strand 5' AUACAUCUC-CCAAACAUCC 3' (SEQ ID NO: 31) and a sense strand 5' GGAUGUUUGGGAGAUGUAA 3' (SEQ ID NO: 9).

In some embodiments the nucleic acid compound includes an antisense strand 5' AUCAGUCUGAGUCAG-GCCC 3' (SEQ ID NO: 32) and a sense strand 5' GGGC-CUGACUCAGACUGAU 3' (SEQ ID NO: 19), identified in Table 1 by the pair name p53_44.

In some embodiments the nucleic acid compound includes an antisense strand 5' UGUAGUUUCCAUAGGU-CUG 3' (SEQ ID NO: 33) and a sense strand 5' CAGAC-CUAUGGAAACUACA 3' (SEQ ID NO: 20), identified in Table 1 by the pair name p53_45.

In some embodiments the nucleic acid compound includes an antisense strand 5' AGUAGUUUCCAUAGGU-CUG 3' (SEQ ID NO: 21) and a sense strand 5' CAGAC-CUAUGGAAACUACA 3' (SEQ ID NO: 20).

In some embodiments of structure (A), each A, C, G, U is unmodified ribonucleotide or a 2'-O-methyl sugar modified ribonucleotide that alternate according to the following pattern:

wherein each N is an unmodified ribonucleotide,
wherein each <u>N</u> is a 2'-O-methyl sugar modified ribonucleotide,
wherein each "|" represents base pairing between N and N;
wherein in the antisense strand, each consecutive N or <u>N</u> is joined to the adjacent N or <u>N</u> a covalent bond;
wherein in the sense strand, each consecutive N or <u>N</u> is joined to the adjacent N or <u>N</u> a covalent bond;
wherein the sequence of the sense strand is complementary to the sequence of the antisense strand; and
wherein the antisense strand sequence and the sense strand sequence are set forth in SEQ ID NOS:8-33; or a pharmaceutically acceptable salt of such compound.

Certain preferred duplexes according to this embodiment of structure (A) are set forth herein below in Table A.

TABLE A

| Duplex Name | Sense strand (5'>3') | Antisense strand (5'>3') |
|---|---|---|
| p53_34 | G<u>G</u>A<u>U</u>G<u>U</u>U<u>U</u>G<u>G</u>G<u>A</u>G<u>A</u>U<u>G</u>UAA | U<u>U</u>A<u>C</u>A<u>U</u>C<u>U</u>C<u>C</u>C<u>A</u>A<u>A</u>C<u>A</u>UCC |
| p53_35 | G<u>A</u>C<u>U</u>C<u>A</u>G<u>A</u>C<u>U</u>G<u>A</u>C<u>A</u>U<u>U</u>CUA | U<u>A</u>G<u>A</u>A<u>U</u>G<u>U</u>C<u>A</u>G<u>U</u>C<u>U</u>G<u>A</u>GUC |
| p53_36 | G<u>G</u>G<u>U</u>U<u>G</u>G<u>U</u>A<u>G</u>U<u>U</u>U<u>C</u>U<u>A</u>CAA | U<u>U</u>G<u>U</u>A<u>G</u>A<u>A</u>A<u>C</u>U<u>A</u>C<u>C</u>A<u>A</u>CCC |
| p53_37 | G<u>G</u>G<u>A</u>U<u>G</u>U<u>U</u>U<u>G</u>G<u>G</u>A<u>G</u>A<u>U</u>GUA | U<u>A</u>C<u>A</u>U<u>C</u>U<u>C</u>C<u>C</u>A<u>A</u>A<u>C</u>A<u>U</u>CCC |
| p53_38 | G<u>G</u>A<u>U</u>C<u>C</u>A<u>C</u>C<u>A</u>A<u>G</u>A<u>C</u>U<u>U</u>GUA | U<u>A</u>C<u>A</u>A<u>G</u>U<u>C</u>U<u>U</u>G<u>G</u>U<u>G</u>G<u>A</u>UCC |
| p53_39 | G<u>A</u>G<u>G</u>G<u>A</u>U<u>G</u>U<u>U</u>U<u>G</u>G<u>G</u>A<u>G</u>AUA | U<u>A</u>U<u>C</u>U<u>C</u>C<u>C</u>A<u>A</u>A<u>C</u>A<u>U</u>C<u>C</u>CUC |
| p53_40 | G<u>G</u>G<u>C</u>C<u>U</u>G<u>A</u>C<u>U</u>C<u>A</u>G<u>A</u>C<u>U</u>GAA | U<u>U</u>C<u>A</u>G<u>U</u>C<u>U</u>G<u>A</u>G<u>U</u>C<u>A</u>G<u>G</u>CCC |
| p53_41 | G<u>A</u>C<u>U</u>C<u>A</u>G<u>A</u>C<u>U</u>G<u>A</u>C<u>A</u>U<u>U</u>CUU | A<u>A</u>G<u>A</u>A<u>U</u>G<u>U</u>C<u>A</u>G<u>U</u>C<u>U</u>G<u>A</u>GUC |
| p53_42 | G<u>C</u>A<u>U</u>U<u>U</u>G<u>C</u>A<u>C</u>C<u>U</u>A<u>C</u>C<u>U</u>CAA | U<u>U</u>G<u>A</u>G<u>G</u>U<u>A</u>G<u>G</u>U<u>G</u>C<u>A</u>A<u>A</u>UGC |
| p53_43 | G<u>G</u>A<u>U</u>G<u>U</u>U<u>U</u>G<u>G</u>G<u>A</u>G<u>A</u>U<u>G</u>UAU | A<u>U</u>A<u>C</u>A<u>U</u>C<u>U</u>C<u>C</u>C<u>A</u>A<u>A</u>C<u>A</u>UCC |
| p53_44 | G<u>G</u>G<u>C</u>C<u>U</u>G<u>A</u>C<u>U</u>C<u>A</u>G<u>A</u>C<u>U</u>GAU | A<u>U</u>C<u>A</u>G<u>U</u>C<u>U</u>G<u>A</u>G<u>U</u>C<u>A</u>G<u>G</u>CCC |
| p53_45 | C<u>A</u>G<u>A</u>C<u>C</u>U<u>A</u>U<u>G</u>G<u>A</u>A<u>A</u>C<u>U</u>ACA | U<u>G</u>U<u>A</u>G<u>U</u>U<u>U</u>C<u>C</u>A<u>U</u>A<u>G</u>G<u>U</u>CUG |

In all tables above and below the duplex names are identified by prefixes "p53" and "TP53" that are used interchangeably.

For all dsRNA compounds in Table A:
A, U, G, C—designates an unmodified ribonucleotide;
<u>A</u>, <u>U</u>, <u>G</u>, <u>C</u>—designates a 2-O-methyl sugar modified ribonucleotide;

In various embodiments, of the nucleic acid compounds in Table A, the ribonucleotide at the 3' terminus and at the 5' terminus in each of the antisense strand and the sense strand may be phosphorylated or non-phosphorylated. In some embodiments, of the nucleic acid compounds in Table A, in each of the antisense strand and the sense strand the ribonucleotide at the 3' terminus is phosphorylated and the ribonucleotide at the 5' terminus is non-phosphorylated. In some embodiments, in each of the nucleic acid compound in Table A, the antisense strand and the sense strand are non-phosphorylated at both the 3' terminus and the 5' terminus.

Certain preferred duplexes for generation of double-stranded nucleic acid compounds for down-regulation of a p53 gene are set forth herein below in Table B. Further preferred duplexes are provided in the Examples section below.

ety (idAb), amino-C6 moiety (AM-c6), C6-amino-pi, a non-nucleotide moiety, a mirror nucleotide, a 5,6,7,8-tetra-hydro-2-naphthalene butyric phosphodiester (THNB) and a conjugate moiety.

pi—designates 3'-phosphate.

z—designates capping moiety $—designates no terminal phosphate dT$—designates thymidine (no phosphate)

TABLE B

Certain preferred duplexes.

| Duplex Name | Sense (N')y 5->3 | Antisense (N)x 5->3 |
|---|---|---|
| p53_13 | cap-CAGACCUAUGGAAACUACU-C3-pi | AGUAGUuUCCAUAGGUCUG-C3-C3 |
|  | cap-CAGACCUAUGGAAAcuacu-C3-pi | AGUAGUuUCCAUAGGUCUG-C3-C3 |
|  | cap-CAGACCUAUGGAAACUACU-pi | AGUAGUUUCCAUAGGUCUG-pi |
|  | cap-CAGACCUAUGGAAAcuaca-C3-pi | UGUAGUuUCCAUAGGUCUG-C3-C3 |
|  | cap-CAGACCUAUGGAAACUACA-C3-pi | UGUAGUUUCCAUAGGUCUG-pi |
|  | cap-CAGACCUAUGGAAACUACA-pi | UGUAGUUUCCAUAGGUCUG |
|  | cap-CAGACCUAUGGAAACUACA | UGUAGUUUCCAUAGGUCUG |
| p53_34 | cap-GGAUGUUUGGGAGAUGUAA-C3-pi | UUACAUcUCCCAAACAUCC-C3-C3 |
|  | cap-GGAUGUUUGGGAGAuguaa-C3-pi | UUACAUcUCCCAAACAUCC-C3-C3 |
|  | cap-GGAUGUUUGGGAGAuguaa-C3-pi | AUACAUcUCCCAAACAUCC-C3-C3 |
|  | cap-GGAUGUUUGGGAGAUGUAU-C3-pi | UUACAUcUCCCAAACAUCC-C3-C3 |
|  | cap-GGAUGUUUGGGAGAuguau-C3-pi | AUACAUcUCCCAAACAUCC-C3-C3 |
|  | GGAUGUUUGGGAGAUGUAUzdTzdT$ | AUACAUCUCCCAAACAUCCzdTzdT$ |
| p53_35 | cap-GACUCAGACUGACAuucua-C3-pi | UAGAAUgUCAGUCUGAGUC-C3-C3 |
|  | cap-GACUCAGACUGACAUUCUA-C3-pi | UAGAAUgUCAGUCUGAGUC-C3-C3 |
|  | cap-GACUCAGACUGACAUUCUA-C3-pi | UAGAAuGUCAGUCUGAGUC-C3-C3 |
|  | cap-GACUCAGACUGACAUUCUA-C3-pi | UAGAAUgUCAGUCUGAGUC-C3-C3 |
|  | GACUCAGACUGACAUUCUAzdTzdT$ | UAGAAUGUCAGUCUGAGUCzdTzdT$ |
| p53_40 | cap-GGGCCUGACUCAGACUGAA-C3-pi | UUCAGUcUGAGUCAGGCCC-C3-C3 |
|  | cap-GGGCCUGACUCAGAcugaa-C3-pi | UUCAGUcCUGAGUCAGGCCC-C3-C3 |
|  | cap-GGGCCUGACUCAGACUGAU-C3-pi | UUCAGaCUGAGUCAGGCCC-C3-C3 |
|  | cap-GGGCCUGACUCAGAcugaa-C3-pi | AUCAGUcUGAGUCAGGCCC-C3-C3 |
|  | cap-GGGCCUGACUCAGACUGAA-C3-pi | UUCAGUcUGAGUCAGGCCC-C3-C3 |
|  | cap-GGGCCUGACUCAGACUGAU-C3-pi | AUCAGUcUGAGUCAGGCCC-C3-C3 |
|  | cap-GGGCCUGACUCAGACUGAA-C3-pi | UUCAGuCUGAGUCAGGCCC-C3-C3 |
|  | GGGCCUGACUCAGACUGAAzdTzdT$ | UUCAGUCUGAGUCAGGCCCzdTzdT$ |
| p53_41 | cap-GACUCAGACUGACAuucuu-C3-pi | AAGAAUgUCAGUCUGAGUC-C3-C3 |
|  | cap-GACUCAGACUGACAUUCUU-C3-pi | AAGAAUgUCAGUCUGAGUC-C3-C3 |
|  | cap-GACUCAGACUGACAUUCUU-C3-pi | AAGAAUgUCAGUCUGAGUC-C3-C3 |
|  | cap-GACUCAGACUGACAUUCUU-C3-pi | AAGAAuGUCAGUCUGAGUC-C3-C3 |
|  | GACUCAGACUGACAUUCUUzdTzdT$ | AAGAAUGUCAGUCUGAGUCzdTzdT$ |
| p53_43 | cap-GGAUGUUUGGGAGAuguau-C3-pi | AUACAUcUCCCAAACAUCC-C3-C3 |
|  | cap-GGAUGUUUGGGAGAUGUAU-C3-pi | AUACAUcUCCCAAACAUCC-C3-C3 |
| p53_44 | cap-GGGCCUGACUCAGACUGAU-C3-pi | AUCAGUcUGAGUCAGGCCC-C3-C3 |
|  | cap-GGGCCUGACUCAGAcugau-C3-pi | AUCAGuCUGAGUCAGGCCC-C3-C3 |
|  | cap-GGGCCUGACUCAGACUGAU-C3-pi | AUCAGuCUGAGUCAGGCCC-C3-C3 |
|  | cap-GGGCCUGACUCAGACUGAU-C3-pi | AUCAGUcUGAGUCAGGCCC-C3-C3 |
| p53_45 | cap-CAGACCUAUGGAAAcuaca-C3-pi | UGUAGUuUCCAUAGGUCUG-C3-C3 |
|  | cap-CAGACCUAUGGAAACUACA-C3-pi | UGUAGUUUCCAUAGGUCUG-pi |
|  | cap-CAGACCUAUGGAAACUACA-pi | UGUAGUUUCCAUAGGUCUG |

For all double-stranded nucleic acid compounds in Table B:

A, U, G, C—designates an unmodified ribonucleotide;

A, U, G, C—designates a 2-O-methyl sugar modified ribonucleotide;

a, u, c, g—designates a nucleotide joined to an adjacent nucleotide by a 2'-5' internucleotide phosphate bond (5'>3');

cap—designates a capping moiety. In some preferred embodiments the capping moiety is the group consisting of an abasic ribose moiety, an abasic deoxyribose moiety, an inverted deoxyribose moiety, an inverted deoxyabasic moi- C3—designates 1,3-Propanediol, mono(dihydrogen phosphate) (C3) [CAS RN: 13507-42-1].

C3-C3—designates two consecutive C3 molecules.

In various embodiments of the nucleic acid compounds described in Table B, supra, the C3-C3 non-nucleotide overhang covalently attached at the 3' terminus of the antisense strand is phosphorylated (—C3-C3-pi).

In some embodiments of the nucleic acid compounds described in Table B, supra, in each of the nucleic acid compounds, the ribonucleotide at the 5' terminus in the antisense strand is phosphorylated. In some embodiments of the nucleic acid compounds described in Table B, supra, in each of the nucleic acid compounds, the ribonucleotide at the 5' terminus in the antisense strand is non-phosphorylated.

According to one embodiment provided is a modified nucleic acid compound having a sense strand and an antisense strand set forth below:

```
5' cap-CAGACCUAUGGAAACUACU-C3-pi 3'
(sense strand; SEQ ID NO: 8)

5' AGUAGUuUCCAUAGGUCUG-C3-C3 3'
(antisense strand; SEQ ID NO: 21)
``` wherein each of A, U, G and C is an unmodified ribonucleotide;
wherein each of A, U and C is a 2'-O-methyl sugar modified ribonucleotide;
wherein u is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound. According to one embodiment of such compound the 5' cap covalently attached at the 5' terminus of the sense strand is 1,3-propanediol, mono(dihydrogen phosphate) (C3); and in the antisense strand the ribonucleotide at the 5' terminus is phosphorylated and the overhang at the 3' terminus is phosphorylated (—C3-C3-pi).

According to one embodiment provided is a modified nucleic acid compound having a sense strand and an antisense strand set forth below:

```
5' cap-CAGACCUAUGGAAAcuacu-C3-pi 3'
(sense strand; SEQ ID NO: 8)

5' AGUAGUuUCCAUAGGUCUG-C3-C3 3'
(antisense strand; SEQ ID NO: 21)
``` wherein each of A, U, G and C is an unmodified ribonucleotide;
wherein each of A, U and C is a 2'-O-methyl sugar modified ribonucleotide;
wherein each of a, c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound. According to one embodiment of such compound the 5' cap covalently attached at the 5' terminus of the sense strand is 1,3-propanediol, mono(dihydrogen phosphate) (C3); and in the antisense strand the ribonucleotide at the 5' terminus is phosphorylated and the overhang at the 3' terminus is phosphorylated (—C3-C3-pi).

According to one embodiment provided is a modified nucleic acid compound having a sense strand and an antisense strand set forth below:

```
5' cap-CAGACCUAUGGAAACUACU-pi 3'
(sense strand; SEQ ID NO: 8)

5' AGUAGUUUCCAUAGGUCUG-pi 3'
(antisense strand; SEQ ID NO: 21)
``` wherein each of A, U, G and C is an unmodified ribonucleotide;
wherein each of A, U, G and C is a 2'-O-methyl sugar modified ribonucleotide;
wherein in the antisense strand and in the sense strand, each consecutive ribonucleotide is joined to the next ribonucleotide by a phosphodiester bond;
wherein the sense strand comprises a 5' cap covalently attached at the 5' terminus of the strand; and
wherein in the sense strand and in the antisense strand the ribonucleotide at the 3' terminus is phosphorylated (pi); or
a pharmaceutically acceptable salt of such compound.

According to one embodiment provided is a modified nucleic acid compound having a sense strand and an antisense strand set forth below:

```
5' cap-CAGACCUAUGGAAAcuaca-C3-pi 3'
(sense strand; SEQ ID NO: 20)

5' UGUAGUuUCCAUAGGUCUG-C3-C3 3'
(antisense strand; SEQ ID NO: 33)
``` wherein each of A, U, G and C is an unmodified ribonucleotide;
wherein each of A, U and C is a 2'-O-methyl sugar modified ribonucleotide;
wherein each of a, u and c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-CAGACCUAUGGAAACUACA-C3-pi 3'
(sense strand; SEQ ID NO: 20)

5' UGUAGUUUCCAUAGGUCUG-pi 3'
(antisense strand; SEQ ID NO: 33)
``` wherein each of A, U, G and C is an unmodified ribonucleotide;
wherein each of A, U and C is a 2'-O-methyl sugar modified ribonucleotide;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein in the sense strand the overhang at the 3' terminus is phosphorylated (C3-pi); and
wherein in the antisense strand the ribonucleotide at the 3' terminus is phosphorylated (pi); or
a pharmaceutically acceptable salt of such compound.

According to one embodiment provided is a modified nucleic acid compound having a sense strand and an antisense strand set forth below:

```
5' cap-CAGACCUAUGGAAACUACA-pi 3'
(sense strand; SEQ ID NO: 20)

5' UGUAGUUUCCAUAGGUCUG 3'
(antisense strand; SEQ ID NO: 33)
``` wherein each of A, U, G and C is an unmodified ribonucleotide;
wherein each of A, U and C is a 2'-O-methyl sugar modified ribonucleotide;
wherein in the antisense strand and in the sense strand, each consecutive ribonucleotide is joined to the next ribonucleotide by a phosphodiester bond;
wherein the sense strand comprises a 5' cap covalently attached at the 5' terminus of the strand; and
wherein in the sense strand the ribonucleotide at the 3' terminus is phosphorylated or
a pharmaceutically acceptable salt of such compound.

According to one embodiment provided is a modified nucleic acid compound having a sense strand and an antisense strand set forth below:

```
5' cap-CAGACCUAUGGAAACUACA 3'
(sense strand; SEQ ID NO: 20)

5' UGUAGUUUCCAUAGGUCUG 3'
(antisense strand; SEQ ID NO: 33)
``` wherein each of A, U, G and C is an unmodified ribonucleotide;
wherein each of A, U and C is a 2'-O-methyl sugar modified ribonucleotide;
wherein in the antisense strand and in the sense strand, each consecutive ribonucleotide is joined to the next ribonucleotide by a phosphodiester bond; and
wherein the sense strand comprises a 5' cap covalently attached at the 5' terminus of the strand; or
a pharmaceutically acceptable salt of such compound.

According to one embodiment provided is a modified nucleic acid compound having a sense strand and an antisense strand set forth below:

```
5' C3-CAGACCUAUGGAAACUACU-C3-pi 3'
(sense strand; SEQ ID NO: 8)

5' phos-AGUAGUuUCCAUAGGUCUG-C3-C3-pi 3'
(antisense strand; SEQ ID NO: 21)
``` wherein each of A, U, G and C is an unmodified ribonucleotide;
wherein each of A, U and C is a 2'-O-methyl sugar modified ribonucleotide;
wherein u is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' C3 cap covalently attached at the 5' terminus of the strand;
wherein the antisense strand comprises a C3-C3 non-nucleotide overhang covalently attached at the 3' terminus of the strand; and
wherein the 3' terminus of both the sense strand and the antisense strand is phosphorylated (pi); and
wherein the 5' terminus of the antisense strand is phosphorylated (phos); or
a pharmaceutically acceptable salt of such compound.

According to one embodiment provided is a modified nucleic acid compound having a sense strand and an antisense strand set forth below:

```
5' C3-CAGACCUAUGGAAAcuaca-C3-pi 3'
(sense strand; SEQ ID NO: 20)

5' phos-AGUAGUuUCCAUAGGUCUG-C3-C3-pi 3'
(antisense strand; SEQ ID NO: 21)
``` wherein each of A, U, G and C is an unmodified ribonucleotide;
wherein each of A, U and C is a 2'-O-methyl sugar modified ribonucleotide;
wherein each of a, u and c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' C3 cap covalently attached at the 5' terminus of the strand;
wherein the antisense strand comprises a C3-C3 non-nucleotide overhang covalently attached at the 3' terminus of the strand; and
wherein the 3' terminus of both the sense strand and the antisense strand is phosphorylated (pi); and
wherein the 5' terminus of the antisense strand is phosphorylated (phos); or
a pharmaceutically acceptable salt of such compound.

According to one embodiment provided is a modified nucleic acid compound having a sense strand and an antisense strand set forth below:

```
5' cap-GGAUGUUUGGGAGAUGUAA-C3-pi 3'
(sense strand; SEQ ID NO: 9)

5' UUACAUcUCCCAAACAUCC-C3-C3 3'
(antisense strand; SEQ ID NO: 22)
``` wherein each of A, U, G and C is an unmodified ribonucleotide;
wherein each of A, U and C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGAUGUUUGGGAGAuguaa-C3-pi 3'
(sense strand; SEQ ID NO: 9)

5' UUACAUcUCCCAAACAUCC-C3-C3 3'
(antisense strand; SEQ ID NO: 22)
``` wherein each of A, U, G and C is an unmodified ribonucleotide;
wherein each of U and C is a 2'-O-methyl sugar modified ribonucleotide;
wherein each of a, u, c and g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGAUGUUUGGGAGAuguaa-C3-pi 3'
(sense strand; SEQ ID NO: 9)

5' AUACAUcUCCCAAACAUCC-C3-C3 3'
(antisense strand; SEQ ID NO: 31)
``` wherein each of A, U, G and C is an unmodified ribonucleotide;
wherein each of A, U and C is a 2'-O-methyl sugar modified ribonucleotide;
wherein each of a, u, c and g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGAUGUUUGGGAGAUGUAU-C3-pi 3'
(sense strand; SEQ ID NO: 18)

5' UUACAUcUCCCAAACAUCC-C3-C3 3'
(antisense strand; SEQ ID NO: 22)
``` wherein each of A, U, G and C is an unmodified ribonucleotide;
wherein each of U and C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGAUGUUUGGGAGAuguau-C3-pi 3'
(sense strand; SEQ ID NO: 18)

5' AUACAUcUCCCAAACAUCC-C3-C3 3'
(antisense strand; SEQ ID NO: 31)
``` wherein each of A, U, G and C is an unmodified ribonucleotide;

wherein each of U and C is a 2'-O-methyl sugar modified ribonucleotide;
wherein each of a, u, c and g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' GGAUGUUUGGGAGAUGUAU-dTdT 3'
(sense strand; SEQ ID NO: 18)

5' AUACAUCUCCCAAACAUCC-dTdT 3'
(antisense strand; SEQ ID NO: 31)
``` wherein each of A, U, G and C is an unmodified ribonucleotide;
wherein in the antisense strand and in the sense strand, each consecutive ribonucleotide is joined to the next ribonucleotide by a phosphodiester bond;
wherein each of the sense strand and the antisense strand comprises a two nucleotide thymidine-thymidine (dTdT) overhang covalently attached at the 3' terminus of the strand; and
wherein the 3' terminus of the sense strand and of the antisense strand is non-phosphorylated; or
a pharmaceutically acceptable salt of such compound.

According to one embodiment provided is a modified nucleic acid compound having a sense strand and an antisense strand set forth below:

```
5' cap-GACUCAGACUGACAuucua-C3-pi 3'
(sense strand; SEQ ID NO: 10)

5' UAGAAUgUCAGUCUgAGUC-C3-C3 3'
(antisense strand; SEQ ID NO: 23)
``` wherein each of A, U, G and C is an unmodified ribonucleotide;
wherein each of U, G and C is a 2'-O-methyl sugar modified ribonucleotide;
wherein each of a, u, c and g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GACUCAGACUGACAUUCUA-C3-pi 3'
(sense strand; SEQ ID NO: 10)

5' UAGAAUgUCAGUCUgAGUC-C3-C3 3'
(antisense strand; SEQ ID NO: 23)
``` wherein each of A, U, G and C is an unmodified ribonucleotide;
wherein each of U, G and C is a 2'-O-methyl sugar modified ribonucleotide;
wherein g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GACUCAGACUGACAUUCUA-C3-pi 3'
(sense strand; SEQ ID NO: 10)

5' UAGAAuGUCAGUCUgAGUC-C3-C3 3'
(antisense strand; SEQ ID NO: 23)
``` wherein each of A, U, G and C is an unmodified ribonucleotide;
wherein each of U, G and C is a 2'-O-methyl sugar modified ribonucleotide;
wherein u is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GACUCAGACUGACAUUCUA-C3-pi 3'
(sense strand; SEQ ID NO: 10)

5' UAGAAUgUCAGUCUGAGUC-C3-C3 3'
(antisense strand; SEQ ID NO: 23)
``` wherein each of A, U, G and C is an unmodified ribonucleotide;
wherein each of U, G and C is a 2'-O-methyl sugar modified ribonucleotide;
wherein g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' GACUCAGACUGACAUUCUA-dTdT 3'
(sense strand; SEQ ID NO: 10)

5' UAGAAUGUCAGUCUGAGUC-dTdT 3'
(antisense strand; SEQ ID NO: 23)
``` wherein each of A, U, G and C is an unmodified ribonucleotide;
wherein in the antisense strand and in the sense strand, each consecutive ribonucleotide is joined to the next ribonucleotide by a phosphodiester bond;
wherein each of the sense strand and the antisense strand comprises a two nucleotide thymidine-thymidine (dTdT) overhang covalently attached at the 3' terminus of the strand; and
wherein the 3' terminus of the sense strand and of the antisense strand is non-phosphorylated; or
a pharmaceutically acceptable salt of such compound.

According to one embodiment provided is a modified nucleic acid compound having a sense strand and an antisense strand set forth below:

```
5' cap-GGGCCUGACUCAGACUGAA-C3-pi 3'
(sense strand; SEQ ID NO: 15)

5' UUCAGUcUGAGUCAGGCCC-C3-C3 3'
(antisense strand; SEQ ID NO: 28)
``` wherein each of A, U, G and C is an unmodified ribonucleotide;
wherein each of U and C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGGCCUGACUCAGAcugaa-C3-pi 3'
(sense strand; SEQ ID NO: 15)

5' UUCAGuCUGAGUCAGGCCC-C3-C3 3'
(antisense strand; SEQ ID NO: 28)
``` wherein each of A, U, G and C is an unmodified ribonucleotide;
wherein each of U and C is a 2'-O-methyl sugar modified ribonucleotide;
wherein each of a, u, c and g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGGCCUGACUCAGACUGAU-C3-pi 3'
(sense strand; SEQ ID NO: 19)

5' UUCAGuCUGAGUCAGGCCC-C3-C3 3'
(antisense strand; SEQ ID NO: 28)
``` wherein each of A, U, G and C is an unmodified ribonucleotide;
wherein each of U and C is a 2'-O-methyl sugar modified ribonucleotide;
wherein u is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;

wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGGCCUGACUCAGAcugau-C3-pi 3'
(sense strand; SEQ ID NO: 19)

5' AUCAGuCUGAGUCAGGCCC-C3-C3 3'
(antisense strand; SEQ ID NO: 32)
``` wherein each of A, U, G and C is an unmodified ribonucleotide;
wherein each of U and C is a 2'-O-methyl sugar modified ribonucleotide;
wherein each of a, c and g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGGCCUGACUCAGACUGAA-C3-pi 3'
(sense strand; SEQ ID NO: 15)

5' UUCAGUcUGAGUCAGGCCC-C3-C3 3'
(antisense strand; SEQ ID NO: 28)
``` wherein each of A, U, G and C is an unmodified ribonucleotide;
wherein each of U and C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGGCCUGACUCAGACUGAU-C3-pi 3'
(sense strand; SEQ ID NO: 19)

5' AUCAGuCUGAGUCAGGCCC-C3-C3 3'
(antisense strand; SEQ ID NO: 32)
``` wherein each of A, U, G and C is an unmodified ribonucleotide;
wherein each of U and C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGGCCUGACUCAGACUGAA-C3-pi 3'
(sense strand; SEQ ID NO: 15)

5' UUCAGuCUGAGUCAGGCCC-C3-C3 3'
(antisense strand; SEQ ID NO: 28)
``` wherein each of A, U, G and C is an unmodified ribonucleotide;
wherein each of U and C is a 2'-O-methyl sugar modified ribonucleotide;
wherein each of u is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' GGGCCUGACUCAGACUGAA-dTdT 3'
(sense strand; SEQ ID NO: 15)

5' UUCAGUCUGAGUCAGGCCC-dTdT 3'
(antisense strand; SEQ ID NO: 28)
``` wherein each of A, U, G and C is an unmodified ribonucleotide;

wherein in the antisense strand and in the sense strand, each consecutive ribonucleotide is joined to the next ribonucleotide by a phosphodiester bond;

wherein each of the sense strand and the antisense strand comprises a two nucleotide thymidine-thymidine (dTdT) overhang covalently attached at the 3' terminus of the strand; and wherein the 3' terminus of the sense strand and of the antisense strand is non-phosphorylated; or a pharmaceutically acceptable salt of such compound.

According to one embodiment provided is a modified nucleic acid compound having a sense strand and an antisense strand set forth below:

```
5' cap-GACUCAGACUGACAuucuu-C3-pi 3'
(sense strand; SEQ ID NO: 16)

5' AAGAAUgUCAGUCUGAGUC-C3-C3 3'
(antisense strand; SEQ ID NO: 29)
``` wherein each of A, U, G and C is an unmodified ribonucleotide;

wherein each of U, G and C is a 2'-O-methyl sugar modified ribonucleotide;

wherein each of u, c and g is a ribonucleotide joined to an adjacent ribonucleotide (5'>3') by a 2'-5' internucleotide phosphate bond;

wherein in the antisense strand and in the sense strand, each consecutive ribonucleotide is joined to the next ribonucleotide by a phosphodiester bond;

wherein the sense strand comprises a 1,3-propanediol, mono (dihydrogen phosphate) (C3) non-nucleotide overhang covalently attached at the 3' terminus of the strand;

wherein the sense strand comprises a 5' cap covalently attached at the 5' terminus of the strand;

wherein the antisense strand comprises a C3-C3 non-nucleotide overhang covalently attached at the 3' terminus of the strand; and wherein the 3' terminus of the sense strand is phosphorylated (pi); or a pharmaceutically acceptable salt of such compound. According to one embodiment of such compound the 5' cap covalently attached at the 5' terminus of the sense strand is 1,3-propanediol, mono(dihydrogen phosphate) (C3); and in the antisense strand the ribonucleotide at the 5' terminus is phosphorylated (phos) and the overhang at the 3' terminus is phosphorylated (—C3-C3-pi).

According to one embodiment provided is a modified nucleic acid compound having a sense strand and an antisense strand set forth below:

```
5' cap-GACUCAGACUGACAUUCUU-C3-pi 3'
(sense strand; SEQ ID NO: 16)

5' AAGAAUgUCAGUCUGAGUC-C3-C3 3'
(antisense strand; SEQ ID NO: 29)
``` wherein each of A, U, G and C is an unmodified ribonucleotide;

wherein each of U, G and C is a 2'-O-methyl sugar modified ribonucleotide;

wherein g is a ribonucleotide joined to an adjacent ribonucleotide (5'>3') by a 2'-5' internucleotide phosphate bond;

wherein in the antisense strand and in the sense strand, each consecutive ribonucleotide is joined to the next ribonucleotide by a phosphodiester bond;

wherein the sense strand comprises a 1,3-propanediol, mono (dihydrogen phosphate) (C3) non-nucleotide overhang covalently attached at the 3' terminus of the strand;

wherein the sense strand comprises a 5' cap covalently attached at the 5' terminus of the strand;

wherein the antisense strand comprises a C3-C3 non-nucleotide overhang covalently attached at the 3' terminus of the strand; and wherein the 3' terminus of the sense strand is phosphorylated (pi); or a pharmaceutically acceptable salt of such compound.

According to one embodiment provided is a modified nucleic acid compound having a sense strand and an antisense strand set forth below:

```
5' cap-GACUCAGACUGACAUUCUU-C3-pi 3'
(sense strand; SEQ ID NO: 16)

5' AAGAAUgUCAGUCUGAGUC-C3-C3 3'
(antisense strand; SEQ ID NO: 29)
``` wherein each of A, U, G and C is an unmodified ribonucleotide;

wherein each of U, G and C is a 2'-O-methyl sugar modified ribonucleotide;

wherein g is a ribonucleotide joined to an adjacent ribonucleotide (5'>3') by a 2'-5' internucleotide phosphate bond;

wherein in the antisense strand and in the sense strand, each consecutive ribonucleotide is joined to the next ribonucleotide by a phosphodiester bond;

wherein the sense strand comprises a 1,3-propanediol, mono (dihydrogen phosphate) (C3) non-nucleotide overhang covalently attached at the 3' terminus of the strand;

wherein the sense strand comprises a 5' cap covalently attached at the 5' terminus of the strand;

wherein the antisense strand comprises a C3-C3 non-nucleotide overhang covalently attached at the 3' terminus of the strand; and wherein the 3' terminus of the sense strand is phosphorylated (pi); or a pharmaceutically acceptable salt of such compound.

According to one embodiment provided is a modified nucleic acid compound having a sense strand and an antisense strand set forth below:

```
5' cap-GACUCAGACUGACAUUCUU-C3-pi 3'
(sense strand; SEQ ID NO: 16)

5' AAGAAuUCAGUCUGAGUC-C3-C3 3'
(antisense strand; SEQ ID NO: 29)
``` wherein each of A, U, G and C is an unmodified ribonucleotide;

wherein each of U, G and C is a 2'-O-methyl sugar modified ribonucleotide;

wherein u is a ribonucleotide joined to an adjacent ribonucleotide (5'>3') by a 2'-5' internucleotide phosphate bond;

wherein in the antisense strand and in the sense strand, each consecutive ribonucleotide is joined to the next ribonucleotide by a phosphodiester bond;

wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' GACUCAGACUGACAUUCUA-dTdT 3'
(sense strand; SEQ ID NO: 16)

5' AAGAAUGUCAGUCUGAGUC-dTdT 3'
(antisense strand; SEQ ID NO: 29)
``` wherein each of A, U, G and C is an unmodified ribonucleotide;
wherein in the antisense strand and in the sense strand, each consecutive ribonucleotide is joined to the next ribonucleotide by a phosphodiester bond;
wherein each of the sense strand and the antisense strand comprises a two nucleotide thymidine-thymidine (dTdT) overhang covalently attached at the 3' terminus of the strand; and
wherein the 3' terminus of the sense strand and of the antisense strand is non-phosphorylated; or
a pharmaceutically acceptable salt of such compound.

According to one embodiment provided is a modified nucleic acid compound having a sense strand and an antisense strand set forth below:

```
5' C3-GACUCAGACUGACAUUCUU-C3-pi 3'
(sense strand; SEQ ID NO: 16)

5' phos-AAGAAUgUCAGUCUGAGUC-C3-C3-pi 3'
(antisense strand; SEQ ID NO: 29)
``` wherein each of A, U, G and C is an unmodified ribonucleotide;
wherein each of U, G and C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand and wherein the overhang is phosphorylated (C3-pi);
wherein the sense strand comprises a C3 5' cap covalently attached at the 5' terminus of the strand;
wherein the antisense strand comprises a C3-C3 non-nucleotide overhang covalently attached at the 3' terminus of the strand; and
wherein in the antisense strand the ribonucleotide at the 5' terminus is phosphorylated (phos) and the overhang at the 3' terminus is phosphorylated (—C3-C3-pi); or
a pharmaceutically acceptable salt of such compound.

According to one embodiment provided is a modified nucleic acid compound having a sense strand and an antisense strand set forth below:

```
5' C3-GACUCAGACUGACAuucuu-C3-pi 3'
(sense strand; SEQ ID NO: 16)

5' phos-AAGAAUgUCAGUCUGAGUC-C3-C3-pi 3'
(antisense strand; SEQ ID NO: 29)
``` wherein each of A, U, G and C is an unmodified ribonucleotide;
wherein each of C is a 2'-O-methyl sugar modified ribonucleotide;
wherein each of u, c and g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand and wherein the overhang is phosphorylated (C3-pi);
wherein the sense strand comprises a C3 5' cap covalently attached at the 5' terminus of the strand;
wherein the antisense strand comprises a C3-C3 non-nucleotide overhang covalently attached at the 3' terminus of the strand; and
wherein in the antisense strand the ribonucleotide at the 5' terminus is phosphorylated (phos) and the overhang at the 3' terminus is phosphorylated (—C3-C3-pi); or
a pharmaceutically acceptable salt of such compound.

According to one embodiment provided is a modified nucleic acid compound having a sense strand and an antisense strand set forth below:

```
5' C3-GACUCAGACUGACAUUCUU-C3-pi 3'
(sense strand; SEQ ID NO: 16)

5' phos-AAGAAUgUCAGUCUGAGUC-C3-C3-pi 3'
(antisense strand; SEQ ID NO: 29)
``` wherein each of A, U, G and C is an unmodified ribonucleotide;
wherein each of U and C is a 2'-O-methyl sugar modified ribonucleotide;
wherein g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand and wherein the overhang is phosphorylated (C3-pi);
wherein the sense strand comprises a C3 5' cap covalently attached at the 5' terminus of the strand;
wherein the antisense strand comprises a C3-C3 non-nucleotide overhang covalently attached at the 3' terminus of the strand; and
wherein in the antisense strand the ribonucleotide at the 5' terminus is phosphorylated (phos) and the overhang at the 3' terminus is phosphorylated (—C3-C3-pi); or
a pharmaceutically acceptable salt of such compound.

According to one embodiment provided is a modified nucleic acid compound having a sense strand and an antisense strand set forth below:

```
5' cap-GGAUGUUUGGGAGAuguau-C3-pi 3'
(sense strand; SEQ ID NO: 18)

5' AUACAUcUCCCAAACAUCC-C3-C3 3'
(antisense strand; SEQ ID NO: 31)
``` wherein each of A, U, G and C is an unmodified ribonucleotide;
wherein each of A, U and C is a 2'-O-methyl sugar modified ribonucleotide;
wherein each of a, u, c and g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGAUGUUUGGGAGAUGUAU-C3-pi 3'
(sense strand; SEQ ID NO: 18)

5' AUACAUcUCCCAAACAUCC-C3-C3 3'
(antisense strand; SEQ ID NO: 31)
``` wherein each of A, U, G and C is an unmodified ribonucleotide;
wherein each of U and C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGGCCUGACUCAGACUGAU-C3-pi 3'
(sense strand; SEQ ID NO: 19)

5' AUCAGUcUGAGUCAGGCCC-C3-C3 3'
(antisense strand; SEQ ID NO: 32)
``` wherein each of A, U, G and C is an unmodified ribonucleotide;
wherein each of U and C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound. According to one embodiment of such compound the 5' cap covalently attached at the 5' terminus of the sense strand is 1,3-propanediol, mono(dihydrogen phosphate) (C3); and in the antisense strand the ribonucleotide at the 5' terminus is phosphorylated (phos) and the overhang at the 3' terminus is phosphorylated (—C3-C3-pi).

According to one embodiment provided is a modified nucleic acid compound having a sense strand and an antisense strand set forth below:

```
5' cap-GGGCCUGACUCAGAcugau-C3-pi 3'
(sense strand; SEQ ID NO: 19)

5' AUCAGuCUGAGUCAGGCCC-C3-C3 3'
(antisense strand; SEQ ID NO: 32)
``` wherein each of A, U, G and C is an unmodified ribonucleotide;
wherein each of U and C is a 2'-O-methyl sugar modified ribonucleotide;
wherein each of a, u, c and g is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGGCCUGACUCAGACUGAU-C3-pi 3'
(sense strand; SEQ ID NO: 19)

5' AUCAGuCUGAGUCAGGCCC-C3-C3 3'
(antisense strand; SEQ ID NO: 32)
``` wherein each of A, U, G and C is an unmodified ribonucleotide;
wherein each of U and C is a 2'-O-methyl sugar modified ribonucleotide;
wherein u is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-GGGCCUGACUCAGACUGAU-C3-pi 3'
(sense strand; SEQ ID NO: 19)

5' AUCAGUcUGAGUCAGGCCC-C3-C3 3'
(antisense strand; SEQ ID NO: 32)
``` wherein each of A, U, G and C is an unmodified ribonucleotide;
wherein each of U and C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' C3-GGGCCUGACUCAGAcugau-C3-pi 3'
(sense strand; SEQ ID NO: 19)

5' phos-AUCAGUcUGAGUCAGGCCC-C3-C3-pi 3'
(antisense strand; SEQ ID NO: 32)
``` wherein each of A, U, G and C is an unmodified ribonucleotide;
wherein each of U and C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand and wherein the overhang is phosphorylated (C3-pi);
wherein the sense strand comprises a C3 5' cap covalently attached at the 5' terminus of the strand;
wherein the antisense strand comprises a C3-C3 non-nucleotide overhang covalently attached at the 3' terminus of the strand; and
wherein in the antisense strand the ribonucleotide at the 5' terminus is phosphorylated (phos) and the overhang at the 3' terminus is phosphorylated (—C3-C3-pi); or
a pharmaceutically acceptable salt of such compound.

According to one embodiment provided is a modified nucleic acid compound having a sense strand and an antisense strand set forth below:

```
5' C3-GGGCCUGACUCAGAcugau-C3-pi 3'
(sense strand; SEQ ID NO: 19)

5' phos-AUCAGUcUGAGUCAGGCCC-C3-C3-pi 3'
(antisense strand; SEQ ID NO: 32)
``` wherein each of A, U, G and C is an unmodified ribonucleotide;
wherein C is a 2'-O-methyl sugar modified ribonucleotide;
wherein c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand and wherein the overhang is phosphorylated (C3-pi);
wherein the sense strand comprises a C3 5' cap covalently attached at the 5' terminus of the strand;
wherein the antisense strand comprises a C3-C3 non-nucleotide overhang covalently attached at the 3' terminus of the strand; and
wherein in the antisense strand the ribonucleotide at the 5' terminus is phosphorylated (phos) and the overhang at the 3' terminus is phosphorylated (C3-C3-pi); or
a pharmaceutically acceptable salt of such compound.

According to one embodiment provided is a modified nucleic acid compound having a sense strand and an antisense strand set forth below:

```
5' C3-GGGCCUGACUCAGACUGAU-C3-pi 3'
(sense strand; SEQ ID NO: 19)

5' phos-AUCAGUcUGAGUCAGGCCC-C3-C3-pi 3'
(antisense strand; SEQ ID NO: 32)
``` wherein each of A, U, G and C is an unmodified ribonucleotide;
wherein each of U and C is a 2'-O-methyl sugar modified ribonucleotide;
wherein c is a ribonucleotide joined to an adjacent ribonucleotide (5'>3') by a 2'-5' internucleotide phosphate bond;

wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand and wherein the overhang is phosphorylated (C3-pi);
wherein the sense strand comprises a C3 5' cap covalently attached at the 5' terminus of the strand;
wherein the antisense strand comprises a C3-C3 non-nucleotide overhang covalently attached at the 3' terminus of the strand; and
wherein in the antisense strand the ribonucleotide at the 5' terminus is phosphorylated (phos) and the overhang at the 3' terminus is phosphorylated (—C3-C3-pi); or
a pharmaceutically acceptable salt of such compound.

According to one embodiment provided is a modified nucleic acid compound having a sense strand and an antisense strand set forth below:

```
5' cap-CAGACCUAUGGAAAcuaca-C3-pi 3'
(sense strand; SEQ ID NO: 20)

5' UGUAGUuUCCAUAGGUCUG-C3-C3 3'
(antisense strand; SEQ ID NO: 19)
``` wherein each of A, U, G and C is an unmodified ribonucleotide;
wherein each of A, U and C is a 2'-O-methyl sugar modified ribonucleotide;
wherein each of 1: and c is a ribonucleotide joined to an adjacent ribonucleotide (5'>3') by a 2'-5' internucleotide phosphate bond;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand;
wherein the sense strand comprises a 5' cap covalently attached at the 5' terminus of the strand;
wherein the antisense strand comprises a C3-C3 non-nucleotide overhang covalently attached at the 3' terminus of the strand; and
wherein the 3' terminus of the sense strand is phosphorylated (pi); or
a pharmaceutically acceptable salt of such compound.

According to one embodiment provided is a modified nucleic acid compound having a sense strand and an antisense strand set forth below:

```
5' cap-CAGACCUAUGGAAACUACA-C3-pi 3'
(sense strand; SEQ ID NO: 20)

5' UGUAGUUUCCAUAGGUCUG-pi 3'
(antisense strand; SEQ ID NO: 33)
``` wherein each of A, U, G and C is an unmodified ribonucleotide;
wherein each of A, U, G and C is a 2'-O-methyl sugar modified ribonucleotide;
wherein in the antisense strand and in the sense strand, each consecutive ribonucleotide is joined to the next ribonucleotide by a phosphodiester bond;
wherein the sense strand comprises a 1,3-propanediol, mono (dihydrogen phosphate) (C3) non-nucleotide overhang covalently attached at the 3' terminus of the strand and wherein the 3' terminus of the sense strand is phosphorylated (pi);
wherein the sense strand comprises a 5' cap covalently attached at the 5' terminus of the strand;
and wherein in the antisense strand the ribonucleotide at the 3' terminus is phosphorylated (pi); or
a pharmaceutically acceptable salt of such compound.

According to one embodiment provided is a modified nucleic acid compound having a sense strand and an antisense strand set forth below:

```
5' cap-CAGACCUAUGGAAACUACA-pi 3'
(sense strand; SEQ ID NO: 20)

5' UGUAGUUUCCAUAGGUCUG 3'
(antisense strand; SEQ ID NO: 33)
``` wherein each of A, U, G and C is an unmodified ribonucleotide;
wherein each of A, U, G and C is a 2'-O-methyl sugar modified ribonucleotide;
wherein in the antisense strand and in the sense strand, each consecutive ribonucleotide is joined to the next ribonucleotide by a phosphodiester bond;
wherein the sense strand comprises a 5' cap covalently attached at the 5' terminus of the strand; and
wherein in the sense strand the ribonucleotide at the 3' terminus is phosphorylated (pi); or
a pharmaceutically acceptable salt of such compound.

In various embodiments of the nucleic acid compounds described herein, supra, the antisense strand comprises a C3-C3 non-nucleotide overhang covalently attached at the 3' terminus of the strand. In some preferred embodiments of the nucleic acid compounds described herein, supra, the C3-C3 non-nucleotide overhang covalently attached at the 3' terminus of the antisense strand is phosphorylated (—C3-C3-pi).

In various embodiments of the nucleic acid compounds described herein the 5' cap is selected from the group consisting of an abasic ribose moiety, an abasic deoxyribose moiety, an inverted deoxyribose moiety, an inverted deoxyabasic moiety (idAb), amino-C6 moiety (AM-c6), C6-amino-pi, a non-nucleotide moiety, a mirror nucleotide, a 5,6,7,8-tetrahydro-2-naphthalene butyric phosphodiester (THNB), a vitamin and a drug moiety.

In various embodiments of the nucleic acid compounds described herein the in the antisense strand the ribonucleotide at the 5' terminus is phosphorylated (phos). In various embodiments of the compounds nucleic acid described herein in the antisense strand the ribonucleotide at the 5' terminus is non-phosphorylated ($).

In another aspect provided are compositions comprising one or more such nucleic acid compounds disclosed herein; and a pharmaceutically acceptable carrier or excipient. In some embodiments the dsRNA molecule is administered as naked dsRNA. In other embodiments the dsRNA molecule is admixed with a pharmaceutically acceptable carrier. In yet other embodiments the dsRNA is encapsulated in a drug carrier.

In another aspect provided is use of the molecules disclosed herein in treating a subject suffering from disease or disorder selected from, without being limited to, alopecia associated with anti-cancer treatment, kidney injury/renal failure, including acute kidney injury, in particular ischemic acute renal failure, and chronic kidney injury; disease or disorder of the inner or middle ear, such as hearing disorder, balance disorder; disease or disorder of the eye, delayed graft function in organ transplant patients, in particular delayed graft function in kidney transplant patients; stroke, brain injury, spinal cord injury, Parkinson's disease, Alzheimer's disease, cardiotoxicity, myocardial infarction/ heart failure. Provided herein are methods for treating or preventing the incidence or severity of such diseases or disorders in a subject in need thereof wherein the diseases or disorders is associated with expression of a p53 gene. Such methods involve administering to a mammal in need of such treatment a prophylactically or therapeutically effective amount of one or more compounds provided herein, which inhibit or reduce expression or activity of the p53 gene.

In some embodiments the at least two dsRNA agents are co-administered, e.g. concomitantly or in sequence. In other embodiments, the at least two dsRNA agents are administered in a pharmaceutical composition comprising a combination thereof.

Provided herein are functional nucleic acids comprising various modifications as disclosed herein, their use for the manufacture of a medicament, pharmaceutical compositions comprising such modified functional nucleic acids and methods for the treatment of a patient suffering from or susceptible to disease or disorder as disclosed herein.

Definitions

For convenience certain terms employed in the specification, examples and claims are described herein.

It is to be noted that, as used herein, the singular forms "a", "an" and "the" include plural forms unless the content clearly dictates otherwise.

Where aspects or embodiments are described in terms of Markush groups or other grouping of alternatives, those skilled in the art will recognize that the disclosure is also thereby described in terms of any individual member or subgroup of members of the group.

An "inhibitor" is a compound, which is capable of reducing (partially or fully) the expression of a gene or the activity of the product of such gene to an extent sufficient to achieve a desired biological or physiological effect. The term "inhibitor" as used herein refers to one or more of an oligonucleotide inhibitor, including, without being limited to siRNA, shRNA, synthetic shRNA; miRNA, antisense RNA and DNA and ribozymes.

A "double-stranded nucleic acid compound" or "dsRNA molecule" or "dsRNA inhibitor" is a compound which is capable of down-regulating or reducing the expression of a gene or the activity of the product of such gene to an extent sufficient to achieve a desired biological or physiological effect and includes one or more of a dsRNA, siRNA, shRNA, synthetic shRNA; miRNA. Inhibition may also be referred to as down-regulation or, for RNAi, silencing.

The term "inhibit" as used herein refers to down-regulating or reducing the expression of a gene or the activity of the product of such gene to an extent sufficient to achieve a desired biological or physiological effect. Inhibition is either complete or partial.

As used herein, the term "down-regulation" or "inhibition" of a target gene means inhibition of the gene expression (transcription or translation) or polypeptide activity of a target gene wherein the target gene is p53 transcribed into an mRNA set forth in any one of SEQ ID NOS:1-7 or an SNP (single nucleotide polymorphism) or other variants thereof. The gi number for the mRNA of each of the transcript variants of human p53 gene is set forth in SEQ ID NOS: 1-7. The polynucleotide sequence of the target mRNA sequence, or the transcript variants refer to the mRNA sequences set forth in SEQ ID NO:1-7, or any homologous sequences thereof, preferably having at least 70% identity, more preferably 80% identity, even more preferably 90% or 95% identity to any one of mRNA set forth in SEQ ID NO:1-7. Therefore, polynucleotide sequences derived from any one of SEQ ID NO:1-7 which have undergone mutations, alterations or modifications as described herein are encompassed in the present disclosure. The terms "mRNA polynucleotide sequence", "mRNA sequence" and "mRNA" are used interchangeably.

As used herein, the terms "oligonucleotide" and "nucleic acid" may be used interchangeably and refer to nucleotide sequences comprising deoxyribonucleic acid (DNA), and ribonucleic acid (RNA). The terms are to be understood to include, as equivalents, analogues of either RNA or DNA made from nucleotide analogues.

"Oligonucleotide" or "oligomer" refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The nucleic acid compounds disclosed herein encompass molecules comprising deoxyribonucleotides, ribonucleotides, modified deoxyribonucleotides, modified ribonucleotides, unconventional moieties and combinations thereof, with the proviso that not each nucleotide is a deoxyribonucleotide.

The term "unconventional moiety" as used herein includes an abasic ribose moiety, an abasic deoxyribose moiety, an unmodified deoxyribonucleotide, a modified deoxyribonucleotide, a mirror nucleotide (L-DNA and L-RNA), a non-base pairing nucleotide analog and a nucleotide joined to an adjacent nucleotide by a 2'-5' internucleotide phosphate bond; C3, C4, C5 and C6 moieties; threose nucleic acids (TNA), pyrazolotriazine (PT) base modified nucleic acid analogs; morpholino; bridged nucleic acids including LNA and ethylene bridged nucleic acids (ENA).

"Substantially complementary" refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly "substantially identical" refers to identity of greater than about 84%, to another sequence.

"Nucleotide" is meant to encompass deoxyribonucleotides and ribonucleotides, which may be natural or synthetic, and or modified or unmodified. Modifications include changes to the sugar moiety, the base moiety and or the linkages between nucleotides in the oligonucleotide.

The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine. In some embodiments one or more nucleotides in an oligonucleotide is substituted with inosine.

According to some embodiments the present disclosure provides inhibitory oligonucleotide compounds comprising unmodified and modified nucleotides and or unconventional moieties. The compound comprises at least one modified nucleotide selected from the group consisting of a sugar modification, a base modification and an internucleotide linkage modification and may contain unconventional moieties such as, without being limited to, a DNA, LNA (locked nucleic acid), ENA (ethylene-bridged nucleic acid), PNA (peptide nucleic acid), arabinoside, phosphonocarboxylate or phosphinocarboxylate nucleotide (PACE nucleotide), mirror nucleotide, or nucleotides with a 6 carbon sugar.

All analogues of, or modifications to, a nucleotide/oligonucleotide are employed with the nucleic acid compounds disclosed herein, provided that said analogue or modification does not substantially adversely affect the function of the nucleic acid compound A sugar modification includes a modification on the 2' moiety of the sugar residue and encompasses amino, fluoro, alkoxy e.g. methoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN, O—, S—, or N-alkyl; O—, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1.

In one embodiment the nucleic acid molecules disclosed herein comprise at least one ribonucleotide comprising a 2' modification on the sugar moiety ("2' sugar modification"). In certain embodiments the compound comprises 2'-O-alkyl or 2'-fluoro or 2'-O-allyl or any other 2' modification, optionally on alternate positions. Other stabilizing modifications are also possible (e.g. terminal modifications). In some embodiments a preferred 2'-O-alkyl is 2'-O-methyl (methoxy) sugar modification.

In some embodiments the backbone of the oligonucleotide is modified and comprises phosphate-D-ribose entities but may also contain thiophosphate-D-ribose entities, triester, thioate, 2'-5' bridged backbone (also may be referred to as 5'-2'), PACE and the like.

As used herein, the terms "non-pairing nucleotide analogue" means a nucleotide analogue which comprises a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analogue is a ribonucleotide. In other embodiments the non-base pairing nucleotide is a deoxyribonucleotide. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to enzymatic degradation and to have extended stability in vivo and in vitro. Other modifications that can be made to oligonucleotides include polymer backbones, cyclic backbones, acyclic backbones, thiophosphate-D-ribose backbones, triester backbones, thioate backbones, 2'-5' bridged backbone, artificial nucleic acids, morpholino nucleic acids, glycol nucleic acid (GNA), threose nucleic acid (TNA), arabinoside, and mirror nucleoside (for example, beta-L-deoxyribonucleoside instead of beta-D-deoxyribonucleoside). Examples of dsRNA molecules comprising LNA nucleotides are disclosed in Elmen et al., (NAR 2005, 33(1):439-447).

The compounds of the present disclosure can be synthesized using one or more inverted nucleotides, for example inverted thymidine or inverted adenine (see, for example, Takei, et al., 2002, JBC 277(26):23800-06).

A "mirror" nucleotide is a nucleotide with reversed chirality to the naturally occurring or commonly employed nucleotide, i.e., a mirror image (L-nucleotide) of the naturally occurring (D-nucleotide), also referred to as L-RNA in the case of a mirror ribonucleotide, and "spiegelmer". The nucleotide can be a ribonucleotide or a deoxyribonucleotide and my further comprise at least one sugar, base and or backbone modification. Examples of mirror nucleotides are disclosed in U.S. Pat. No. 6,586,238. U.S. Pat. No. 6,602,858 discloses nucleic acid catalysts comprising at least one L-nucleotide substitution.

Other modifications include terminal modifications on the 5' and/or 3' part of the oligonucleotides and are also known as capping moieties. Such terminal modifications are selected from a nucleotide, a modified nucleotide, a lipid, a peptide, a sugar and inverted abasic moiety.

In various embodiments of the nucleic acid compounds disclosed herein preferred modifications include incorporation of TNA moieties in the sense strand and or antisense strand. Examples of dsRNA comprising TNA moieties are disclosed in PCT/US11/063365, to the assignee of the present invention. In some embodiments, 1-19 ribonucleotides in the sense strand may be substituted with TNA.

In various embodiments of the nucleic acid compounds disclosed herein preferred modifications include incorporation of pyrazolotriazine base-modified nucleotide moieties in the sense strand and or antisense strand. Examples of pyrazolotriazine moieties and dsRNA comprising pyrazolotriazine moieties are disclosed in PCT/IL2013/050465, co-assigned to the assignee of the present invention. Pyrazolotriazine DNA or RNA analogues are preferably incorporated into a 19-mer antisense strand in positions 1, 5, 6 or 7 (5'>3'). In some embodiments, pyrazolotriazine RNA analogues are preferred. Pyrazolotriazine DNA or RNA analogues may also be covalently attached to the 3' terminus of the sense strand or antisense strand, as 3' terminal overhangs.

The term "conjugate moiety" as used herein refers to a moiety including a peptide, lipid, drug, vitamin, mineral, fluorophore that is capable of being covalently attached to the nucleic acid molecule, preferably at one or more of the 5' terminus or 3' terminus. Without wishing to be bound to theory, the conjugate moiety alters the biodistribution, endosomal escape, cell uptake, plasma retention, targeting of the molecule, without adversely affecting the activity of the nucleic acid molecule. For example, a preferred vitamin is a Vitamin D, Vitamin A or Vitamin E moiety; a preferred lipid is a sphingolipid or cholesterol or cholesterol derivative. An "alkyl moiety or derivative thereof" refers to straight chain or branched carbon moieties and moieties per se or further comprising a functional group including alcohols, phosphodiester, phosphorothioate, phosphonoacetate and also includes amines, carboxylic acids, esters, amides aldehydes.

"Hydrocarbon moiety" and "alkyl moiety" are used interchangeably.

"Terminal functional group" includes halogen, alcohol, amine, carboxylic, ester, amide, aldehyde, ketone, ether groups.

Provided herein are oligonucleotide sequences (SEQ ID NO: 8-33) useful for generation of nucleic acid compounds that target an mRNA transcribed from the p53 gene.

Provided herein are methods and compositions for inhibiting expression of the p53 gene in vitro and in vivo. In general, the in vivo methods includes administering an oligonucleotide compound, in particular a double-stranded nucleic acid compound disclosed herein that target an mRNA transcribed from the p53 gene, or a pharmaceutically acceptable salt of such compound, or a pharmaceutical compositions comprising such compound, or a pharmaceutical compositions comprising a pharmaceutically acceptable salt of such compound, in an amount effective to down-regulate expression of the p53 gene in-vivo. In particular, the in vivo methods disclosed herein are useful for treatment of a disease or a disorder associated with expression of a p53 gene.

In particular, the subject method can be used to inhibit expression of a p53 gene for treatment of a disease or a disorder or a condition, such as, without being limited to, a disease or a disorder or a condition disclosed herein.

Disclosed herein are chemically modified dsRNA compounds, or pharmaceutically acceptable salts of such compounds, which down-regulate the expression of a p53 gene transcribed into mRNA having a polynucleotide sequence set forth in any one of SEQ ID NOS:1-7 and pharmaceutical compositions comprising one or more such compounds or pharmaceutical compositions comprising a pharmaceutically acceptable salt of one or more of such compounds.

According to some embodiments of the nucleic acid compounds disclosed herein, the nucleic acid compound is a duplex oligoribonucleotide in which the sense strand is substantially complementary to an 18-40 consecutive nucleotide segment of the mRNA polynucleotide sequence of a p53 gene, and the antisense strand is substantially complementary to the sense strand. In general, some deviation from the target mRNA sequence is tolerated without compromising the siRNA activity (as described in e.g. Czauderna et al., Nuc. Acids Res. 2003, 31(11):2705-2716). In some embodiment the nucleic acid compound disclosed herein down-regulates p53 gene expression on a post-transcriptional level with or without destroying the mRNA. Without being bound by theory, the nucleic acid compound disclosed herein may target the mRNA for specific cleavage and degradation and/or may inhibit translation from the targeted message.

In some embodiments the double-stranded nucleic acid compound is blunt ended, on one or both ends. More specifically, the double-stranded nucleic acid compound may be blunt ended on the end defined by the 5'-terminus of the first strand and the 3'-terminus of the second strand, or the end defined by the 3'-terminus of the first strand and the 5'-terminus of the second strand.

In other embodiments at least one of the two strands may have an overhang covalently attached at the 3' terminus of the strand in which it is present. Each overhang may independently consist of 1-5 consecutive nucleotides, 1-5 pyrazolotriazine (PT) nucleotide analogues, 1-5 consecutive non-nucleotide moieties or a combination thereof, or a conjugate moiety.

The length of a double-stranded nucleic acid compound duplex is from about 18 to about 40 nucleotides, preferably 19 to 23 nucleotides. Further, each strand (oligomer) may independently have a length selected from the group consisting of about 18 to about 40 bases, preferably 18 to 23 bases and more preferably 19, 20 or 21 nucleotides.

Additionally, in certain preferred embodiments the nucleic acid compound is having a double-stranded structure; wherein the oligonucleotide sequence of one of the strands is selected from one of SEQ ID NOS: 8-20 and wherein the oligonucleotide sequence of the other strand is selected from one of SEQ ID NOS: 21-33; or a pharmaceutically acceptable salt of such compound. In some embodiments complementarity between one of the strands of the nucleic acid compound and the target RNA (SEQ ID NO:1-7) is perfect. In some embodiments one of the strands of the nucleic acid compound is substantially complementary to the target RNA (SEQ ID NO:1-7), i.e. having one, two or up to three mismatches between said strand and the target RNA. In some embodiments, the complementarity between the strands of the double-stranded nucleic acid compound is perfect. In some embodiments, the strands of the double-stranded nucleic acid compound are substantially complementary, i.e. having one, two or up to three mismatches between the strands.

Further, the 5'-terminus of the first strand of the double-stranded nucleic acid compound may be linked to the 3'-terminus of the second strand, or the 3'-terminus of the first strand may be linked to the 5'-terminus of the second strand, said linkage being via a nucleic acid linker typically having a length between 3-100 nucleotides, preferably about 3 to about 10 nucleotides.

The double-stranded nucleic acid compound compounds disclosed herein possess structures and modifications which impart one or more of increased activity, increased stability, reduced toxicity, reduced off target effect, and/or reduced immune response. In preferred embodiments, the double-stranded nucleic acid compound compounds disclosed herein possess structures and modifications which impart increased activity. The double-stranded nucleic acid structures disclosed herein are beneficially applied to double-stranded RNA compounds useful in preventing or attenuation target gene expression, in particular the p53 gene.

In various embodiments the nucleic acid compounds disclosed herein comprise at least one modified nucleotide selected from the group consisting of a sugar modification, a base modification and an internucleotide linkage modification. Accordingly, the chemically modified oligonucleotide compounds disclosed herein may contain modified nucleotides such as DNA, LNA (locked nucleic acid), ENA (ethylene-bridged nucleic acid), PNA (peptide nucleic acid), arabinoside, PACE, mirror nucleoside, or nucleotides with a 6 carbon sugar. Examples of PACE nucleotides and analogues are disclosed in U.S. Pat. Nos. 6,693,187 and 7,067,641 both incorporated herein by reference. The oligonucleotide may further comprise 2'-O-methyl or 2'-fluoro or 2' O-allyl or any other 2' modification, optionally on alternate positions. Other stabilizing modifications, which do not significantly reduce the activity are also possible (e.g. terminal modifications). The backbone of the active part of the oligonucleotide may comprise phosphate-D-ribose entities but may also contain thiophosphate-D-ribose entities, triester, thioate, 2'-5' bridged backbone (also may be referred to as 5'-2'), PACE or any other type of modification. Terminal modifications on the 5' and/or 3' part of the oligonucleotides may be present or absent. Such terminal modifications may be lipids, peptides, sugars, inverted abasic moieties or other molecules.

The present disclosure relates to oligonucleotide sequences (SEQ ID NOS:8-33) useful for generation of nucleic acid compounds which down-regulate expression of the p53 gene, such as novel modified double-stranded nucleic acid compounds described herein. The oligonucleotide sequences of the present invention are beneficially applied to double stranded nucleic acid compounds useful in preventing or attenuating expression of the p53 gene. 21- or 23-mer oligonucleotide sequences can also be generated by 5' and/or 3' extension of the 19-mer sequences disclosed herein. Such extension is preferably complementary to the corresponding p53 mRNA sequence.

Also, disclosed herein is use of nucleic acid compounds in the treatment of various diseases and medical conditions.

Methods, molecules and compositions which down-regulate expression of the p53 gene are disclosed herein and discussed herein at length, and any of said molecule and/or composition are beneficially employed in the treatment of a subject suffering from one or more of said conditions. Particular diseases and medical conditions to be treated are disclosed herein.

dsRNA and RNA Interference

RNA interference (RNAi) is a phenomenon involving double-stranded (ds) RNA-dependent gene-specific post-transcriptional silencing. Initial attempts to study this phenomenon and to manipulate mammalian cells experimentally were frustrated by an active, non-specific antiviral defense mechanism which was activated in response to long dsRNA molecules (Gil et al., Apoptosis, 2000. 5:107-114). Later, it was discovered that synthetic duplexes of 21 nucleotide RNAs could mediate gene specific RNAi in mammalian cells, without stimulating the generic antiviral defense mechanisms Elbashir et al. Nature 2001, 411:494-498 and Caplen et al. PNAS 2001, 98:9742-9747). As a result, small interfering RNAs (siRNAs), which are short double-stranded RNAs, have been widely used to inhibit gene expression and understand gene function.

RNA interference (RNAi) is mediated by small interfering RNAs (siRNAs) (Fire et al, Nature 1998, 391:806) or microRNAs (miRNAs) (Ambros V. Nature 2004, 431:350-355); and Bartel D P. Cell. 2004 116(2):281-97). The corresponding process is commonly referred to as specific post-transcriptional gene silencing when observed in plants and as quelling when observed in fungi.

A siRNA compound is a double-stranded RNA which down-regulates or silences (i.e. fully or partially inhibits) the expression of an endogenous or exogenous gene/mRNA. RNA interference is based on the ability of certain dsRNA species to enter a specific protein complex, where they are then targeted to complementary cellular RNAs and specifically degrades them. Thus, the RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir, et al., Genes Dev., 2001, 15:188). In more detail, longer dsRNAs are digested into short (17-29 bp) dsRNA fragments (also referred to as short inhibitory RNAs or "siRNAs") by type III RNAses (DICER, DROSHA, etc., (see Bernstein et al., Nature, 2001, 409:363-6 and Lee et al., Nature, 2003, 425:415-9). The RISC protein complex recognizes these fragments and complementary mRNA. The whole process is culminated by endonuclease cleavage of target mRNA (McManus and Sharp, Nature Rev Genet, 2002, 3:737-47; Paddison and Hannon, Curr Opin Mol Ther. 2003, 5(3): 217-24). (For additional information on these terms and proposed mechanisms, see for example, Bernstein, et al., RNA. 2001, 7(11):1509-21; Nishikura, Cell. 2001, 107(4): 415-8 and PCT Publication No. WO 01/36646).

The selection and synthesis of dsRNA compounds corresponding to known genes has been widely reported; see for example Ui-Tei et al., J Biomed Biotechnol. 2006; 65052; Chalk et al., BBRC. 2004, 319(1):264-74; Sioud and Leirdal, Met. Mol Biol.; 2004, 252:457-69; Levenkova et al., Bioinform. 2004, 20(3):430-2; Ui-Tei et al., NAR 2004, 32(3):936-48. For examples of the use of, and production of, modified siRNA see Braasch et al., Biochem., 2003, 42(26): 7967-75; Chiu et al., RNA, 2003, 9(9):1034-48; PCT publications WO 2004/015107 (atugen); WO 02/44321 (Tuschl et al), and U.S. Pat. Nos. 5,898,031 and 6,107,094.

Several groups have described the development of DNA-based vectors capable of generating siRNA within cells. The method generally involves transcription of short hairpin RNAs that are efficiently processed to form siRNAs within cells (Paddison et al. PNAS USA 2002, 99:1443-1448; Paddison et al. Genes & Dev 2002, 16:948-958; Sui et al. PNAS USA 2002, 8:5515-5520; and Brummelkamp et al. Science 2002, 296:550-553). These reports describe methods of generating siRNAs capable of specifically targeting numerous endogenously and exogenously expressed genes.

Studies have revealed that siRNA can be effective in vivo in both mammals and humans. Specifically, Bitko et al., showed that specific siRNAs directed against the respiratory syncytial virus (RSV) nucleocapsid N gene are effective in treating mice when administered intranasally (Nat. Med. 2005, 11(1):50-55). For reviews of therapeutic applications of siRNAs see for example Barik (Mol. Med 2005, 83: 764-773) and Chakraborty (Current Drug Targets 2007 8(3):469-82). In addition, clinical studies with short siRNAs that target the VEGFR1 receptor in order to treat age-related macular degeneration (AMD) have been conducted in human patients (Kaiser, Am J Ophthalmol. 2006 142(4): 660-8). Further information on the use of siRNA as therapeutic agents may be found in Durcan, 2008. Mol. Pharma. 5(4):559-566; Kim and Rossi, 2008. BioTechniques 44:613-616; Grimm and Kay, 2007, JCI, 117(12):3633-41.

Chemical Synthesis

The compounds of the present invention can be synthesized by any of the methods that are well-known in the art for synthesis of ribonucleic (or deoxyribonucleic) oligonucleotides. Such synthesis is, among others, described in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Annu. Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et. al., in IRL Press 1989 edited by Oliver R. W. A.; Kap. 7: 183-208.

Other synthetic procedures are known in the art e.g. the procedures as described in Usman et al., 1987, J. Am. Chem. Soc., 109, 7845; Scaringe et al., 1990, NAR., 18, 5433; Wincott et al., 1995, NAR. 23, 2677-2684; and Wincott et al., 1997, Methods Mol. Bio., 74, 59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides of the present invention can be synthesized separately and joined together post-synthetically, for example, by ligation (Moore et al., 1992, Science 256, 9923; Draper et al., International Patent Publication No. WO 93/23569; Shabarova et al., 1991, NAR 19, 4247; Bellon et al., 1997, Nucleosides & Nucleotides, 16, 951; Bellon et al., 1997, Bioconjugate Chem. 8, 204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via tandem synthesis methodology, as described for example in US Patent Publication No. US 2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

The present invention further provides for a pharmaceutical composition comprising two or more nucleic acid molecules for the treatment of any of the diseases and conditions mentioned herein, whereby said two molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. In one embodiment, the nucleic acid molecules are comprised of a double-stranded nucleic acid structure as described herein, wherein the two nucleic acid molecules are selected from the oligonucleotides described herein. Thus, the nucleic acid molecules may be covalently or non-covalently bound or joined by a linker to form a tandem siRNA compound. Such tandem dsRNA molecules comprising two siRNA sequences are typically of 38-150 nucleotides in length, more preferably 38 or 40-60 nucleotides in length, and longer accordingly if more than two siRNA sequences are included in the tandem molecule. A longer tandem compound comprised of two or more longer sequences which encode siRNA produced via internal cellular processing, e.g., long dsRNAs, is also envisaged, as is a tandem molecule encoding two or more shRNAs. Such tandem molecules are also considered to be a part of the disclosure. A compound comprising two (tandem) or more (RNAistar) dsRNA sequences disclosed herein is envisaged. Examples of such "tandem" or "star" molecules are provided in PCT patent publication no. WO 2007/091269, assigned to the assignee of the present application and incorporated herein by reference in its entirety.

The nucleic acid molecules that target p53 may be the main active component in a pharmaceutical composition, or may be one active component of a pharmaceutical composition containing two or more nucleic acid (or molecules which encode or endogenously produce two or more nucleic acids, be it a mixture of molecules or one or more tandem molecules which encode two or more nucleic acid compounds), said pharmaceutical composition further being comprised of one or more additional nucleic acid molecule which targets one or more additional gene. Simultaneous inhibition of said additional gene(s) will likely have an additive or synergistic effect for treatment of the diseases disclosed herein.

Additionally, the nucleic acid disclosed herein or any nucleic acid molecule comprising or encoding such nucleic acid can be linked or bound (covalently or non-covalently) to antibodies (including aptamer molecules) against cell surface internalizable molecules expressed on the target cells, in order to achieve enhanced targeting for treatment of the diseases disclosed herein. For example, anti-Fas antibody (preferably a neutralizing antibody) may be combined (covalently or non-covalently) with any dsRNA. In another example, an aptamer which can act like a ligand/antibody may be combined (covalently or non-covalently) with any nucleic acid compounds.

The nucleic acid molecules disclosed herein can be delivered either directly or with viral or non-viral vectors. When delivered directly, the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell. Vectors optionally used for delivery of the compounds of the present invention are commercially available, and may be modified for the purpose of delivery of the compounds of the present invention by methods known to one of skill in the art.

Chemical Modifications

All analogs of, or modifications to, a nucleotide/oligonucleotide may be employed with the present invention, provided that said analogue or modification does not substantially affect the function of the nucleotide/oligonucleotide. The nucleotides can be selected from naturally occurring or synthetic modified bases. Naturally occurring bases include adenine, guanine, cytosine, thymine and uracil. Modified bases of nucleotides are described herein.

In addition, analogues of polynucleotides can be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to enzymatic degradation and to have extended stability in vivo and in vitro. Other modifications that can be made to oligonucleotides include polymer backbones, cyclic backbones, acyclic backbones, thiophosphate-D-ribose backbones, triester backbones, thioate backbones, 2'-5' bridged backbone, artificial nucleic acids, morpholino nucleic acids, locked nucleic acid (LNA), glycol nucleic acid (GNA), threose nucleic acid (TNA), arabinoside, and mirror nucleoside (for example, beta-L-deoxynucleoside instead of beta-D-deoxynucleoside). Examples of dsRNA molecules comprising LNA nucleotides are disclosed in Elmen et al., (NAR 2005, 33(1):439-447).

The nucleic acid compounds of the present invention can be synthesized using one or more inverted nucleotides, for example inverted thymidine or inverted adenine (see, for example, Takei, et al., 2002, JBC 277(26):23800-06).

The term "unconventional moiety" as used herein refers to abasic ribose moiety, an abasic deoxyribose moiety, a deoxyribonucleotide, a modified deoxyribonucleotide, a mirror nucleotide, a threose nucleic acid (TNA), a pyrazolotriazine (PT) nucleotide analogue, a non-base pairing nucleotide analog and a nucleotide joined to an adjacent nucleotide by a 2'-5' internucleotide phosphate bond; C3, C4, C5 and C6 moieties; bridged nucleic acids including LNA and ethylene bridged nucleic acids.

The terms "cap" or "capping moiety" as used herein includes abasic ribose moiety, abasic deoxyribose moiety, modifications of abasic ribose and abasic deoxyribose moieties including 2' O alkyl modifications; inverted abasic ribose, inverted abasic deoxyribose moieties (idAb) and modifications thereof; amino-C6 moiety (AM-c6), C6-imino-Pi; a non-nucleotide moiety, a mirror nucleotide including L-DNA and L-RNA; 5' OMe nucleotide; a 5,6,7,8-tetrahydro-2-naphthalene butyric phosphodiester (THNB), a vitamin, a drug moiety and a nucleotide analogue including, without being limited to, a 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyriboabasic 5'-phosphate.

A "mirror" nucleotide is a nucleotide with reversed chirality to the naturally occurring or commonly employed nucleotide, i.e., a mirror image (L-nucleotide) of the naturally occurring (D-nucleotide). The nucleotide can be a ribonucleotide or a deoxyribonucleotide and may further comprise at least one sugar, base and/or backbone modification. U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU).

Useful pyrazolotriazine (PT) nucleotide analogues are described by the general formula I:

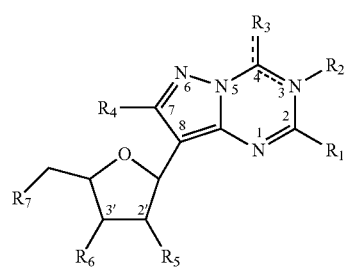

(I)

wherein
$R_1$ and $R_4$ each independently is selected from H, halogen, —CN, —SCN, —NO$_2$, —O-hydrocarbyl, —S— hydrocarbyl, —CO—H, —CO-hydrocarbyl, —NR$_8$R$_9$, heteroaryl, or hydrocarbyl optionally substituted by one or more groups each independently is halogen, —CN, —SCN, or —NO$_2$, wherein R$_8$ and R$_9$ are each independently H, hydrocarbyl, or an amine protecting group; or R$_8$ and R$_9$ together with the nitrogen atom to which they are attached form a saturated or unsaturated heterocyclic ring optionally containing 1-2 further heteroatoms selected from oxygen, nitrogen or sulfur;
$R_2$ is H or absent;
$R_3$ is O or —NR$_{10}$R$_{10'}$, wherein R$_{10}$ and R$_{10'}$ are each independently H, hydrocarbyl, —CO— hydrocarbyl, or an amine protecting group; and
$R_5$ is H, halogen, —O$^-$, or —OR$_{11}$;
$R_6$ is —O$^-$, or —OR$_{11}$;
$R_7$ is —OR$_{11}$, or a phosphate moiety;
$R_{11}$ each independently is H, (C$_1$-C$_8$)alkyl, (C$_1$-C$_8$)alkylene-OR$_{12}$, (C$_1$-C$_8$)alkylene-SR$_{12}$, (C$_1$-C$_8$)alkylene-NR$_{12}$R$_{13}$, a hydroxyl protecting group, or a phosphoramidite moiety of the formula —P(OR$_{14}$)NR$_{15}$R$_{16}$, wherein R$_{14}$ is H or cyano-(C$_1$-C$_8$)alkyl, preferably cyanoethyl, and R$_{15}$ and R$_{16}$ each independently is H or (C$_1$-C$_8$)alkyl, preferably isopropyl;
$R_{12}$ and $R_{13}$ each independently is H or (C$_1$-C$_8$)alkyl; and
the dotted line represents a potential double bond between the carbon atom at position 4 and either the nitrogen atom at position 3 or the residue R$_3$, provided that, when R$_2$ is H, there is a double bond between the carbon atom at position 4 and R$_3$, and when R$_2$ is absent, there is a double bond between the carbon atom at position 4 and the nitrogen atom at position 3, but excluding the analogues wherein R$_5$ and R$_6$ each independently is —OH or —O$^-$, and the analogues wherein R$_5$ is H and R$_1$ is hydrocarbyl.

In various embodiments provided herein is a double-stranded nucleic acid molecule comprising a PT nucleotide analog of the general formula II:

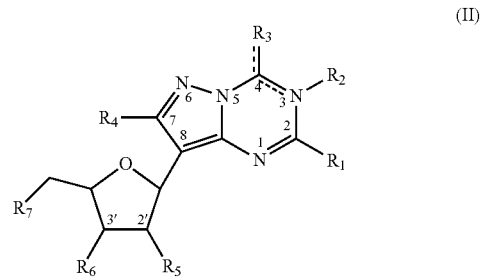

(II)

wherein
$R_1$ and $R_4$ each independently is selected from H, halogen, —CN, —SCN, —NO$_2$, —O-hydrocarbyl, —S— hydrocarbyl, —CO—H, —CO-hydrocarbyl, —NR$_8$R$_9$, heteroaryl, or hydrocarbyl optionally substituted by one or more groups each independently a halogen, —CN, —SCN, or —NO$_2$, wherein R$_8$ and R$_9$ are each independently H or hydrocarbyl, or R$_8$ and R$_9$ together with the nitrogen atom to which they are attached form a saturated or unsaturated heterocyclic ring optionally containing 1-2 further heteroatoms selected from oxygen, nitrogen or sulfur;
$R_2$ is H or absent;
$R_3$ is O or —NR$_{10}$R$_{10'}$, wherein R$_{10}$ and R$_{10'}$ are each independently H, hydrocarbyl or —CO— hydrocarbyl;
$R_5$ is H, halogen, —O$^-$ or —OR$_{11}$;
$R_6$ is —O$^-$ or —OR$_{11}$,
$R_7$ is OR$_{11}$, a monophosphate moiety or a phosphate linking moiety; and
$R_{11}$ each independently is H, (C$_1$-C$_8$)alkyl, (C$_1$-C$_8$)alkylene-OR$_{12}$, (C$_1$-C$_8$)alkylene-SR$_{12}$, or (C$_1$-C$_8$)alkylene-NR$_{12}$R$_{13}$, wherein R$_{12}$ and R$_{13}$ each independently is H or (C$_1$-C$_8$) alkyl; and the dotted line represents a potential double bond between the carbon atom at position 4 and either the nitrogen atom at position 3 or the radical $R_3$, provided that when $R_2$ is H, there is a double bond between the carbon atom at position 4 and $R_3$, and when $R_2$ is absent, there is a double bond between the carbon atom at position 4 and the nitrogen atom at position 3.

In some embodiments the PT nucleotide analogue comprises an adenine PT nucleotide analogue of Formula IIa, or a guanine PT nucleotide analogue of Formula IIb, as follows in Table I:

TABLE I

Adenine and guanine PT nucleotide analogues of formulas IIa and IIb:

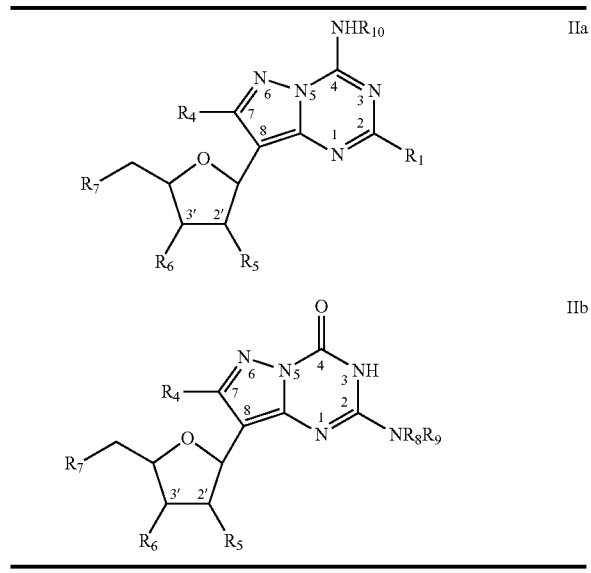

In some preferred embodiments the pyrazolotriazine (PT) nucleotide analogue is an adenine PT nucleotide analogue of formula IIa (i.e. $R_2$ is absent and $R_3$ is $NHR_{10}$) wherein $R_1$ is H, $R_{10}$ is H; $R_4$ is H; $R_5$ is H, halogen or $-OR_{11}$, wherein $R_{11}$ is H, $(C_1-C_8)$alkyl, $(C_1-C_8)$alkylene-$OR_{12}$, $(C_1-C_8)$alkylene-$SR_{12}$, or $(C_1-C_8)$alkylene-$NR_{12}R_{13}$, wherein $R_{12}$ and $R_{13}$ each is independently H or $(C_1-C_8)$alkyl; $R_6$ is $-O^-$ or $-OH$; and $R_7$ is OH or a phosphate linking moiety. In some embodiments $R_{11}$ is H, $CH_3$ or $(CH_2)_2-OCH_3$. In some embodiments $R_{11}$ is H (i.e. $R_5$ is hydroxy; 2'OH). In some embodiments $R_{11}$ is $CH_3$ (i.e. $R_5$ is methoxy, 2'OMe). In some embodiments $R_{11}$ is $(CH_2)_2-OCH_3$ (i.e. $R_5$ is methoxyethoxy; 2'MOE).

In some preferred embodiments the pyrazolotriazine (PT) nucleotide analogue is a deoxyadenosine PT nucleotide analogue of formula IIa wherein $R_1$ is H, $R_{10}$ is H; $R_4$ is H; $R_5$ is H or halogen; $R_6$ is $-O^-$ or $-OH$; and $R_7$ is OH or a phosphate moiety. In some embodiments $R_5$ is H. In some embodiments $R_5$ is halogen, preferably fluoro (F).

In some preferred embodiments the pyrazolotriazine (PT) nucleotide analogue is a guanosine PT nucleotide analogue of formula IIb wherein each of $R_4$, $R_8$ and $R_9$ is H, $R_5$ is $-OR_{11}$, wherein $R_{11}$ is H, $(C_1-C_8)$alkyl, $(C_1-C_8)$alkylene-$OR_{12}$, $(C_1-C_8)$alkylene-$SR_{12}$, or $(C_1-C_8)$alkylene-$NR_{12}R_{13}$, wherein $R_{12}$ and $R_{13}$ each is independently H or $(C_1-C_8)$ alkyl; $R_6$ is $-O^-$ or $-OH$; and $R_7$ is OH or a phosphate moiety. In some embodiments $R_{11}$ is H, $CH_3$ or $(CH_2)_2-OCH_3$. In some embodiments $R_{11}$ is H (i.e. $R_5$ is hydroxy; 2'OH). In some embodiments $R_{11}$ is $CH_3$ (i.e. $R_5$ is methoxy, 2'-OMethyl). In some embodiments $R_{11}$ is $(CH_2)_2-OCH_3$ (i.e. $R_5$ is methoxyethoxy; 2'MOE).

In some preferred embodiments the pyrazolotriazine (PT) nucleotide analogue is a deoxyguanosine PT nucleotide analogue of formula IIb (i.e. $R_2$ is H and $R_3$ is O) wherein each of $R_4$, $R_8$ and $R_9$ is H, $R_5$ is H, halogen or $-OR_{11}$; $R_6$ is $-O^-$ or $-OH$; and $R_7$ is OH or a phosphate linking moiety. In some embodiments $R_5$ is H. In some embodiments $R_5$ is halogen, preferably fluoro (F).

In some embodiments of the nucleic acid compounds disclosed herein the backbone of the oligonucleotides is modified and comprises phosphate-D-ribose entities but may also contain thiophosphate-D-ribose entities, triester, thioate, 2'-5' bridged backbone (also may be referred to as 2'5' linked nucleotide or 5'-2'), PACE and the like. Additional modifications include reversible or labile phosphotriester linkages such as those disclosed in US20090093425 and US20110294869, respectively.

In various embodiments of the nucleic acid compounds disclosed (Structures A1 and A2) herein the covalent bond joining each consecutive N or N' to the adjacent N or N' is a phosphodiester bond.

In some embodiments of the nucleic acid compounds disclosed herein (Structures A, A1 and A2) the sense strand is either phosphorylated or non-phosphorylated at both the 3' terminus and the 5' terminus. In some embodiments of the nucleic acid compounds disclosed herein (Structures A, A1 and A2) the antisense strand is either phosphorylated or non-phosphorylated at both the 3' terminus and the 5' terminus. In some embodiments of the nucleic acid compounds disclosed herein (Structures A, A1 and A2) the ribonucleotide at the 3' terminus and at the 5' terminus in each of the antisense strand and the sense strand is phosphorylated. In some embodiments of the nucleic acid compounds disclosed herein (Structures A, A1 and A2) the ribonucleotide at the 3' terminus and at the 5' terminus in each of the antisense strand and the sense strand is non-phosphorylated. In some embodiments of the nucleic acid compounds disclosed herein (Structures A, A1 and A2) in each of the antisense strand and the sense strand the ribonucleotide at the 3' terminus is phosphorylated and the ribonucleotide at the 5' terminus is non-phosphorylated.

In some embodiments of the nucleic acid compounds disclosed herein (Structures A, A1 and A2) the modified ribonucleotide comprises a modification at the 2' position of the sugar moiety. In some embodiments of the nucleic acid compounds disclosed herein (Structures A, A1 and A2) the modified ribonucleotide is a 2'-O-methyl sugar modified ribonucleotide.

In some embodiments of the nucleic acid compounds disclosed herein (Structures A, A1 and A2) the unconventional moiety is selected from a mirror nucleotide, a threose nucleic acid (TNA), a pyrazolotriazine (PT) nucleotide analogue and a ribonucleotide joined to an adjacent ribonucleotide by a 2'-5' internucleotide phosphate bond.

In some embodiments of the nucleic acid compounds disclosed herein (Structures A, A1 and A2) the unconventional moiety is a nucleotide analogue. In some embodiments of the nucleic acid compounds disclosed herein (Structures A, A1 and A2) the unconventional moiety is a pyrazolotriazine (PT) nucleotide analogue. In some preferred embodiments of the nucleic acid compounds disclosed herein (Structures A, A1 and A2) a pyrazolotriazine (PT) nucleotide analogue is present. In some preferred embodiments of the nucleic acid compounds disclosed herein (Structures A, A1 and A2) the pyrazolotriazine (PT) nucleotide analogue is present only in the antisense strand.

In some preferred embodiments of the nucleic acid compounds disclosed herein the pyrazolotriazine (PT) nucleotide analogue is present in the antisense strand once in one of positions 4-7 (5'>3'). In some preferred embodiments of the nucleic acid compounds disclosed herein the pyrazolotriazine (PT) nucleotide analogue is present in the antisense strand twice: at position 1 (5'>3') and at one of positions 4, 5, 6 or 7 (5'>3'). In various embodiments of the nucleic acid compounds disclosed herein the pyrazolotriazine (PT) nucleotide analogue is present in the antisense strand and in one or in both of the overhangs (Z and/or Z') that are covalently attached at the 3' terminus of the strand in which the overhang is present.

In various embodiments of the nucleic acid compounds described herein, overhang (Z or Z') is independently present or absent, but if present is covalently attached at the 3' terminus of the strand in which it is present. In various embodiments the overhang (Z or Z') independently comprises 1-5 consecutive nucleotides, pyrazolotriazine (PT) nucleotide analogues or consecutive non-nucleotide moieties or a combination thereof, or a vitamin, or a drug moiety, covalently attached at the 3' terminus of the strand in which it is present. In some embodiments of the nucleic acid compounds disclosed herein both overhangs (Z and Z') are absent. In other embodiments Z or Z' is present.

In some embodiments of the nucleic acid compounds disclosed herein, Z and/or Z' is 1-5 consecutive nucleotides. In some embodiments each nucleotide is a dT, and each of Z and Z' is 2 consecutive nucleotides (dTdT).

In some embodiments of the nucleic acid compounds disclosed herein, Z and/or Z' is 1-5 consecutive non-nucleotide moieties. In some embodiments each of Z and/or Z' independently includes a non-nucleotide moiety, such as C2, C3, C4, C5 or C6 alkyl moiety, optionally a C3 1,3-Propanediol, mono(dihydrogen phosphate) (C3) [CAS RN: 13507-42-1] or a derivative thereof including propanol (C3-OH/C3OH), propanediol, and phosphodiester derivative of propanediol ("C3Pi"). In some embodiments each of Z and/or Z' includes two hydrocarbon moieties and in some examples is C3Pi-C3OH or C3Pi-C3Pi. Each C3 is covalently conjugated to an adjacent C3 via a covalent bond, preferably a phospho-based bond. In some embodiments the phospho-based bond is a phosphorothioate, a phosphonoacetate or a phosphodiester bond.

In some embodiments of the nucleic acid compounds disclosed herein, each of Z and Z' is a 1-2 consecutive non-nucleotide moieties. In some preferred embodiments each non-nucleotide moiety is a 1,3-Propanediol, mono(dihydrogen phosphate) (C3). In some preferred embodiments of the nucleic acid compounds disclosed herein Z is one C3 non-nucleotide moiety (C3) and Z' is two consecutive C3 non-nucleotide moieties (C3-C3).

In some embodiments of the nucleic acid compounds disclosed herein (Structures A, A1 and A2) the cap (z") is absent.

In some embodiments of the nucleic acid compounds disclosed herein (Structures A, A1 and A2) the cap, wherein z" is present. In some embodiments of the nucleic acid compounds disclosed herein (Structures A, A1 and A2) the cap z" is selected from the group consisting of an abasic ribose moiety, an abasic deoxyribose moiety, an inverted abasic ribose moiety, an inverted deoxyribose moiety, an inverted deoxyabasic moiety (idAb), amino-C6 moiety (AM-c6), C6-amino-Pi, a non-nucleotide moiety, a mirror nucleotide, a 5,6,7,8-tetrahydro-2-naphthalene butyric phosphodiester (THNB), a vitamin and a drug moiety. In some embodiments of the nucleic acid compounds disclosed herein (Structures A, A1 and A2) the cap z" is a 1,3-Propanediol, mono(dihydrogen phosphate) (C3). In some embodiments of the nucleic acid compounds disclosed herein (Structures A, A1 and A2), each of N, N', N1 and N2 is an unmodified ribonucleotide, z" is absent, Z and Z' are present and consist of dTdT overhang. In some embodiments of Structure A1 x=y=19 and Z comprises at least one $C_3$ alkyl overhang. In specific embodiments of Structure A2 x=y=18 and Z comprises at least one $C_3$ alkyl overhang. In some embodiments the $C_3$-$C_3$ overhang is covalently attached to the 3' terminus of (N)x or (N')y via a covalent linkage, preferably a phosphodiester linkage. In some embodiments the linkage between a first $C_3$ and a second C3 is a phosphodiester linkage. In some embodiments the 3' non-nucleotide overhang is C3Pi-C3Pi. In some embodiments the 3' non-nucleotide overhang is C3Pi-C3Ps. In some embodiments the 3' non-nucleotide overhang is C3Pi-C3OH (OH is hydroxy). In some embodiments the 3' non-nucleotide overhang is C3Pi-C3OH.

In various embodiments the alkyl moiety comprises an alkyl derivative including a C3 alkyl, C4 alkyl, C5 alkyl or C6 alkyl moiety comprising a terminal hydroxyl, a terminal amino, or terminal phosphate group. In some embodiments the alkyl moiety is a C3 alkyl or C3 alkyl derivative moiety. In some embodiments the C3 alkyl moiety comprises propanol, propylphosphate, propylphosphorothioate or a combination thereof. The C3 alkyl moiety is covalently linked to the 3' terminus of (N')y and/or the 3' terminus of (N)x via a phosphodiester bond. In some embodiments the alkyl moiety comprises propanol, propyl phosphate or propyl phosphorothioate.

In some embodiments each of Z and Z' is independently selected from propanol, propyl phosphate propyl phosphorothioate, combinations thereof or multiples thereof in particular 2 or 3 covalently linked propanol, propyl phosphate, propyl phosphorothioate or combinations thereof. In some embodiments each of Z and Z' is independently selected from propyl phosphate, propyl phosphorothioate, propyl phospho-propanol; propyl phospho-propyl phosphorothioate; propylphospho-propyl phosphate; (propyl phosphate)3, (propyl phosphate)2-propanol, (propyl phosphate)2-propyl phosphorothioate. Any propane or propanol conjugated moiety can be included in Z or Z'.

The structures of exemplary 3' terminal non-nucleotide moieties are as follows:

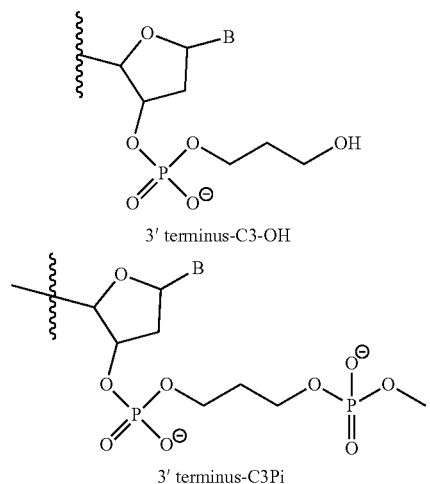

3' terminus-C3-OH

3' terminus-C3Pi

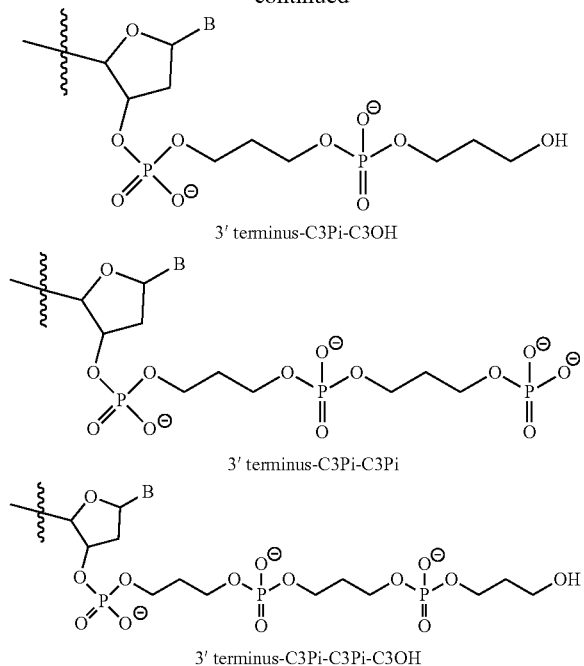

3' terminus-C3Pi-C3OH

3' terminus-C3Pi-C3Pi

3' terminus-C3Pi-C3Pi-C3OH

Phenyl Hydrocarbyl Conjugate

In some embodiments provided are nucleic acid molecules covalently bound to a phenyl hydrocarbyl moiety (PHM). In some embodiments provided are nucleic acid molecules comprising a sense and antisense strand, wherein at least one strand is covalently bound to a phenyl hydrocarbyl moiety (PHM).

In some embodiments a double-stranded nucleic acid disclosed herein comprises a sense strand and an antisense strand, wherein the sense strand, the antisense strand or both are covalently bound directly or via a linker to a moiety comprising a phenyl hydrocarbonyl group, the moiety represented by the general formula I:

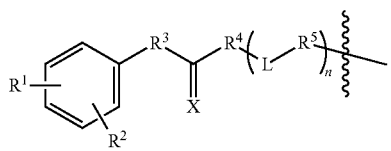

I wherein
$R^1$ and $R^2$ each is independently selected from the group consisting of H, halogen, C1-C10 hydrocarbyl group, $OR^6$, $OCOR^6$, $COOR^6$, $CH_2OR^6$, CHO, $COR^6$, $NR^6R^7$ and $SR^6$;
or $R^1$ and $R^2$ form a saturated or unsaturated cyclic C1-C7 hydrocarbyl ring optionally interrupted by up to 2 heteroatoms selected from oxygen, nitrogen or sulfur and is optionally substituted by up to 3 groups independently selected from the group consisting of halogen, C1-C3 hydrocarbyl group, $OR^6$, $OCOR^6$, $COOR^6$, $CH_2OR^6$, CHO, $COR^6$, $NR^6R^7$, $SR^6$, =O, =S and =NH;
$R^3$ is a C1-C8 hydrocarbyl group optionally interrupted by up to 2 heteroatoms selected from oxygen, nitrogen or sulfur;
$R^4$ is NH, O, S or $CR^6R^7$;
$R^6$ and $R^7$ are each independently selected from the group consisting of H and a C1-C4 hydrocarbyl group;

X is O or S;
L is selected from the group consisting of a peptidyl chain of up to 12 amino acid residues, —[$CH_2$—$CH_2$—O]$_m$—, a C1-C12 hydrocarbyl group optionally interrupted by up to 2 heteroatoms selected from O, N or S and $R^8O$—;
$R^8$ is a $C_1$-$C_{12}$ hydrocarbyl group optionally interrupted by up to 2 heteroatoms selected from 0, N or S;
n is an integer of 0 to 10;
m is an integer of 1 to 10;
$R^5$ is selected from the group consisting of —P(O)($R^9$)—O—, —C(O)NH—, —O—; —NH—, —S—, —C(O)—; —C(O)O—; —NHCS—; —NHCO— and a single bond;
$R^9$ is selected from the group consisting of O⁻, S⁻, $BH_3^-$, $NR^6R^7$ or $CH_3$;
or a pharmaceutically acceptable salt thereof;
wherein the sense strand has sequence identity to the segment of a mRNA corresponding to a p53 gene (SEQ ID NOS:1-7).

Indications

Inhibition of expression of a p53 gene, was shown to be beneficial in treatment and/or prevention of various diseases and disorders. The present application relates in particular to double-stranded nucleic acid molecules which down-regulate expression of the p53 gene, and to the use of these molecules in the treatment and/or prevention of various diseases and disorders. Examples of such diseases/disorders include, without being limited to, ischemia-reperfusion injury, a hearing impairment, a hearing disorder, a balance impairment, a hearing loss, chemotherapy-induced alopecia, radiation therapy-induced alopecia, an acute renal failure, an acute kidney injury, a chronic kidney disease (CKD), a side effect associated with anti-cancer therapy, Delayed Graft Function (DGF) in a kidney transplant patient, a spinal cord injury, a brain injury, a seizure, a stroke, Parkinson's disease, Alzheimer's disease, a tumor, a burn, a wound, hyperthermia, hypoxia, ischemia, organ transplantation, bone marrow transplantation (BMT), myocardial infarction/heart attack, cardiotoxicity and acute liver failure.

In one embodiment the disorder is a side effect associated with anti-cancer therapy and the nucleic acid compound disclosed herein, or the pharmaceutically acceptable salt of such compound, or the composition comprising such compound, or the composition comprising the pharmaceutically acceptable salt of such compound, is administered in an amount effective to treat or ameliorate the side effect. Such anti-cancer therapy may comprise radiation therapy, chemotherapy, molecularly targeted and biological anti-cancer therapy. In various embodiments a side effect associated with such anti-cancer therapy is selected from one or more of hair loss (alopecia), testicular cell damage, intestinal epithelia cell damage, lymphoid system damage, or hemopoietic system damage.

In one embodiment the diseases is a p53-positive cancer and the nucleic acid compound disclosed herein, or the pharmaceutically acceptable salt of such compound, or the composition comprising such compound, or the composition comprising the pharmaceutically acceptable salt of such compound, is administered in an amount effective to down-regulate expression of a p53 gene and thereby sensitize the p53-positive cancer to chemotherapy in the subject.

In one embodiment the nucleic acid compound disclosed herein, or a pharmaceutically acceptable salt of such compound, or a composition comprising such compound, or a composition comprising the pharmaceutically acceptable salt of such compound, is for use in hematopoietic progenitor expansion or in stimulation of hematopoiesis.

In one embodiment the nucleic acid compound disclosed herein, or a pharmaceutically acceptable salt of such compound, or a composition comprising such compound, or a composition comprising the pharmaceutically acceptable salt of such compound, is for use in homing of p53-null Hematopoietic Stem Cell (HSC).

Pharmaceutical Compositions

Provided are compositions and methods for down-regulation of p53 expression by using nucleic acid molecules, such as short interfering nucleic acid (siNA), interfering RNA (RNAi), short interfering RNA (siRNA), double-stranded RNA (dsRNA), micro-RNA (miRNA), and short hairpin RNA (shRNA) molecules capable of mediating down-regulation of p53 gene expression or that mediate RNA interference against p53 gene expression.

While it may be possible for the molecules disclosed herein to be administered as the raw chemical, or a pharmaceutically acceptable salt thereof, it is preferable to present them as a pharmaceutical composition. Accordingly provided is a pharmaceutical composition comprising one or more of the nucleic acid molecules disclosed herein; or a pharmaceutically acceptable salt thereof, and a pharmaceutically acceptable carrier. Such pharmaceutical composition may comprise a mixture of two or more different nucleic acid compounds.

Compositions, methods and kits provided herein may include one or more nucleic acid molecules and methods that independently or in combination modulate (e.g., down-regulate) the expression of p53 protein and/or gene encoding p53 protein. The description of the various aspects and embodiments is provided with reference to p53 gene. However, the various aspects and embodiments are also directed to other related genes, such as homolog genes and transcript variants, and polymorphisms (e.g., single nucleotide polymorphism, (SNPs)) associated with certain p53 gene. As such, the various aspects and embodiments are also directed to other genes that are involved in p53 mediated pathways of signal transduction or gene expression that are involved, for example, in the maintenance or development of diseases, traits, or conditions described herein. These additional genes can be analyzed for target sites using the methods described for the p53 gene herein. Thus, the down-regulation of other genes and the effects of such modulation of the other genes can be performed, determined, and measured as described herein.

Further provided is a pharmaceutical composition comprising at least one nucleic acid compound disclosed herein covalently or non-covalently bound to one or more nucleic acid compounds disclosed herein in an amount effective to down regulate p53 expression; and a pharmaceutically acceptable carrier. The compound may be processed intracellularly by endogenous cellular complexes to produce one or more oligoribonucleotides disclosed herein.

Further provided is a pharmaceutical composition comprising a pharmaceutically acceptable carrier and one or more of the compounds disclosed herein in an amount effective to down-regulate expression in a cell of human p53, the compound comprising a sequence set forth in SEQ ID NOS:8-33

In one embodiment the oligoribonucleotide compounds, compositions and methods disclosed herein inhibit/down-regulate the p53 gene, whereby the inhibition/down-regulation is selected from the group comprising inhibition/down-regulation of gene function, inhibition/down-regulation of polypeptide and inhibition/down-regulation of mRNA expression.

In one embodiment, a nucleic acid disclosed herein may be used to inhibit the expression of the p53 gene family where the genes or gene family sequences share sequence homology. Such homologous sequences can be identified as is known in the art, for example using sequence alignments. Nucleic acid molecules can be designed to target such homologous sequences, for example using perfectly complementary sequences or by incorporating non-canonical base pairs, for example mismatches and/or wobble base pairs, that can provide additional target sequences. In instances where mismatches are identified, non-canonical base pairs (for example, mismatches and/or wobble bases) can be used to generate nucleic acid molecules that target more than one gene sequence. In a non-limiting example, non-canonical base pairs such as UU and CC base pairs are used to generate nucleic acid molecules that are capable of targeting sequences for differing p53 targets that share sequence homology. As such, one advantage of using nucleic acid compounds disclosed herein is that a single nucleic acid can be designed to include nucleic acid sequence that is complementary to the nucleotide sequence that is conserved between the homologous genes. In this approach, a single nucleic acid can be used to inhibit expression of more than one gene instead of using more than one nucleic acid molecule to target the different genes.

Nucleic acid molecules may be used to target conserved sequences corresponding to a gene family or gene families such as p53 family genes. As such, nucleic acid molecules targeting multiple p53 targets can provide increased therapeutic effect. In addition, nucleic acid can be used to characterize pathways of gene function in a variety of applications. For example, nucleic acid molecules can be used to inhibit the activity of target gene(s) in a pathway to determine the function of uncharacterized gene(s) in gene function analysis, mRNA function analysis, or translational analysis. The nucleic acid molecules can be used to determine potential target gene pathways involved in various diseases and conditions toward pharmaceutical development. The nucleic acid molecules can be used to understand pathways of gene expression involved in various diseases and conditions.

In one embodiment the nucleic acid compounds, compositions and methods provided herein, inhibit the p53 polypeptide, whereby the inhibition is selected from the group comprising inhibition of function (which may be examined by an enzymatic assay or a binding assay with a known interactor of the native gene/polypeptide, inter alia), down-regulation of protein or inhibition of protein (which may be examined by Western blotting, ELISA or immuno-precipitation, inter alia) and inhibition of mRNA expression (which may be examined by Northern blotting, quantitative RT-PCR, in-situ hybridisation or microarray hybridisation, inter alia).

In one embodiment, the compositions and methods provided herein include a nucleic acid molecule having RNAi activity against p53 RNA, where the nucleic acid molecule includes a sequence complementary to any RNA having p53 encoding sequence, such as that sequence set forth in SEQ ID NO: 1-7. In another embodiment, a nucleic acid molecule may have RNAi activity against p53 RNA, where the nucleic acid molecule includes a sequence complementary to an RNA having variant p53 encoding sequence, for example other mutant p53 gene not shown in SEQ ID NO: 1-7 but known in the art to be associated with the onset and/or maintenance and/or development of a disease/disorder/condition, such as described herein. Chemical modifications as described herein can be applied to any nucleic acid construct disclosed herein. In another embodiment, a nucleic acid molecule disclosed herein includes a nucleotide sequence that can interact with nucleotide sequence of a p53 gene and thereby mediate down-regulation or silencing of p53 gene expression, for example, wherein the nucleic acid molecule mediates regulation of p53 gene expression by cellular processes that modulate the chromatin structure or methylation patterns of the gene and prevent transcription of the gene.

More particularly, provided are double-stranded nucleic acid molecules having a sense strand and an antisense strand sequences set forth in Table 1 (SEQ ID NOS:8-33) or homologs thereof wherein one to two of the ribonucleotides in each terminal region is altered.

Delivery and Formulations

Nucleic acid molecules of the present invention may be delivered to the target tissue by direct application of the naked molecules prepared with a carrier or a diluent.

The terms "naked nucleic acid" or "naked dsRNA" or "naked siRNA" refers to nucleic acid molecules that are free from any delivery vehicle that acts to assist, promote or facilitate entry into the cell, including viral sequences, viral particles, liposome formulations, lipofectin or precipitating agents and the like. For example, dsRNA in PBS is "naked dsRNA".

Nucleic acid molecules disclosed herein, or pharmaceutically acceptable salts thereof, may be delivered or administered directly with a carrier or diluent that acts to assist, promote or facilitate entry to the cell, including viral vectors, viral particles, liposome formulations, lipofectin or precipitating agents and the like.

A nucleic acid molecule may include a delivery vehicle, including liposomes, for administration to a subject, carriers and diluents and their salts, and/or can be present in pharmaceutically acceptable formulations. In some embodiments the dsRNA molecules of the invention are delivered in liposome formulations and lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al., FEBS Let. 2003, 539:111-114; Xia et al., Nat. Biotech. 2002, 20:1006-1010; Reich et al., Mol. Vision 2003, 9: 210-216; Sorensen et al., J. Mol. Biol. 2003. 327: 761-766; Lewis et al., Nat. Gen. 2002, 32: 107-108 and Simeoni et al., NAR 2003, 31, 11: 2717-2724). siRNA has recently been successfully used for inhibition of gene expression in primates (see for example, Tolentino et al., Retina 24(4):660).

Delivery of naked or formulated RNA molecules to the ear, optionally the inner ear, is accomplished, inter alia, by transtympanic injection or by administration of the desired compound formulated as an ear drop. Otic compositions comprising dsRNA are disclosed in US Publication No. 20110142917, to the assignee of the present application and incorporated herein by reference in its entirety.

Polypeptides that facilitate introduction of nucleic acid into a desired subject are known in the art, e.g. such as those described in US. Application Publication No. 20070155658 (e.g., a melamine derivative such as 2,4,6-Triguanidino Traizine and 2,4,6-Tramidosarcocyl Melamine, a polyarginine polypeptide, and a polypeptide including alternating glutamine and asparagine residues).

The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

In a particular embodiment, the administration comprises systemic administration. In another embodiment the administration comprises topical or local administration. Implants of the compounds are also useful. Liquid forms are prepared. The liquid compositions include aqueous solutions, with and without organic co-solvents, aqueous or oil suspensions, emulsions with edible oils, as well as similar pharmaceutical vehicles. Compositions may also be injected transtympanically or intravitreally. Compositions may also be applied as eye drops of eardrops.

Methods for the delivery of nucleic acid molecules are described in Akhtar et al., Trends Cell Bio., 2: 139 (1992); Delivery Strategies for Antisense Oligonucleotide Therapeutics, ed. Akhtar, (1995), Maurer et al., Mol. Membr. Biol., 16: 129-140 (1999); Hofland and Huang, Handb. Exp. Pharmacol., 137: 165-192 (1999); and Lee et al., ACS Symp. Ser., 752: 184-192 (2000); U.S. Pat. Nos. 6,395,713; 6,235, 310; 5,225,182; 5,169,383; 5,167,616; 4,959217; 4,925,678; 4,487,603; and 4,486,194 and Sullivan et al., PCT WO 94/02595; PCT WO 00/03683 and PCT WO 02/08754; and U.S. Patent Application Publication No. 2003077829. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see e.g., Gonzalez et al., Bioconjugate Chem., 10: 1068-1074 (1999); Wang et al., International PCT publication Nos. WO 03/47518 and WO 03/46185), poly(lactic-co-glycolic)acid (PLGA) and PLCA microspheres (see for example U.S. Pat. No. 6,447,796 and U.S. Application Publication No. 2002130430), biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether intravitreal, subcutaneous, transtympanic, intramuscular, or intradermal, can take place using standard needle and syringe methodologies, or by needle-free technologies such as those described in Conry et al., Clin. Cancer Res., 5: 2330-2337 (1999) and Barry et al., International PCT Publication No. WO 99/31262. The molecules of the instant invention can be used as pharmaceutical agents. Pharmaceutical agents prevent, modulate the occurrence, or treat or alleviate a symptom to some extent (preferably all of the symptoms) of a disease state in a subject. In one specific embodiment of this invention topical and transdermal formulations may be selected.

The nucleic acid compound, or pharmaceutically acceptable salt of such compound, or a composition comprising such compound, or a composition comprising the pharmaceutically acceptable salt of such compound, disclosed herein, is administered and dosed in accordance with good medical practice, taking into account the clinical condition of the individual subject, the disease to be treated, the site and method of administration, scheduling of administration, patient age, sex, body weight and other factors known to medical practitioners.

Nucleic acid molecules may be complexed with cationic lipids, packaged within liposomes, or otherwise delivered to target cells or tissues. The nucleic acid or nucleic acid complexes can be locally administered to relevant tissues ex vivo, or in vivo through direct dermal application, transdermal application, or injection, with or without their incorporation in biopolymers.

Delivery systems may include surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011).

Nucleic acid molecules may be formulated or complexed with polyethylenimine (e.g., linear or branched PEI) and/or polyethylenimine derivatives, including for example polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives, grafted PEIs such as galactose PEI, cholesterol PEI, antibody derivatized PEI, and polyethylene glycol PEI (PEG-PEI) derivatives thereof (see for example Ogris et al., 2001, AAPA PharmSci, 3, 1-11; Furgeson et al., 2003, Bioconjugate Chem., 14, 840-847; Kunath et al., 2002, Pharmaceutical Research, 19, 810-817; Choi et al., 2001, Bull. Korean Chem. Soc., 22, 46-52; Bettinger et al., 1999, Bioconjugate Chem., 10, 558-561; Peterson et al., 2002, Bioconjugate Chem., 13, 845-854; Erbacher et al., 1999, Journal of Gene Medicine Preprint, 1, 1-18; Godbey et al., 1999., PNAS USA, 96, 5177-5181; Godbey et al., 1999, Journal of Controlled Release, 60, 149-160; Diebold et al., 1999, Journal of Biological Chemistry, 274, 19087-19094; Thomas and Klibanov, 2002, PNAS USA, 99, 14640-14645; Sagara, U.S. Pat. No. 6,586,524 and US Patent Application Publication No. 20030077829).

Nucleic acid molecules may be complexed with membrane disruptive agents such as those described in U.S. Patent Application Publication No. 20010007666. The membrane disruptive agent or agents and the nucleic acid molecule may also be complexed with a cationic lipid or helper lipid molecule, such as those lipids described in U.S. Pat. No. 6,235,310.

Nucleic acid molecules disclosed herein may be administered to the central nervous system (CNS) or peripheral nervous system (PNS). Experiments have demonstrated the efficient in vivo uptake of nucleic acids by neurons. See e.g., Sommer et al., 1998, Antisense Nuc. Acid Drug Dev., 8, 75; Epa et al., 2000, Antisense Nuc. Acid Drug Dev., 10, 469; Broaddus et al., 1998, J. Neurosurg., 88(4), 734; Karle et al., 1997, Eur. J. Pharmacol., 340(2/3), 153; Bannai et al., 1998, Brain Research, 784(1,2), 304; Rajakumar et al., 1997, Synapse, 26(3), 199; Wu-pong et al., 1999, BioPharm, 12(1), 32; Bannai et al., 1998, Brain Res. Protoc., 3(1), 83; and Simantov et al., 1996, Neuroscience, 74(1), 39. Nucleic acid molecules are therefore amenable to delivery to and uptake by cells in the CNS and/or PNS, e.g. neurons, macrophages, white matter axons and endothelial cells.

Delivery systems may include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer. Non-limiting examples of liposomes which can be used with the compounds of this invention include the following: (1) CellFectin, 1:1.5 (M/M) liposome formulation of the cationic lipid N,NI,NII,NIII-tetramethyl-N,NI,NII,NIII-tetrapalmit-y-spermine and dioleoyl phosphatidylethanolamine (DOPE) (GIBCO BRL); (2) Cytofectin GSV, 2:1 (M/M) liposome formulation of a cationic lipid and DOPE (Glen Research); (3) DOTAP (N-[1-(2,3-dioleoyloxy)-N,N,N-tri-methyl-ammoniummethylsulfate) (Boehringer Manheim); and (4) Lipofectamine, 3:1 (M/M) liposome formulation of the polycationic lipid DOSPA, the neutral lipid DOPE (GIBCO BRL) and Di-Alkylated Amino Acid (DiLA2).

Delivery systems may include patches, tablets, suppositories, pessaries, gels, aqueous and nonaqueous solutions, lotions and creams, and can contain excipients such as solubilizers and enhancers (e.g., propylene glycol, bile salts and amino acids), and other vehicles (e.g., polyethylene glycol, glycerol, fatty acid esters and derivatives, and hydrophilic polymers such as hydroxypropylmethylcellulose and hyaluronic acid).

Nucleic acid molecules may include a bioconjugate, for example a nucleic acid conjugate as described in Vargeese et al., U.S. Ser. No. 10/427,160; U.S. Pat. Nos. 6,528,631; 6,335,434; 6,235,886; 6,153,737; 5,214,136; 5,138,045.

Compositions, methods and kits disclosed herein may include an expression vector that includes a nucleic acid sequence encoding at least one nucleic acid molecule of the invention in a manner that allows expression of the nucleic acid molecule. Methods of introducing nucleic acid molecules or one or more vectors capable of expressing the strands of a double-stranded oligonucleotide compound into the environment of the cell will depend on the type of cell and the make up of its environment. The nucleic acid molecule or the vector construct may be directly introduced into the cell (i.e., intracellularly); or introduced extracellularly into a cavity, interstitial space, into the circulation of an organism, introduced orally, or may be introduced by bathing an organism or a cell in a solution containing the nucleic acid compound. The cell is preferably a mammalian cell; more preferably a human cell. The nucleic acid molecule of the expression vector can include a sense region and an antisense region. The antisense region can include a sequence complementary to a RNA or DNA sequence encoding p53 gene, and the sense region can include a sequence complementary to the antisense region. The nucleic acid molecule can include two distinct strands having complementary sense and antisense regions. The nucleic acid molecule can include a single strand having complementary sense and antisense regions.

Nucleic acid molecules that interact with target RNA molecules and down-regulate a p53 gene encoding target RNA molecules (e.g., mRNA, SEQ ID NO:1-7) may be expressed from transcription units inserted into DNA or RNA vectors. Recombinant vectors can be DNA plasmids or viral vectors. Nucleic acid molecule expressing viral vectors can be constructed based on, but not limited to, adeno-associated virus, retrovirus, adenovirus, or alphavirus. The recombinant vectors capable of expressing the nucleic acid molecules can be delivered as described herein, and persist in target cells. Alternatively, viral vectors can be used that provide for transient expression of nucleic acid molecules. Such vectors can be repeatedly administered as necessary. Once expressed, the nucleic acid molecules bind and down-regulate gene function or expression, e.g., via RNA interference (RNAi). Delivery of nucleic acid molecule expressing vectors can be systemic, such as by intravenous or intramuscular administration, by local administration, by administration to target cells ex-planted from a subject followed by reintroduction into the subject, or by any other means that would allow for introduction into the desired target cell.

Expression vectors may include a nucleic acid sequence encoding at least one nucleic acid molecule disclosed herein, in a manner which allows expression of the nucleic acid molecule. For example, the vector may contain sequence(s) encoding both strands of a nucleic acid molecule that include a duplex. The vector can also contain sequence(s) encoding a single nucleic acid molecule that is self-complementary and thus forms a nucleic acid molecule. Non-limiting examples of such expression vectors are described in Paul et al., 2002, Nature Biotechnology, 19, 505; Miyagishi and Taira, 2002, Nature Biotechnology, 19, 497; Lee et al., 2002, Nature Biotechnology, 19, 500; and Novina et al., 2002, Nature Medicine, advance online publication doi: 10.1038/nm725. Expression vectors may also be included in a mammalian (e.g., human) cell.

An expression vector may encode one or both strands of a nucleic acid duplex, or a single self-complementary strand that self hybridizes into a nucleic acid duplex. The nucleic acid sequences encoding nucleic acid molecules can be operably linked in a manner that allows expression of the nucleic acid molecule (see for example Paul et al., 2002, Nature Biotechnology, 19, 505; Miyagishi and Taira, 2002, Nature Biotechnology, 19, 497; Lee et al., 2002, Nature Biotechnology, 19, 500; and Novina et al., 2002, Nature Medicine, advance online publication doi:10.1038/nm725).

An expression vector may include one or more of the following: a) a transcription initiation region (e.g., eukaryotic pol I, II or III initiation region); b) a transcription termination region (e.g., eukaryotic pol I, II or III termination region); c) an intron and d) a nucleic acid sequence encoding at least one of the nucleic acid molecules, wherein said sequence is operably linked to the initiation region and the termination region in a manner that allows expression and/or delivery of the nucleic acid molecule. The vector can optionally include an open reading frame (ORF) for a protein operably linked on the 5'-side or the 3'-side of the sequence encoding the nucleic acid molecule; and/or an intron (intervening sequences).

Transcription of the nucleic acid molecule sequences can be driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA, 87, 6743-7; Gao and Huang 1993, Nucleic Acids Res., 21, 2867-72; Lieber et al., 1993, Methods Enzymol., 217, 47-66; Zhou et al., 1990, Mol. Cell. Biol., 10, 4529-37). Several investigators have demonstrated that nucleic acid molecules expressed from such promoters can function in mammalian cells (e.g. Kashani-Sabet et al., 1992, Antisense Res. Dev., 2, 3-15; Ojwang et al., 1992, Proc. Natl. Acad. Sci. USA, 89, 10802-6; Chen et al., 1992, Nucleic Acids Res., 20, 4581-9; Yu et al., 1993, Proc. Natl. Acad. Sci. USA, 90, 6340-4; L'Huillier et al., 1992, EMBO J., 11, 4411-8; Lisziewicz et al., 1993, Proc. Natl. Acad. Sci. U.S.A, 90, 8000-4; Thompson et al., 1995, Nucleic Acids Res., 23, 2259; Sullenger & Cech, 1993, Science, 262, 1566). More specifically, transcription units such as the ones derived from genes encoding U6 small nuclear (snRNA), transfer RNA (tRNA) and adenovirus VA RNA are useful in generating high concentrations of desired RNA molecules such as siNA in cells (Thompson et al., supra; Couture and Stinchcomb, 1996, supra; Noonberg et al., 1994, Nucleic Acid Res., 22, 2830; Noonberg et al., U.S. Pat. No. 5,624,803; Good et al., 1997, Gene Ther., 4, 45; Beigelman et al., International PCT Publication No. WO 96/18736). The above nucleic acid transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (see Couture and Stinchcomb, 1996 supra).

Nucleic acid molecule may be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591-5; Kashani-Sabet et al., 1992, Antisense Res. Dev., 2, 3-15; Dropulic et al., 1992, J. Virol., 66, 1432-41; Weerasinghe et al., 1991, J. Virol., 65, 5531-4; Ojwang et al., 1992, Proc. Natl. Acad. Sci. USA, 89, 10802-6; Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45. Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., 1992, Nucleic Acids Symp. Ser., 27, 15-6; Taira et al., 1991, Nucleic Acids Res., 19, 5125-30; Ventura et al., 1993, Nucleic Acids Res., 21, 3249-55; Chowrira et al., 1994, J. Biol. Chem., 269, 25856.

A viral construct packaged into a viral particle would accomplish both efficient introduction of an expression construct into the cell and transcription of dsRNA construct encoded by the expression construct.

Methods for oral introduction include direct mixing of RNA with food of the organism, as well as engineered approaches in which a species that is used as food is engineered to express an RNA, then fed to the organism to be affected. Physical methods may be employed to introduce a nucleic acid molecule solution into the cell. Physical methods of introducing nucleic acids include injection of a solution containing the nucleic acid molecule, bombardment by particles covered by the nucleic acid molecule, soaking the cell or organism in a solution of the RNA, or electroporation of cell membranes in the presence of the nucleic acid molecule. In one embodiment provided herein is a cell comprising a nucleic acid molecule disclosed herein.

Other methods known in the art for introducing nucleic acids to cells may be used, such as chemical mediated transport, such as calcium phosphate, and the like. Thus the nucleic acid molecules may be introduced along with components that perform one or more of the following activities: enhance RNA uptake by the cell, promote annealing of the duplex strands, stabilize the annealed strands, or other-wise increase inhibition/down-regulation of the target gene.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Nucleic acid molecules may be formulated as a microemulsion. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sesquioleate (SO750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Delivery formulations can include water soluble degradable crosslinked polymers that include one or more degradable crosslinking lipid moiety, one or more PEI moiety, and/or one or more mPEG (methyl ether derivative of PEG (methoxypoly (ethylene glycol)).

Dosages

The useful dosage to be administered and the particular mode of administration will vary depending upon such factors as the cell type, or for in vivo use, the age, weight and the particular animal and region thereof to be treated, the particular nucleic acid and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

Suitable amounts of nucleic acid molecules may be introduced and these amounts can be empirically determined using standard methods. Effective concentrations of individual nucleic acid molecule species in the environment of a cell may be about 1 femtomolar, about 50 femtomolar, 100 femtomolar, 1 picomolar, 1.5 picomolar, 2.5 picomolar, 5 picomolar, 10 picomolar, 25 picomolar, 50 picomolar, 100 picomolar, 500 picomolar, 1 nanomolar, 2.5 nanomolar, 5 nanomolar, 10 nanomolar, 25 nanomolar, 50 nanomolar, 100 nanomolar, 500 nanomolar, 1 micromolar, 2.5 micromolar, 5 micromolar, 10 micromolar, 100 micromolar or more.

In general, the active dose of nucleic acid compound for humans is in the range of from 1 ng/kg to about 20-100 milligrams per kilogram (mg/kg) body weight of the recipient per day, preferably about 0.01 mg to about 2-10 mg/kg body weight of the recipient per day, in a regimen of a single dose, a one dose per day or twice or three or more times per day for a period of 1-4 weeks or longer. A suitable dosage unit of nucleic acid molecules may be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Dosage may be from 0.01 ug to 1 g per kg of body weight (e.g., 0.1 ug, 0.25 ug, 0.5 ug, 0.75 ug, 1 ug, 2.5 ug, 5 ug, 10 ug, 25 ug, 50 ug, 100 ug, 250 ug, 500 ug, 1 mg, 2.5 mg, 5 mg, 10 mg, 25 mg, 50 mg, 100 mg, 250 mg, or 500 mg per kg of body weight).

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depends upon the host treated and the particular mode of administration. Dosage unit forms generally contain between from about 1 mg to about 500 mg of an active ingredient.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

Pharmaceutical compositions that include the nucleic acid molecule disclosed herein may be administered once daily (QD), twice a day (bid), three times a day (tid), four times a day (qid), or at any interval and for any duration that is medically appropriate. However, the therapeutic agent may also be dosed in dosage units containing two, three, four, five, six or more sub-doses administered at appropriate intervals throughout the day. In that case, the nucleic acid molecules contained in each sub-dose may be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. The dosage unit may contain a corresponding multiple of the daily dose. The composition can be compounded in such a way that the sum of the multiple units of a nucleic acid together contain a sufficient dose.

Pharmaceutical Compositions, Kits, and Containers

Also provided are compositions, kits, containers and formulations that include a nucleic acid molecule (e.g., an siNA molecule) as provided herein for down-regulating expression of p53 gene for administering or distributing the nucleic acid molecule to a patient. A kit may include at least one container and at least one label. Suitable containers include, for example, bottles, vials, syringes, and test tubes. The containers can be formed from a variety of materials such as glass, metal or plastic. The container can hold nucleic acid sequence(s), and/or any other component required for relevant laboratory, prognostic, diagnostic, prophylactic and therapeutic purposes. Indications and/or directions for such uses can be included on or with such container, as can reagents and other compositions or tools used for these purposes.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agent in the composition preferably comprise a nucleic acid molecule capable of specifically binding p53 mRNA and/or down-regulating the function of p53 gene.

A kit may further include a second container that includes a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

Federal law requires that the use of pharmaceutical compositions in the therapy of humans be approved by an agency of the Federal government. In the United States, enforcement is the responsibility of the Food and Drug Administration, which issues appropriate regulations for securing such approval, detailed in 21 U.S.C. § 301-392. Regulation for biologic material, including products made from the tissues of animals is provided under 42 U.S.C. § 262. Similar approval is required by most foreign countries. Regulations vary from country to country, but individual procedures are well known to those in the art and the compositions and methods provided herein preferably comply accordingly.

The nucleic acid molecules disclosed herein can be used to treat diseases, conditions or disorders associated with p53, such as disease, injury, condition or pathology in the ear, vestibular sensory system, and any other disease or conditions that are related to or will respond to the levels of p53 in a cell or tissue, alone or in combination with other therapies. As such, compositions, kits and methods disclosed herein may include packaging a nucleic acid molecule disclosed herein that includes a label or package insert. The label may include indications for use of the nucleic acid molecules such as use for treatment or prevention of diseases, disorders, injuries and conditions, including, without being limited to, any disease or condition disclosed herein. The label may include indications for use of the nucleic acid molecules such as use for treatment or prevention of attenuation of such disease, injury or condition. The label may include indications for use of the nucleic acid molecules such as use for treatment or prevention of any other disease or conditions that are related to or will respond to the levels of p53 in a cell or tissue, alone or in combination with other therapies. A label may include an indication for use in reducing and/or down-regulating expression of p53. A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

Those skilled in the art will recognize that other treatments, drugs and therapies known in the art can be readily combined with the nucleic acid molecules herein (e.g. dsNA molecules) and are hence contemplated herein.

Methods of Treatment

In another aspect, the present invention relates to a method for the treatment of a subject in need of treatment for a disease or disorder associated with the abnormal expression of p53 gene, comprising administering to the subject an amount of an inhibitor, which reduces or inhibits expression of the p53 gene.

In one embodiment, nucleic acid molecules may be used to down-regulate or inhibit the expression of p53 gene and/or p53 protein and/or haplotype polymorphisms that are associated with a disease or condition, (e.g., ischemia). Analysis of p53 gene, and/or protein or RNA levels can be used to identify subjects with such polymorphisms or those subjects who are at risk of developing traits, conditions, or diseases described herein. These subjects are amenable to treatment, for example, treatment with nucleic acid molecules disclosed herein and any other composition useful in treating diseases related to p53 gene expression. As such, analysis of p53 gene and/or protein or RNA levels can be used to determine treatment type and the course of therapy in treating a subject. Monitoring of protein or RNA levels can be used to predict treatment outcome and to determine the efficacy of compounds and compositions that modulate the level and/or activity of certain genes and/or proteins associated with a trait, condition, or disease.

The some embodiment the nucleic acid compounds disclosed herein are for use in a method of down-regulating the expression of a p53 gene transcribed into mRNA set forth in any one of SEQ ID NOS:1-7 by at least 40%, preferably by 50%, 60% or 70%, more preferably by 75%, 80% or 90% as compared to a control, comprising contacting an mRNA transcript of the p53 gene with one or more of the compounds.

In various embodiments the nucleic acid compounds disclosed herein inhibit the p53 gene, whereby the inhibition is selected from the group comprising inhibition of gene function, inhibition of polypeptide and inhibition of mRNA expression.

In one embodiment the nucleic acid compound disclosed herein inhibits the p53 polypeptide, whereby the inhibition is selected from the group comprising inhibition of function (which is examined by, for example, an enzymatic assay or a binding assay with a known interactor of the native gene/polypeptide, inter alia), inhibition of protein (which is examined by, for example, Western blotting, ELISA or immuno-precipitation, inter alia) and inhibition of mRNA expression (which is examined by, for example, Northern blotting, quantitative RT-PCR, in-situ hybridization or microarray hybridization, inter alia).

In one embodiment the nucleic acid compound disclosed herein is down-regulating a mammalian p53 polypeptide, whereby the down-regulation is selected from the group comprising down-regulation of function (which is examined by, for example, an enzymatic assay or a binding assay with a known interactor of the native gene/polypeptide, inter alia), down-regulation of protein (which is examined by, for example, Western blotting, ELISA or immuno-precipitation, inter alia) and down-regulation of mRNA expression (which is examined by, for example, Northern blotting, quantitative RT-PCR, in-situ hybridization or microarray hybridization, inter alia).

Methods, molecules and compositions which inhibit a p53 gene or polypeptide are discussed herein at length, and any of said molecules and/or compositions are beneficially employed in the treatment of a patient suffering from any of said conditions. It is to be explicitly understood that known compounds are excluded from the present disclosure. Novel methods of treatment using known compounds and compositions fall within the scope of the present disclosure. The methods include administering a therapeutically effective amount of one or more nucleic acid compounds disclosed herein which down-regulate expression of a p53 gene. In some embodiments of the method a nucleic acid compound disclosed herein is for treating a disease, a disorder or a condition associated with an exposure to a toxic agent, By "exposure to a toxic agent" is meant that the toxic agent is made available to, or comes into contact with, a mammal. A toxic agent can be toxic to the nervous system. Exposure to a toxic agent can occur by direct administration, e.g., by ingestion or administration of a food, medicinal, or therapeutic agent, e.g., a chemotherapeutic agent, by accidental contamination, or by environmental exposure, e g., aerial or aqueous exposure.

Further provided is a process of preparing a pharmaceutical composition, which comprises:

providing one or more nucleic acid molecule disclosed herein, or a pharmaceutically acceptable salt thereof; and admixing said molecule or said salt thereof with a pharmaceutically acceptable carrier.

In a preferred embodiment, the molecule used in the preparation of a pharmaceutical composition is admixed with a carrier in a pharmaceutically effective dose. In a particular embodiment the nucleic acid compound disclosed herein is conjugated to a steroid or to a lipid or to another suitable molecule e.g. to cholesterol.

Provided are compositions and methods for down-regulation of p53 expression by using a nucleic acid molecules as provided herein, such as, without being limited to, a short interfering nucleic acid (siNA), interfering RNA (RNAi), short interfering RNA (siRNA), double-stranded RNA (dsRNA), micro-RNA (miRNA), and short hairpin RNA (shRNA) molecules capable of down-regulating p53 gene expression, or of mediating RNA interference against p53 gene expression. The composition and methods disclosed herein are also useful in treating various conditions or diseases, such as, e.g. disorders, disease and injury described herein.

The nucleic acid molecules disclosed herein individually, or in combination or in conjunction with other drugs, can be used for preventing or treating diseases, traits, conditions and/or disorders associated with p53, such as, without being limited to, diseases, disorders and injuries described herein.

The nucleic acid molecules disclosed herein are able to down-regulate the expression of p53 gene in a sequence specific manner. The nucleic acid molecules may include a sense strand and an antisense strand which include contiguous nucleotides that are at least partially complementary (antisense) to a portion of p53 mRNA (e.g. SEQ ID NOS: 1-7).

In some embodiments, nucleic acid compounds specific for p53 can be used in conjunction with other therapeutic agents and/or nucleic acid compounds specific for other molecular targets, such as, without being limited to, various proapoptotic genes.

A method for treating or preventing a disease or a condition that is associated with the expression of p53 in a subject or an organism may include contacting the subject or the organism with a nucleic acid molecule provided herein under conditions suitable for down-regulating the expression of the p53 gene in the subject or organism.

In preferred embodiments the subject being treated is a warm-blooded animal and, in particular, mammals including human.

The methods disclosed herein comprise administering to the subject one or more inhibitory compounds which down-regulate expression of p53 gene; and in particular nucleic acid compounds described herein, in a therapeutically effective dose so as to thereby treat the subject.

The molecules disclosed herein, particularly novel double-stranded nucleic acid compounds, down-regulate the expression of p53 and are useful in the treatment of diseases or conditions in which down-regulation of the expression of p53 is beneficial. Methods, molecules and compositions which down-regulate p53 are discussed herein at length, and any of said molecules and/or compositions may be beneficially employed in the treatment of a subject suffering from any of said conditions. Sense strand and antisense strand oligonucleotide sequences useful in generating nucleic acid compounds are set forth in Table 1 (SEQ ID NOS:8-33). Specific oligonucleotide compounds are set forth in Tables A, B and E. In preferred embodiments the subject being treated is a warm-blooded animal and, in particular, mammal, including human.

The term "treatment" refers to both therapeutic treatment and prophylactic or preventative measures, wherein the object is to prevent a disorder or reduce the symptoms of a disorder, such as hearing disorder or impairment (or balance impairment), or to prevent or reduce cell death associated with a hearing loss-associated disease as listed herein. Those in need of treatment include those already experiencing the disease or condition, those prone to having the disease or condition, and those in which the disease or condition is to be prevented. The nucleic acid compounds disclosed herein are administered before, during or subsequent to the onset of the disease or condition.

In some embodiments the molecules and compositions provided herein are co-administered with an ototoxin. For example, an improved method is provided for treatment of infection of a mammal by administration of an aminoglycoside antibiotic, the improvement comprising administering a therapeutically effective amount of one or more compounds (particularly novel siRNAs) which down-regulate expression of p53, to the patient in need of such treatment to reduce or prevent ototoxin-induced hearing impairment associated with the antibiotic. The compounds which down-regulate expression of p53, particularly novel dsRNAs are preferably administered locally within the inner ear.

In yet another embodiment an improved method for treatment of cancer in a mammal by administration of a chemotherapeutic compound is provided, wherein the improvement comprises administering a therapeutically effective amount of a composition of the invention to the patient in need of such treatment to reduce or prevent ototoxin-induced hearing impairment associated with the chemotherapeutic drug. The compounds which reduce or prevent the ototoxin-induced hearing impairment, e.g. the dsRNA molecules disclosed herein, inter alia are preferably administered directly, e.g. to the cochlea, as naked dsRNA in a vehicle such as PBS or other physiological solutions, but may alternatively be administered with a delivery vehicle as described above.

In some embodiments combination therapy is preferred. Combination therapy is achieved by administering two or more agents (i.e. two or more dsRNA or at least one dsRNA and at least one another therapeutic agent) each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within one or several hours of each other or within one or several days of each other or within several weeks of each other. In some cases even longer intervals are possible. The two or more agents used in combination therapy may or may not be present within the patient's body at the same time. Combination therapy includes two or more administrations of one or more of the agents used in the combination. For example, if dsRNA1 and dsRNA2 are used in a combination, one could administer them sequentially in any combination one or more times, e.g., in the order dsRNA1-dsRNA2, dsRNA2-dsRNA1, dsRNA1-dsRNA2-dsRNA1, dsRNA2-dsRNA1-dsRNA2, dsRNA1-dsRNA1-dsRNA2, dsRNA1-dsRNA2-dsRNA2 etc.

Details of certain indications in which the compounds disclosed herein are useful as therapeutics are described herein.

Embodiments have been described in an illustrative manner, and it is to be understood that the terminology used is intended to be in the nature of words of description rather than of limitation.

Throughout this application, various publications, including United States Patents, are referenced by author and year and patents by number. The disclosures of these publications and patents and patent applications in their entireties are hereby incorporated by reference into this application in order to more fully describe the state of the art to which this disclosure pertains.

The compositions and methods provided herein will now be described in greater detail by reference to the following non-limiting examples.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out as in standard PCR Protocols: A Guide To Methods And Applications, Academic Press, San Diego, Calif. (1990). In situ PCR in combination with Flow Cytometry (FACS) can be used for detection of cells containing specific DNA and mRNA sequences (Testoni et al., Blood 1996, 87:3822.) Methods of performing RT-PCR are well known in the art.

Example 1: Generation of Novel Sequences for Active dsRNA Compounds

Using proprietary algorithms and the known sequence of the mRNA of the p53 gene (SEQ ID NOS:1-7), the sequences of many potential dsRNA, were generated.

The oligonucleotide sequences were prioritized based on their score in the proprietary algorithm as the best predicted sequences for targeting the human gene expression.

Example 2: Identification of Preferred Novel Sequences for Active Nucleic Acid Compounds and Generation of Novel Double-Stranded Nucleic Acid Compounds The best scoring oligonucleotide sequences were further prioritized based on their activity in vitro. For this purpose, dsRNA compounds were synthesized having the following modification patterns:

dsRNA compound identified by the ending "_S709" having unmodified ribonucleotides in the antisense strand and in the sense strand, and a -dTdT$3'-end overhang in both the antisense strand and the sense strand, with dT designating thymidine and dT$ designating thymidine with no terminal phosphate.

dsRNA compound identified by the ending _S500 have the following modification pattern: Alternating 2'-O-methyl (Me) sugar modified ribonucleotides are present in the first, third, fifth, seventh, ninth, eleventh, thirteenth, fifteenth, seventeenth and nineteenth positions of the antisense strand, whereby the very same modification, i.e. a 2'-O-Methyl sugar modified ribonucleotides are present in the second, fourth, sixth, eighth, tenth, twelfth, fourteenth, sixteenth and eighteenth positions of the sense strand.

dsRNA compounds identified by the prefixes "p53_3", "p53_QMON1" and "p53_1" were used as control, the sequences of the antisense strand and the sense strand of these control compounds are provided in Table C.

TABLE C

| dsRNA Name | Sense strand (5'>3') | Antisense strand (5'>3') |
|---|---|---|
| p53_3 | 5' CCGAGUGGAAGGAAAUUUG 3' | 5' CAAAUUUCCUUCCACUCGG 3' |
| p53_13 | 5' CAGACCUAUGGAAACUACU 3' | 5' AGUAGUUUCCAUAGGUCUG 3' |
| p53_1 | 5' GAGAAUAUUUCACCCUUCA 3' | 5' UGAAGGGUGAAAUAUUCUC 3' |

In all tables above and below the duplex names are identified by prefixes "p53" and "TP53" that are used interchangeably.

The following assay was used for the in vitro activity studies.

Activity Assay

About 1.5-2×10⁵ tested human or rat cells endogenously expressing p53 genes (Human HCT116 cells or Rat REF52 cells) were grown in 6 wells plate in 1.5 ml growth medium for about 24 hours to 30-50% confluence.

Cells were then transfected with tested dsRNA compound in a required final concentration 0.001-100 nM per well using Liopofectamine 2000 reagent.

In order to determine the transfection efficiency, of the study, 5 wells were treated independently with Lipofectamine 2000 reagent and defined as "Negative Control samples" and 5 wells were transfected independently with active dsRNA at final concentration of 5 nM defined as "Control active samples" (positive control). Cy3-labeled siRNA transfected cells were used as positive control for transfection efficiency.

Cells were then incubated in a 37±1° C., 5% CO₂ incubator for 48-72 hours. dsRNA transfected cells were harvested and RNA was isolated using EZ-RNA kit [Biological Industries (#20-410-100)]. Reverse transcription was performed as follows: cDNA was synthesized and human and/or rat p53 mRNA levels were determined, accordingly by Real Time qPCR and normalized to those of the Cyclophilin A (CYNA, PPIA) mRNA for each sample. dsRNA activity was determined based on the ratio of the mRNA quantity in siRNA-treated samples versus non-transfected control samples.

As a result of the activity study preferred sequences for novel dsRNA compounds for down regulation of the p53 gene were identified. These sequences are set forth in Table 1, supra (SEQ ID NOS: 8-33). The activity results obtained with compounds having these sequence and having modification pattern identified by the ending "_S709" are presented in Table D. dsRNA compounds identified by the ending "_S709" have unmodified ribonucleotides in the antisense strand and in the sense strand, and a -dTdT$3'-end overhang in both the antisense strand and the sense strand, with dT designating thymidine and dT$ designating thymidine with no terminal phosphate.

TABLE D

| Sample Description (dsRNA compound used) | Concentration of dsRNA compound | p53 residual mRNA % of control |
|---|---|---|
| p53_34_S709 | 80 nM | 36 |
| p53_34_S709 | 40 nM | 44 |

TABLE D-continued

| Sample Description (dsRNA compound used) | Concentration of dsRNA compound | p53 residual mRNA % of control |
|---|---|---|
| p53_34_S709 | 20 nM | 40 |
| p53_34_S709 | 4 nM | 70 |
| p53_35_S709 | 80 nM | 49 |
| p53_35_S709 | 40 nM | 40 |
| p53_35_S709 | 20 nM | 94 |
| p53_35_S709 | 4 nM | 119 |
| p53_36_S709 | 80 nM | 105 |
| p53_36_S709 | 40 nM | 126 |
| p53_36_S709 | 20 nM | 144 |
| p53_36_S709 | 4 nM | 150 |
| p53_37_S709 | 80 nM | 73 |
| p53_37_S709 | 40 nM | 58 |
| p53_37_S709 | 20 nM | 119 |
| p53_37_S709 | 4 nM | 84 |
| p53_38_S709 | 80 nM | 65 |
| p53_38_S709 | 40 nM | 55 |
| p53_38_S709 | 20 nM | 53 |
| p53_38_S709 | 4 nM | 122 |
| p53_39_S709 | 80 nM | 73 |
| p53_39_S709 | 40 nM | 48 |
| p53_39_S709 | 20 nM | 67 |
| p53_39_S709 | 4 nM | 106 |
| p53_40_S709 | 80 nM | 43 |
| p53_40_S709 | 40 nM | 58 |
| p53_40_S709 | 20 nM | 62 |
| p53_40_S709 | 4 nM | 67 |
| p53_41_S709 | 80 nM | 35 |
| p53_41_S709 | 40 nM | 26 |
| p53_41_S709 | 20 nM | 49 |
| p53_41_S709 | 4 nM | 67 |
| p53_42_S709 | 80 nM | |
| p53_42_S709 | 40 nM | 84 |
| p53_42_S709 | 20 nM | 96 |
| p53_42_S709 | 4 nM | 82 |

As shown in Table D, double-stranded nucleic acid compounds p53_34_S709, p53_35_S709, p53_37_S709, p53_38_S709, p53_39_S709, p53_40_S709, p53_41_S709 and p53_42_S709, were found active against target human p53 mRNA, with p53_41_S709 being the most active compound.

Example 3: Generation and Testing of Novel Modified Double-Stranded Nucleic Acid Compounds The preferred sequences (SEQ ID NOS: 8-33) were used for generating novel modified double-stranded nucleic acid compounds. Novel modified double-stranded nucleic acid compounds that were generated using the preferred antisense strand and sense strand sequences are set forth in Tables A and B, supra. Table E below shows some preferred novel modified double-stranded nucleic acid compounds that were generated using the preferred antisense strand and sense strand sequences (SEQ ID NOS: 8-33).

TABLE E

| dsRNA Compound | Sense (N')y 5->3 | Antisense (N)x 5->3 |
|---|---|---|
| TP53_13_S2275 | C3-CAGACCUAUGGAAACUACU-C3-pi | 5' phos-AGUAGUuUCCAUAGGUCUG-C3;C3-pi |
| TP53_13_S2276 | C3-CAGACCUAUGGAAACUACU-C3-pi | 5' phos-AGUAGUuUCCAUAGGUCUG-C3;C3-pi |
| TP53_13_S2277 | C3-CAGACCUAUGGAAAcuacu-C3-pi | 5' phos-AGUAGUuUCCAUAGGUCUG-C3;C3-pi |
| TP53_13_S2278 | C3-CAGACCUAUGGAAAcuacu-C3-pi | 5' phos-AGUAGUuUCCAUAGGUCUG-C3;C3-pi |
| TP53_41_S709 | GACUCAGACUGACAUUCUU-dTdT$ | AAGAAUGUCAGUCUGAGUC-dTdT$ |
| TP53_41_S2279 | C3-GACUCAGACUGACAUUCUU-C3-pi | 5' phos-AAGAAUgUCAGUCUGAGUC-C3;C3-pi |

TABLE E-continued

| dsRNA Compound | Sense (N')y 5->3 | Antisense (N)x 5->3 |
|---|---|---|
| TP53_41_S2298 | C3-GACUCAGACUGACAuucuu-C3-pi | 5' phos-AAGAAUgUCAGUCUGAGUC-C3;C3-pi |
| TP53_41_S2299 | C3-GACUCAGACUGACAuucuu-C3-pi | 5' phos-AAGAAUgUCAGUCUGAGUC-C3; C3-pi |
| TP53_41_S2300 | C3-GACUCAGACUGACAUUCUU-C3-pi | 5' phos-AAGAAUgUCAGUCUGAGUC-C3;C3-pi |
| TP53_44_S2301 | C3-GGGCCUGACUCAGAcugau-C3-pi | 5' phos-AUCAGUcUGAGUCAGGCCC-C3;C3-pi |
| TP53_44_S2302 | C3-GGGCCUGACUCAGAcugau-C3-pi | 5' phos-AUCAGUcUGAGUCAGGCCC-C3;C3-pi |
| TP53_44_S2303 | C3-GGGCCUGACUCAGACUGAU-C3-pi | 5' phos-AUCAGUcUGAGUCAGGCCC-C3;C3-pi |
| TP53_44_S2304 | C3-GGGCCUGACUCAGACUGAU-C3-pi | 5' phos-AUCAGUcUGAGUCAGGCCC-C3;C3-pi |

In all tables above and below the duplex names are identified by prefixes "p53" and "TP53" that are used interchangeably. Thus, for example a compound identified by prefix "p53_13" and "TP53_13" designates a double-stranded nucleic acid compound having a sense strand sequence 5' CAGACCUAUGGAAACUACU 3' (SEQ ID NO:8) and an antisense strand sequence 5' AGUAGUUUC-CAUAGGUCUG 3' (SEQ ID NO: 21).

For all dsRNA compounds in Table E:
A, U, G, C—designates an unmodified ribonucleotide;
A, U, G, C—designates a 2-O-methyl sugar modified ribonucleotide;
a, u, c, g—designates a nucleotide joined to an adjacent nucleotide (5'>3') by a 2'-5' internucleotide phosphate bond;
C3—designates 1,3-Propanediol, mono(dihydrogen phosphate) also identified as 3-Hydroxypropane-1-phosphate capping moiety [CAS RN: 13507-42-1].
C3C3—designates a capping moiety consisting of two consecutive C3 molecules
pi—designates 3'-phosphate.
5'-phos—designates 5'-phosphate Activity of novel modified double-stranded nucleic acid compounds was studies in human HCT116 cells and in rat REF52 cells.

Table F1 summarizes the in vitro activity results obtained for some of the novel double-stranded nucleic acid molecules in human HCT116 cell line. All the novel dsRNA compounds are described in Table E, supra. p53_13_S500 is a known compound that was used for comparative purposes. The p53_13_S500 compound has the sense strand and antisense strand sequences described in Table C, supra.

The p53_13_S500 compound has the following modification pattern: alternating 2'-O-methyl (Me) sugar modified ribonucleotides are present in the first, third, fifth, seventh, ninth, eleventh, thirteenth, fifteenth, seventeenth and nineteenth positions of the antisense strand, whereby the very same modification, i. e. a 2'-O-Methyl sugar modified ribonucleotides are present in the second, fourth, sixth, eighth, tenth, twelfth, fourteenth, sixteenth and eighteenth positions of the sense strand.

The in-vitro activity in Table F1 is demonstrated as the % residual target mRNA relative to control.

TABLE F1

| Sample Description (dsRNA compound used) | Concentration of dsRNA compound | p53 residual mRNA % of control |
|---|---|---|
| None (control) | | 100 |
| p53_13_S500 | 50 nM | 25 |

TABLE F1-continued

| Sample Description (dsRNA compound used) | Concentration of dsRNA compound | p53 residual mRNA % of control |
|---|---|---|
| p53_13_S500 | 25 nM | 14 |
| p53_13_S500 | 5 nM | 33 |
| p53_13_S500 | 1 nM | 55 |
| p53_1_S500 | 50 nM | 22 |
| p53_1_S500 | 25 nM | 16 |
| p53_1_S500 | 5 nM | 52 |
| p53_1_S500 | 1 nM | 107 |
| p53_13_S2275 | 50 nM | 19 |
| p53_13_S2275 | 25 nM | 14 |
| p53_13_S2275 | 5 nM | 25 |
| p53_13_S2275 | 1 nM | 60 |
| p53_13_S2276 | 50 nM | 19 |
| p53_13_S2276 | 25 nM | 19 |
| p53_13_S2276 | 5 nM | 44 |
| p53_13_S2276 | 1 nM | 112 |
| p53_13_S2277 | 50 nM | 22 |
| p53_13_S2277 | 25 nM | 14 |
| p53_13_S2277 | 5 nM | 38 |
| p53_13_S2277 | 1 nM | 112 |
| p53_13_S2278 | 50 nM | 41 |
| p53_13_S2278 | 25 nM | 25 |
| p53_13_S2278 | 5 nM | 49 |
| p53_13_S2278 | 1 nM | 99 |
| p53_41_S709 | 50 nM | 5 |
| p53_41_S709 | 25 nM | 8 |
| p53_41_S709 | 5 nM | 14 |
| p53_41_S709 | 1 nM | 30 |
| p53_41_S2279 | 50 nM | 3 |
| p53_41_S2279 | 25 nM | 8 |
| p53_41_S2279 | 5 nM | 3 |
| p53_41_S2279 | 1 nM | 5 |
| p53_41_S2298 | 50 nM | 5 |
| p53_41_S2298 | 25 nM | 8 |
| p53_41_S2298 | 5 nM | 5 |
| p53_41_S2299 | 1 nM | |
| p53_41_S2299 | 50 nM | 3 |
| p53_41_S2299 | 25 nM | 3 |
| p53_41_S2299 | 5 nM | 5 |
| p53_41_S2299 | 1 nM | 5 |
| p53_41_S2300 | 50 nM | 3 |
| p53_41_S2300 | 25 nM | 3 |
| p53_41_S2300 | 5 nM | 2 |
| p53_41_S2300 | 1 nM | 3 |
| p53_44_S2301 | 50 nM | 5 |
| p53_44_S2301 | 25 nM | 5 |
| p53_44_S2301 | 5 nM | 3 |
| p53_44_S2301 | 1 nM | 14 |
| p53_44_S2302 | 50 nM | 3 |
| p53_44_S2302 | 25 nM | 3 |
| p53_44_S2302 | 5 nM | 5 |
| p53_44_S2302 | 1 nM | 8 |
| p53_44_S2303 | 50 nM | 3 |
| p53_44_S2303 | 25 nM | 5 |
| p53_44_S2303 | 5 nM | 3 |

TABLE F1-continued

| Sample Description (dsRNA compound used) | Concentration of dsRNA compound | p53 residual mRNA % of control |
|---|---|---|
| p53_44_S2303 | 1 nM | 3 |
| p53_44_S2304 | 50 nM | 5 |
| p53_44_S2304 | 25 nM | 5 |
| p53_44_S2304 | 5 nM | 11 |
| p53_44_S2304 | 1 nM | 19 |

The results of the in-vitro activity studies that were carried out in human HCT116 cells show that the compounds identified as p53_41_S709, p53_41_S2279, p53_41_S2298, p53_41_S2299, p53_44_S2301, p53_44_S2302, p53_44_S2303 and p53_44_S2304 (all described in Table E, supra) were found to be most active in down-regulating human p53 mRNA.

Table F2 summarizes the in vitro activity results obtained for some of the novel double-stranded nucleic acid molecules in rat REF52 cell line.

The in-vitro activity in Table F2 is demonstrated as the % residual target mRNA relative to control.

TABLE F2

| Sample Description (dsRNA compound used) | Concentration of dsRNA compound | p53 residual mRNA % of control |
|---|---|---|
| REF52 control | None | 100 |
| p53_13_S500 | 50 nM | 26 |
|  | 25 nM | 30 |
|  | 5 nM | 63 |
|  | 1 nM | 68 |
| p53_41_S709 | 50 nM | 40 |
|  | 25 nM | 87 |
|  | 5 nM | 96 |
|  | 1 nM | 211 |
| p53_41_S2279 | 50 nM | 38 |
|  | 25 nM | 20 |
|  | 5 nM | 21 |
|  | 1 nM | 60 |
| p53_41_S2298 | 50 nM | 137 |
|  | 25 nM | 81 |
|  | 5 nM | 71 |
|  | 1 nM | 113 |
| p53_41_S2299 | 50 nM | 116 |
|  | 25 nM | 122 |
|  | 5 nM | 107 |
|  | 1 nM | 153 |
| p53_41_S2300 | 50 nM | 102 |
|  | 25 nM | 81 |
|  | 5 nM | 112 |
|  | 1 nM | 149 |
| p53_44_S2301 | 50 nM | 12 |
|  | 25 nM | 14 |
|  | 5 nM | 25 |
|  | 1 nM | 55 |
| p53_44_S2302 | 50 nM | 14 |
|  | 25 nM | 9 |
|  | 5 nM | 18 |
|  | 1 nM | 59 |
| p53_44_S2303 | 50 nM | 20 |
|  | 25 nM | 12 |
|  | 5 nM | 12 |
|  | 1 nM | 38 |
| p53_44_S2304 | 50 nM | 22 |
|  | 25 nM | 33 |
|  | 5 nM |  |
|  | 1 nM |  |

The results of this in-vitro activity study that was carried out in rat REF52 cells show that the compounds identified as p53_44_S2301, p53_44_S2302, p53_44_S2303 and p53_44_S2304 (all described in Table E, supra) were found to be most active in down-regulating rat p53 mRNA, amongst the compounds that were tested in this study.

Example 4: Evaluation of the Potential Activity of Novel Double-Stranded RNA Molecules Using psiCHECK™-2—System Three psiCHECK™-2-based (Promega) constructs were prepared for the evaluation of the potential activity. The psiCHECK constructs contained single copies of matched complementary guide (AS-CM). 1.3-1.5×10$^6$ human HeLa cells were inoculated in 10 cm dish. Cells were then incubated in 37±1° C., 5% $CO_2$ incubator for 24 hours. Growth medium was replaced one day post inoculation by 8 ml fresh growth medium and each plate was transfected with one of the plasmids mentioned above, using Lipofectmine™ 2000 reagent according to manufacturer protocol and incubated for 5 hours at 37±1° C. and 5% $CO_2$. Following incubation, cells were re-plated in a 96-well plate at final concentration of 5×10$^3$ cells per well in 80 μl growth medium. After 16 hour, cells were transfected with transfection RNA compound using Lipofectamine 2000 reagent at final concentrations ranging from 0.01 nM to 100 nM in a 100 μl final volume. Cells were then incubated for 48 hours at 37±1° C. following assessment of Renilla and FireFly luciferase activities as described below.

48 hours following transfection with double-stranded RNA compound, Renilla and FireFly luciferase activities were measured in each of the siRNA transfected samples, using Dual-Luciferase® Assay kit (Promega, Cat # E1960) according to manufacturer procedure. Renilla luciferase activity value was divided by Firefly luciferase activity value for each sample (normalization). Renilla luciferase activity is finally expressed as the percentage of the normalized activity value in tested sample relative to the normalized value obtained in cells transfected with the corresponding psiCHECK™-2 plasmid only but with no double-stranded RNA.

Tables G, H and I summarizes the results (% residual mRNA) obtained for some of the novel double-stranded nucleic acid molecules using the psiCHECK system on the AS-CM sequence. All the novel double-stranded nucleic acid compounds are described in Table E, supra.

Tables G, H and I summarizes the results (% residual mRNA) obtained for some of the novel double-stranded nucleic acid molecules using the psiCHECK system on the AS-CM sequence. All the novel dsRNA compounds are described in Table E, supra.

TABLE G

| Sample Description (dsRNA compound used) | Concentration of dsRNA compound | AS_CM p53 residual mRNA % of control |
|---|---|---|
| None (control) |  | 100 |
| TP53_41_S709 | 100 nM | 6 |
| TP53_41_S709 | 33.3 nM | 5 |
| TP53_41_S709 | 11.1 nM | 7 |
| TP53_41_S709 | 5 nM | 9 |
| TP53_41_S709 | 3.7 nM | 9 |
| TP53_41_S709 | 1.23 nM | 11 |
| TP53_41_S709 | 0.41 nM | 13 |
| TP53_41_S709 | 0.137 nM | 22 |
| TP53_41_S709 | 0.045 nM | 26 |
| TP53_41_S709 | 0.015 nM | 33 |
| TP53_41_S709 | 0.005 nM | 28 |
| TP53_41_S2279 | 100 nM | 3 |
| TP53_41_S2279 | 33.3 nM | 3 |
| TP53_41_S2279 | 11.1 nM | 3 |
| TP53_41_S2279 | 3.7 nM | 4 |

TABLE G-continued

| Sample Description (dsRNA compound used) | Concentration of dsRNA compound | AS_CM p53 residual mRNA % of control |
|---|---|---|
| TP53_41_S2279 | 1.23 nM | 5 |
| TP53_41_S2279 | 0.41 nM | 5 |
| TP53_41_S2279 | 0.137 nM | 9 |
| TP53_41_S2279 | 0.045 nM | 12 |
| TP53_41_S2279 | 0.015 nM | 29 |
| TP53_41_S2279 | 0.005 nM | 34 |
| TP53_41_S2298 | 100 nM | 4 |
| TP53_41_S2298 | 33.3 nM | 4 |
| TP53_41_S2298 | 11.1 nM | 5 |
| TP53_41_S2298 | 3.7 nM | 5 |
| TP53_41_S2298 | 1.23 nM | 7 |
| TP53_41_S2298 | 0.41 nM | 11 |
| TP53_41_S2298 | 0.137 nM | 18 |
| TP53_41_S2298 | 0.045 nM | 36 |
| TP53_41_S2298 | 0.015 nM | 50 |
| TP53_41_S2298 | 0.005 nM | 57 |
| TP53_41_S2299 | 100 nM | 3 |
| TP53_41_S2299 | 33.3 nM | 3 |
| TP53_41_S2299 | 11.1 nM | 4 |
| TP53_41_S2299 | 3.7 nM | 5 |
| TP53_41_S2299 | 1.23 nM | 6 |
| TP53_41_S2299 | 0.41 nM | 8 |
| TP53_41_S2299 | 0.137 nM | 15 |
| TP53_41_S2299 | 0.045 nM | 27 |
| TP53_41_S2299 | 0.015 nM | 36 |
| TP53_41_S2299 | 0.005 nM | 47 |
| TP53_41_S2300 | 100 nM | 9 |
| TP53_41_S2300 | 33.3 nM | 9 |
| TP53_41_S2300 | 11.1 nM | 10 |
| TP53_41_S2300 | 3.7 nM | 12 |
| TP53_41_S2300 | 1.23 nM | 11 |
| TP53_41_S2300 | 0.41 nM | 18 |
| TP53_41_S2300 | 0.137 nM | 24 |
| TP53_41_S2300 | 0.045 nM | 39 |
| TP53_41_S2300 | 0.015 nM | 53 |
| TP53_41_S2300 | 0.005 nM | 65 |

TABLE H

| Sample Description (dsRNA compound used) | Concentration of dsRNA compound | AS_CM p53 residual mRNA % of control |
|---|---|---|
| None (control) | | 100 |
| p53_13_S500 | 100 nM | 6 |
| p53_13_S500 | 33.3 nM | 5 |
| p53_13_S500 | 11.1 nM | 6 |
| p53_13_S500 | 3.7 nM | 8 |
| p53_13_S500 | 5 nM | 5 |
| QHMon1 | 1.23 nM | 9 |
| p53_13_S500 | 0.41 nM | 11 |
| p53_13_S500 | 0.137 nM | 22 |
| p53_13_S500 | 0.045 nM | 34 |
| p53_13_S500 | 0.015 nM | 38 |
| p53_13_S500 | 0.005 nM | 48 |
| TP53_13_S2275 | 100 nM | 3 |
| TP53_13_S2275 | 33.3 nM | 3 |
| TP53_13_S2275 | 11.1 nM | 4 |
| TP53_13_S2275 | 3.7 nM | 4 |
| TP53_13_S2275 | 1.23 nM | 6 |
| TP53_13_S2275 | 0.41 nM | 6 |
| TP53_13_S2275 | 0.137 nM | 8 |
| TP53_13_S2275 | 0.045 nM | 14 |
| TP53_13_S2275 | 0.015 nM | 18 |
| TP53_13_S2275 | 0.005 nM | 30 |
| TP53_13_S2276 | 100 nM | 2 |
| TP53_13_S2276 | 33.3 nM | 2 |
| TP53_13_S2276 | 11.1 nM | 2 |
| TP53_13_S2276 | 3.7 nM | 3 |
| TP53_13_S2276 | 1.23 nM | 3 |
| TP53_13_S2276 | 0.41 nM | 4 |
| TP53_13_S2276 | 0.137 nM | 6 |
| TP53_13_S2276 | 0.045 nM | 14 |
| TP53_13_S2276 | 0.015 nM | 22 |
| TP53_13_S2276 | 0.005 nM | 25 |

TABLE H-continued

| Sample Description (dsRNA compound used) | Concentration of dsRNA compound | AS_CM p53 residual mRNA % of control |
|---|---|---|
| TP53_13_S2277 | 100 nM | 3 |
| TP53_13_S2277 | 33.3 nM | 3 |
| TP53_13_S2277 | 11.1 nM | 3 |
| TP53_13_S2277 | 3.7 nM | 3 |
| TP53_13_S2277 | 1.23 nM | 4 |
| TP53_13_S2277 | 0.41 nM | 5 |
| TP53_13_S2277 | 0.137 nM | 7 |
| TP53_13_S2277 | 0.045 nM | 14 |
| TP53_13_S2277 | 0.015 nM | 24 |
| TP53_13_S2277 | 0.005 nM | 32 |
| TP53_13_S2278 | 100 nM | 2 |
| TP53_13_S2278 | 33.3 nM | 2 |
| TP53_13_S2278 | 11.1 nM | 3 |
| TP53_13_S2278 | 3.7 nM | 2 |
| TP53_13_S2278 | 1.23 nM | 3 |
| TP53_13_S2278 | 0.41 nM | 3 |
| TP53_13_S2278 | 0.137 nM | 7 |
| TP53_13_S2278 | 0.045 nM | 14 |
| TP53_13_S2278 | 0.015 nM | 18 |
| TP53_13_S2278 | 0.005 nM | 27 |

TABLE I

| Sample Description (dsRNA compound used) | Concentration of dsRNA compound | AS_CM p53 residual mRNA % of control |
|---|---|---|
| None (control) | | 100 |
| TP53_44_S2301 | 100 nM | 5 |
| TP53_44_S2301 | 33.3 nM | 5 |
| TP53_44_S2301 | 11.1 nM | 6 |
| TP53_44_S2301 | 3.7 nM | 7 |
| TP53_44_S2301 | 1.23 nM | 9 |
| TP53_44_S2301 | 0.41 nM | 15 |
| TP53_44_S2301 | 0.137 nM | 27 |
| TP53_44_S2301 | 0.045 nM | 40 |
| TP53_44_S2301 | 0.015 nM | 47 |
| TP53_44_S2301 | 0.005 nM | 49 |
| TP53_44_S2302 | 100 nM | 3 |
| TP53_44_S2302 | 33.3 nM | 4 |
| TP53_44_S2302 | 11.1 nM | 4 |
| TP53_44_S2302 | 3.7 nM | 6 |
| TP53_44_S2302 | 1.23 nM | 6 |
| TP53_44_S2302 | 0.41 nM | 9 |
| TP53_44_S2302 | 0.137 nM | 19 |
| TP53_44_S2302 | 0.045 nM | 28 |
| TP53_44_S2302 | 0.015 nM | 34 |
| TP53_44_S2302 | 0.005 nM | 39 |
| TP53_44_S2303 | 100 nM | 6 |
| TP53_44_S2303 | 33.3 nM | 6 |
| TP53_44_S2303 | 11.1 nM | 6 |
| TP53_44_S2303 | 3.7 nM | 7 |
| TP53_44_S2303 | 1.23 nM | 7 |
| TP53_44_S2303 | 0.41 nM | 13 |
| TP53_44_S2303 | 0.137 nM | 24 |
| TP53_44_S2303 | 0.045 nM | 46 |
| TP53_44_S2303 | 0.015 nM | 47 |
| TP53_44_S2303 | 0.005 nM | 73 |
| TP53_44_S2304 | 100 nM | 4 |
| TP53_44_S2304 | 33.3 nM | 4 |
| TP53_44_S2304 | 11.1 nM | 4 |
| TP53_44_S2304 | 3.7 nM | 5 |
| TP53_44_S2304 | 1.23 nM | 6 |
| TP53_44_S2304 | 0.41 nM | 11 |
| TP53_44_S2304 | 0.137 nM | 24 |
| TP53_44_S2304 | 0.045 nM | |
| TP53_44_S2304 | 0.015 nM | 37 |
| TP53_44_S2304 | 0.005 nM | 31 |

The results of the activity study in psiCHECK™-2—System show that all double-stranded nucleic acid compounds based on TP53_41 sequence, TP53_13 sequence and TP53_44 sequence were found to be highly active.

Example 5: Animal Models

Testing the active siRNAs of the invention may be done in predictive animal models.

Model systems of acute renal failure (ARF)

Testing the active nucleic acid compounds disclosed herein for treating acute renal failure (ARF) may be done using sepsis-induced ARF or ischemia-reperfusion-induced ARF.

1. Sepsis Induced ARF

Two predictive animal models of sepsis-induced ARF are described by Miyaji T, Hu X, Yuen P S, Muramatsu Y, Iyer S, Hewitt S M, Star R A, 2003, Ethyl pyruvate decreases sepsis-induced acute renal failure and multiple organ damage in aged mice, Kidney Int. November; 64(5):1620-31. These two models are lipopolysaccharide administration and cecal ligation puncture in mice, preferably in aged mice.

2. Ischemia-Reperfusion-Induced ARF

This predictive animal model is described by Kelly K J, Plotkin Z, Vulgamott S L, Dagher P C, 2003 January, P53 mediates the apoptotic response to GTP depletion after renal ischemia-reperfusion: protective role of a p53 inhibitor, J Am Soc Nephrol.; 14(1):128-38.

Ischemia-reperfusion injury is induced in rats following 45 minutes bilateral kidney arterial clamp and subsequent release of the clamp to allow 24 hours of reperfusion. 250 µg of a test nucleic acid compound is injected into the jugular vein 2 hrs prior to and 30 minutes following the clamp. Additional 250 µg of test nucleic acid compound are given via the tail vein at 4 and 8 hrs after the clamp. Nucleic acid compound against GFP serves as a negative control. ARF progression is monitored by measurement of serum creatinine levels before and 24 hrs post surgery. At the end of the experiment, the rats are perfused via an indwelling femoral line with warm PBS followed by 4% paraformaldehyde. The left kidneys are removed and stored in 4% paraformaldehyde for subsequent histological analysis. Acute renal failure is frequently defined as an acute increase of the serum creatinine level from baseline. An increase of at least 0.5 mg per dL or 44.2 µmol per L of serum creatinine is considered as an indication for acute renal failure. Serum creatinine is measured at time zero before the surgery and at 24 hours post ARF surgery.

To study the distribution of the nucleic acid compound in the rat kidney, Cy3-labeled nucleic acid compound molecules (2 mg/kg) are administered iv for 3-5 min, after which in vivo imaging is conducted using two-photon confocal microscopy.

The effect of the nucleic acid compound on renal ischemia-reperfusion injury is further determined by analyzing the extent of tubular necrosis in the renal tissue. Tubular necrosis may be scored as: no damage (damage scoring 0), unicellular, patchy isolated necrosis (damage scoring 1), tubular necrosis in less than 25% of the tissue (damage scoring 2), tubular necrosis in between 25 and 50% of the tissue (damage scoring 3) and tubular necrosis in more than 50% of the tissue (damage scoring 4).

The nucleic acid compounds of Tables A, B and E are tested in these models of acute renal failure (ARF), in which it is found that they are effective in treating ARF.

Model Systems of Chemotherapy-Induced Inner Ear Hair Cell Death

1. Model System of Carboplatin-Induced Inner Hair Cells Loss

Eight Chinchillas are pre-treated by direct administration of test nucleic acid compound in saline (1, 10 and 30 µg) to the left ear of each animal Saline is given to the right ear of each animal as placebo. Two days following the administration of nucleic acid compound, the animals are treated with carboplatin (75 mg/kg ip). After sacrifice of the chinchillas (two weeks post carboplatin treatment) the % of dead cells of inner hair cells (IHC) and outer hair cells (OHC) is calculated in the left ear (nucleic acid compound treated) and in the right ear (saline treated).

2. Model System of Cisplatin-Induced Inner Hair Cells Loss

Male Wistar rats are tested for basal auditory brainstem response (ABR) thresholds for signals of clicks, 8, 16 and 32 kHz prior to cisplatin treatment. Following the basal auditory brainstem response testing, cisplatin is administered as an intraperitoneal infusion of 13 mg/kg over 30 minutes. Treated ears receive 15 ug/4 microliters of a test nucleic acid compound in PBS. Control ears are treated with either non-related GFP nucleic acid compound or PBS. The nucleic acid compound molecules are administered between 3-5 days prior to cisplatin administration in order to permit protective effect on the cochlea.

The auditory brainstem response (ABR) testing is repeated 3 days after cisplatin administration. The auditory brainstem response thresholds are compared between pretreatment and posttreatment and the shift in thresholds are recorded. Higher shift in thresholds following cisplatin treatment is indicative for more severe hair cells loss in the cochlea. After the repeat of auditory brainstem response testing, animals are sacrificed and cochleae are removed and processed for scanning electron microscopy (SEM) to quantify outer hair cell (OHC) loss in the hook region (high frequency region). The % outer hair cell loss is calculated by dividing the number of missing or severely damaged cells by the total number of outer hair cells in the field of the photograph.

The nucleic acid compounds of Tables A, B and E are tested in these model of chemotherapy-induced inner hair cells loss in the cochlea, in which it is found that they are effective in significantly reducing hair cells loss in the cochlea and in treating chemotherapy-induced hearing loss.

Model System of Acoustic-Induced Hair Cell Death in the Cochlea

The activity of test nucleic acid compound in an acoustic trauma model is studied in chinchilla. A group of 7 animals undergo the acoustic trauma. The animals are exposed to an octave band of noise centered at 4 kHz for 2.5 h at 105 dB. The left ear of the noise-exposed chinchillas is pre-treated (48 h before the acoustic trauma) with 30 µg of nucleic acid compound in ~10 µL of saline; the right ear is pre-treated with vehicle (saline). The compound action potential (CAP) is a convenient and reliable electrophysiological method for measuring the neural activity transmitted from the cochlea. The CAP is recorded by placing an electrode near the base of the cochlea in order to detect the local field potential that is generated when a sound stimulus, such as click or tone burst, is abruptly turned on. The functional status of each ear is assessed 2.5 weeks after the acoustic trauma. Specifically, the mean threshold of the compound action potential recorded from the round window is determined 2.5 weeks after the acoustic trauma in order to determine if the thresholds in the nucleic acid-treated ear is lower (better) than the untreated (saline) ear. In addition, the amount of inner and outer hair cell loss is determined in the nucleic acid-treated and the control ear. These results indicate that p53 siRNA administered to the round window of the cochlea is capable of reducing the damage caused by acoustic trauma.

The nucleic acid compounds of Tables A, B and E are tested in this model of acoustic trauma-induced hearing loss, in which it is found that they are effective in reducing the damage caused by acoustic trauma and in treating acoustic trauma-induced hearing loss.

Additional Hearing Loss Models

A) Hearing Regeneration (Plasticity) Model in Guinea-Pig

Deafening is induced by systemically treating albino guinea pigs with a single is injection of kanamycin (450-500 mg/kg) followed by a single iv (jugular) injection of ethacrynic acid (EA). This pharmacological deafening eliminates bilaterally all hair cells approximately after 1-2 days and leaves the supporting cells differentiated. Therapeutic nucleic acids are applied to the middle ear by transtympanic injection (TT) or into the external auditory canal or eardrum by ear drops (ErD).

The efficacy of the test nucleic acid compounds is examined as follows:

1) Cochleae/s are morphologically analyzed as wholemounts stained for myosin VIIa (hair cell marker) and phalloidin.

2) BrdU incorporation is measured as an indicator of proliferation rate of hair cells.

B) Noise Induced Acute Hearing Loss Model in Guinea Pig

Noise can cause hearing damage with temporary or permanent sensorineural hearing loss (SNHL) and tinnitus. SNHL and tinnitus can occur singular or in combination. In humans, noise induced hearing loss (NIHL) is demonstrated by a threshold shift in the pure tone audiogram, in recruitment, in pathological results of supra-threshold hearing tests and in amplitude decline of oto-acoustic emissions. Hearing damage is induced by exposure to continuous noise or impulsive noise. In addition the possibility of impulse noise traumata or explosion trauma should be taken into consideration. Exposure to impulse noise can result in a more severe lesion of the inner ear than exposure to continuous noise. Important criteria for the development of noise damage are sound pressure level (SPL), level increase velocity, exposure time, as well as individual susceptibility ("the vulnerable inner ear"). Noise exposure usually leads to an elevation of threshold which may be later resolved in part, such that the temporary component is called "temporary threshold shift" (TTS). If there isn't complete restitution in the recovery phase after TTS, this may result in permanent inner ear damage (permanent threshold shift=PTS). Very high sound intensity may lead to immediate cellular death and mechanical rupture of structures in the inner ear and PTS.

In this model, a bilateral lesion is induced with noise exposure; Guinea pigs are exposed to 117 dB SPL broadband noises for 6 hours.

The nucleic acid compounds of Tables A, B and E are tested in this model, in which it is found that they are effective in preventing or treating hearing loss.

Model Systems of Pressure Sores or Pressure Ulcers

Pressure sores or pressure ulcers including diabetic ulcers, are areas of damaged skin and tissue that develop when sustained pressure (usually from a bed or wheelchair) cuts off circulation to vulnerable parts of the body, especially the skin on the buttocks, hips and heels. The lack of adequate blood flow leads to ischemic necrosis and ulceration of the affected tissue. Pressure sores occur most often in patients with diminished or absent sensation or who are debilitated, emaciated, paralyzed, or long bedridden. Tissues over the sacrum, ischia, greater trochanters, external malleoli, and heels are especially susceptible; other sites may be involved depending on the patient's situation.

Testing the active nucleic acid compounds for treating pressure sore, ulcers and similar wounds is performed in the mouse model described in Reid et al., (J Surgical Research. 116:172-180, 2004).

An additional rabbit model (described by Mustoe et al, (JCI, 1991. 87(2):694-703; Ahn and Mustoe, Ann Pl Surg, 1991. 24(1):17-23) is used for testing the nucleic acid compounds. are tested in animal models where it is shown that these siRNA compounds treat and prevent pressure sores and ulcers.

The nucleic acid compounds of Tables A, B and E are tested in these models, in which it is found that they are effective in treating pressure sore, ulcers and similar wounds.

Model System of Delayed Graft Function (DGF) in a Kidney Transplant Patient

Warm ischemia—A left nephrectomy is performed, followed by auto transplantation that results in a warm kidney graft preservation period of 45 minutes. Following auto transplantation, a right nephrectomy is performed on the same animal. A test nucleic acid compound is administered intravenously via the femoral vein either before harvesting of the kidney graft (mimicking donor treatment) ("pre"), or after the kidney autotransplantation (mimicking recipient treatment), or both before harvest and after transplantation (combined donor and recipient treatment) ("pre-post").

Cold ischemia—A left nephrectomy is performed on a donor animal, followed by a cold preservation (on ice) of the harvested kidney for a period of 5 hours. At the end of this period, the recipient rat undergoes a bilateral nephrectomy, followed by transplantation of the cold-preserved kidney graft. The total warm ischemia time (including surgical procedure) is 30 minutes. A test nucleic acid compound is administered intravenously via the femoral vein, either to the donor animal prior to the kidney harvest ("pre"), or to the recipient animal 15 minutes ("post 15 min") or 4 hours (post 4 hrs) post-transplantation.

To assess the efficacy of the nucleic acid compound in improvement of post-transplantation renal function, serum creatinine levels are measured on days 1, 2, and 7 post-transplantation in both warm and cold ischemia models.

The nucleic acid compounds of Tables A, B and E are tested in this model of DGF (delayed graft function), in which it is found that they are effective in protect the kidney from DGF (delayed graft function) associated with cold and warm ischemia and subsequent reperfusion.

Model Systems of Chronic Kidney Disease (CKD)

Testing the active nucleic acid compounds disclosed herein for treating chronic kidney disease (CKD) may be done using the following models:

This animal model is useful in assessing the test compounds for prevention of CKD or attenuation of CKD progression resulting from repetitive AKI/ARF insults.

Repetitive AKI/ARF insults often results in the exacerbation of chronic kidney disease (CKD), progression of CKD or development of CKD. ARF is a clinical syndrome characterized by rapid deterioration of renal function that occurs within days. Without being bound by theory the acute kidney injury may be the result of renal ischemia-reperfusion injury such as renal ischemia-reperfusion injury in patients undergoing major surgery such as major cardiac surgery. The principal feature of ARF is an abrupt decline in glomerular filtration rate (GFR), resulting in the retention of nitrogenous wastes (urea, creatinine) in the blood. Recent studies, support that apoptosis in renal tissues is prominent in most human cases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum.

The rat model for CKD comprises repetitive (5 times) ischemia-reperfusion-induced ARF as follows: Ischemia-reperfusion injury is induced in rats following 45 minutes bilateral kidney arterial clamp and subsequent release of the clamp to allow 24 hours of reperfusion. PBS or test nucleic acid compound (12 mg/kg) are injected i.v. into individual experimental animals 4 hours post clamp. ARF progression is monitored by measurement of serum creatinine (SCr) levels before (baseline) and 24 hrs, 2 days and 7 days post surgery. The treatment (I/R injury, test nucleic acid compound, SCr measurement) is repeated for four more cycles at 30-day intervals, for a total of five cycles. At 7 days post 5th cycle 24 hour creatinine clearance (CrCl) metabolic cage and urine protein are measured. The right kidneys are surgically removed 2 days after metabolic cage (day 10 post 5th cycle) and the kidney are histologically analyzed for CKD. At 3 weeks post right nephrectomy the left kidney is exteriorized and studied in vivo using intravital two-photon microscopy (for Cy3-siRNa uptake and retention).

The nucleic acid compounds of Tables A, B and E are tested in this model of CKD, in which it is found that they are effective in treating CKD.

Model Systems of Spinal Cord Injury (SCI)

Animals and spinal cord injury: The experiments are performed using 125 Sprague-Dawley female rats (10-11 weeks old) (Taconic, Germantown, N.Y.). For SCI surgery, rats are anesthetized with 2% isoflurane (IsoFlo, Abbott Lab, North Chicago, Ill.) and the spinal cord is exposed by laminectomy at T9-10 and then contused by dropping a 10.0 g rod on the exposed T11 cord from a height of 12.5 or 25 mm, as described (Constantini and Young, 1994; Hasegawa et al., 2005). Following the contusion and injections when performed, muscles and skin are closed separately. Cefazolin (25 mg/kg) is administered to all rats.

Injection of a test nucleic acid compound: Injections at the injury site are performed within 30 minutes prior to injury; 1 μg in 1 μl of nucleic acid compound is injected at each of three points including the injury epicenter, and 2 mm rostral and caudal to the epicenter (3 μl total) (Hasegawa et al., 2005). Each injection is conducted slowly during a period of ~10 min at a depth of ~1 mm using a sterile 5-μl Hamilton syringe. For lumbar puncture, anesthetized rats are placed on an operating surface that flexed their backs and raised the lumbar region. A ~1 cm longitudinal incision is made over the L3-5 spinal processes, and the skin is retracted. A 30-gauge needle is advanced into the spinal canal at L3-4 or L4-5 to administer 40 μl into the intrathecal space using a 100 μl Hamilton syringe. Proper placement of the needle in the lumbar intrathecal space is indicated by a feeling of "give" at the time of entry and a tail flick (Lepore et al., 2005). To determine whether this method reverses cerebrospinal fluid (CSF) flow up to the region of the injury site, 40 μl of Evans Blue dye is injected in the lumbar enlargement and the appearance of the dye in exposed T9-10 spinally laminectomized rats within seconds after injection confirmed flow across the injury site.

Total cellular RNA preparation and Q-RT-PCR: To isolate RNAs, animals are injected with 100 mg/kg pentobarbital and then perfused with cold PBS. Spinal columns are quickly removed and frozen on dry ice powder. A 5-mm spinal cord segment centered at injury (I) epicenter is dissected along with adjacent 5-mm proximal and distal segments as well as a segment at thoracic level 1 (T1) (Chang et al., 2009). In some experiments the I segments is bisected at the midline yielding two pieces of tissue representing the same region of the spinal cord and separate extractions for RNA and protein enabled comparison of results from the paired tissues. For RNA, tissues are homogenized with a polytron homogenizer (Kinematica Inc.) and RNA is prepared following the Qiagen RNeasy Plus Mini protocol (Qiagen, Valencia, Calif.). RNA is quantitated using a Nanodrop spectrophotometer (Thermo Scientific Inc.) and 1 μg of total RNA is used for first-strand cDNA with SuperScript II reverse transcriptase (Invitrogen, Carlsbad, Calif.) primed by random hexamers. PCR reactions are performed on 40 ng of cDNA using 1 mM of primers and SYBR Green master mix (Applied Biosystems, Foster City, Calif.) in 20 μl reactions using Applied Biosystems 7500 Fast machine. The expression value of each gene is normalized to the amount of GAPDH cDNA to calculate the relative amount of RNA present in each sample.

Tissue processing and staining: Anesthetized animals are perfused intracardially with saline solution followed by 4% paraformaldehyde. Spinal cords are removed with injury epicenter marked and post-fixed 4-5 h in the same fixative, cryoprotected, embedded for frozen sectioning and cut at 20 μm on a cryostat (Hacker-Bright). Cy3.5 labeled nucleic acid compound is detected in freshly isolated spinal cord with a Zeiss Stemi SV11 microscope to determine gross distributions. Spinal cords are then fixed in 4% paraformaldehyde and cryosectioned. LFB staining and other procedures are performed as described (Hasegawa et al., 2005). For immunostaining, sections are blocked with 10% normal goat serum/0.3% Triton X-100 in PBS for 2 h at and incubated overnight at 4° C. with primary antibodies. Staining with rabbit protein kinase C-γ (PKCγ) (1:200) and mouse ED1 (1:300) (Serotec, Raleigh, N.C.) are performed on the same sections following antigen retrieval with proteinase K (Dako) for 4 min at 25° C. Sections are washed with PBS and incubated with secondary anti-rabbit Alexa 488 or anti-mouse Alexa 568 at 1:400 for 1 h at room temperature. After washing, sections are mounted with Aqua-Mount (Lerner Lab). Images are captured using a Zeiss 510 confocal laser scanning microscope (LSM) or a Zeiss Automated Cell scan System for Axiovert 200 M on groups of sections that are stained at the same time. Staining with Serotonin rabbit 5-HT (1:1000) (ImmunoStar) is performed using the same procedure without antigen retrieval and with anti rabbit Alexa 568 (1:200) as secondary antibody.

Quantitation for histology: Quantitation of LFB staining is used to analyze tissue sparing. All coronal sections for the analysis are stained for LFB at the same time to ensure uniform color development and then scanned with a Film Scanner LS-8000 ED (Nikon, Japan) at 4000 dpi resolution. The color images are converted to gray scale and individual sections were outlined in Photoshop, and NIH Image J is used to obtain the total area pixels for each section. A constant threshold is used to obtain super-threshold pixels of LFB staining and the resulting areas are measured. Spared tissue is defined as the super-threshold area divided by the total area outlined in each section. Images from each spinal cord are measured at 1 mm intervals over 10 mm of the spinal cord centered on the injury epicenter. In nearly all cases the position with minimal spared tissue corresponds to the designated injury epicenter and when it does not it is redefined as the 0 location. Averages of spared tissue are then calculated and plotted as a function of location. For ED1 staining, 11 coronal sections at 1 mm intervals are chosen from each animal for quantitation. Tiled images encompassing entire coronal sections at each location are taken with a 20× objective lens (N.A.=0.75) on an Axiovert 200M fluorescence microscope (Zeiss) and analyzed with Zeiss LSM histogram software. A constant threshold is applied to all sections and the super-threshold area for each is divided by the total area outlined to obtain the percent ED1+. The CST is located at the midline above the central canal and PKCγ staining in this region is outlined and extracted for quantitation. Super-threshold areas of each CST extracted region is obtained after excluding areas of autofluorescence due to macrophages and then normalizing. All quantitative analyses are performed by investigators blinded to the treatment groups.

The nucleic acid compounds of Tables A, B and E are tested in this model of SCI, in which it is found that they are effective in treating SCI.

Model Systems of Ischemia Reperfusion Injury Following Lung Transplantation in Rats Lung ischemia/reperfusion injury is achieved in a rat animal model as described in Mizobuchi et al., The Journal of Heart and Lung Transplantation, Vol 23 No. 7 (2004) and in Kazuhiro Yasufuku et al., Am. J. Respir. Cell Mol Biol, Vol 25, pp 26-34 (2001).

Specifically, after inducing anesthesia with isofluorane, the trachea is cannulated with a 14-gauge Teflon catheter and the rat is mechanically ventilated with rodent ventilator using 100% oxygen, at a rate of 70 breaths per minute and 2 cm H2O of positive end-respiratory pressure. The left pulmonary artery, veins and main stem bronchus are occluded with a Castaneda clamp. During the operation, the lung is kept moist with saline and the incision is covered to minimize evaporative losses. The period of ischemia is 60 minutes long. At the end of the ischemic period the clamp is removed and the lung is allowed to ventilate and reperfuse for further 4 h, 24 h, and 5 d post induction of lung ischemia. At the end of the experiment, the lungs are gently harvested and either frozen for RNA extraction or fixed in glutaraldehyde cocktail for subsequent histological analysis.

The nucleic acid compounds of Tables A, B and E are tested in this model, in which it is found that they are effective in treating ischemia reperfusion injury following lung transplantation.

Model System of Bone Marrow Transplantation (BMT)

The following model system of BMT described in Kelly R M et al. Blood. 2010 Feb. 4; 115(5): 1088-1097, may be used:

Animals: C57BL/6 (H-$2^b$; termed B6), [C57BL/6×Balb/c]F$_1$ (H-$2^{d/b}$; termed CB6F1) female mice, BALB/c (H-$2^d$) or C57BL/6.Ly5.1 mice and Bim$^{-/-}$ mice, backcrossed more than 10 generations onto B6 background, are used. A test nucleic acid compound is administered intraperitoneally in phosphate-buffered saline (PBS) 30 to 45 minutes before radiation. The selected dose/timing of test nucleic acid compound administration provides optimal inhibition of p53 function with minimal toxicity.

BMT: Single-cell suspensions of BM cells from B6.Ly5.1 (congenic) or BALB/c (allogeneic) donors are depleted of T cells to greater than 98% purity. CD4/8-depleted BM cells ($10^7$ [allogeneic] or 5×$10^6$ [congenic]) are administered intravenously to recipients that had received 9 Gy (C57BL/6) or 10 Gy (CB6F1) TBI from an x-ray source 24 hours before.

Lymphocyte analysis by fluorescence-activated cell sorting: Single-cell suspensions of thymocytes, splenocytes, and LNs are prepared by gentle dissociation, washed, filtered, resuspended in 2% fetal calf serum/PBS, and incubated with fluorochrome-conjugated monoclonal antibodies for 30 minutes at 4° C. Antibodies used are directed against CD4, CD8, CD3, T-cell receptor β), CD11c, B220, CD45.1, CD62L, and CD44 (eBioscience). Live events (≥105) are acquired on a BD FACSCanto and analyzed with FlowJo software (TreeStar).

Thymic epithelial cell (TEC) analysis by fluorescence-activated cell sorting: TECs are isolated. Individual thymi are incubated at 37° C. twice in collagenase-D/DNase-I and twice in collagenase/dispase/DNase-I (Roche). Pooled digestions are stained with anti-CD45-PerCp-Cy5.5, anti-EpCAM-PE, anti-Ly51/CDR1-biotin plus streptavidin-conjugated PE/Cy7, anti-MHC-II-Pacific Blue (eBioscience), and FITC-conjugated Ulex-europaeus-agglutinin-1 (UEA-1; Vector Laboratories). Mouse AIRE-specific rat mAb (5H12) is detected with mouse anti-rat IgG2c-Cy5. A total of 3×106 live events are acquired per sample.

Recent thymic emigrant detection: Anesthetized mice are injected in one thymic lobe with 50 μg sulfo-NHS-biotin (Pierce) in 10 μL PBS. After 24 hours, thymus and spleen are stained with streptavidin-conjugated PE/Cy7, CD4, CD8, CD3, CD45.1, CD44, and CD62L and are analyzed by flow cytometry.

Immunofluorescence microscopy: Tissues are embedded in OCT, snap-frozen in liquid nitrogen. Acetone-fixed 8-μm thymic sections are blocked with 10% normal horse serum/PBS and stained with Ly51/CDR1-FITC and polyclonal rabbit anti-mouse CK5 (Covance Research Products) plus Cy5-conjugated goat anti-rabbit immunoglobulin G (IgG; Invitrogen). For LN/spleen analysis, 6-cryosections are acetone-fixed and stained for glycoprotein-38 (gp38; purified clone 8.1.1; ATCC) or CCL21 (R&D Systems) along with B220-FITC (clone RA3-6B2; BD) for 3 hours at room temperature. CCL21 and gp38 signals are amplified with Tyramide Signal Amplification kit according to the manufacturer's instructions (Invitrogen). Slides are mounted with VECTASHIELD (Vector Laboratories) and images are acquired through a 10×/0.40 Olympus UPlanApo or 40×/0.80 Olympus UPlanApo Oil lens and an Olympus FV500 camera, compiled with Fluoview software (v.4.3), then analyzed and cropped in Adobe Photoshop CS2.

Lm infection and determination of CFU in organs: Recombinant Lm strains Lm-OVA and ΔactA-Lm-OVA (attenuated) expressing full-length chicken ovalbumin (OVA) are used. Mice are inoculated with early logarithmic-phase bacteria grown in brain heart infusion (BHI) broth at 37° C. Congenic BM transplant recipients were infected with $10^6$ colony-forming units (CFUs) of ΔactA-Lm-OVA and rechallenged with $10^5$ CFU of Lm-OVA. For allogeneic BMT studies, mice are intravenously immunized with 5×$10^4$ CFU and rechallenged with 2×$10^6$ CFU of Lm 2C. Three days after secondary infection, livers/spleens are homogenized in 0.05% Triton X-100/PBS, plated onto BHI plates, and Lm colonies are enumerated after 24 hours at 37° C.

Quantification of Lm-OVA-specific CD8 T cells: MHC-I-DimerX:mouse-Ig-PE (BD PharMingen) and purified OVA257-64 (SIINFEKL) peptide (Anaspec) are mixed to form MHC-I-DimerX:mouse-Ig:OVA257-64-PE conjugates according to the manufacturer's instructions and incubated with red blood cell-lysed peripheral blood for 1 hour at 4° C., washed, and then incubated with antibodies against surface markers. More than 104 donor CD8 T cells are collected per sample.

The nucleic acid compounds of Tables A, B and E are tested in this model, in which it is found that they are effective in restoring thymic function after BMT.

Model System of Stimulation of Hematopoiesis

The following model described in Leonova K I et al. Cell Cycle 9:7, 1434-1443; Apr. 1, 2010 may be used:

Two strains of wild type mice C57Bl/6 and Balb/c are used. Mice are given a single intraperitoneal (i.p.) injection of a test nucleic acid compound or vehicle immediately before exposure to lethal doses of total body gamma irradiation (TBI, 9 Gy for C57Bl/6 and 8 Gy for Balb/c). Mice survival rate is recorded. The doses of TBI used in this experiment are known to cause death primarily through damage to the hematopoietic (HP) system, as compared to higher doses that invoke gastrointestinal and cerebrovascular damage as well as HP damage. Therefore, the effect of a test nucleic acid compound on survival of irradiated mice in this experiment indicates that the compound acts as a radioprotectant of the HP system.

The nucleic acid compounds of Tables A, B and E are tested in this model, in which it is found that they are effective in protected hematopoietic stem cells (HSCs) and early progenitor cells (HPCs) capable of fully repopulating the HP system for long-term function.

Although the above examples have illustrated particular ways of carrying out embodiments of the invention, in practice persons skilled in the art will appreciate alternative ways of carrying out embodiments of the invention, which are not shown explicitly herein. It should be understood that the present disclosure is to be considered as an exemplification of the principles of this invention and is not intended to limit the invention to the embodiments illustrated.

Those skilled in the art will recognize, or be able to ascertain using no more than routine experimentation, equivalents of the specific embodiments of the invention described herein. Such equivalents are intended to be encompassed by the following claims.

We claim:

1. A double-stranded nucleic acid molecule comprising a sense strand and an antisense strand, the molecule having the structure:

(A)

```
sense strand (SEQ ID NO: 19)
5' z"-GGGCCUGACUCAGACUGAU-z' 3'
    |||||||||||||||||||
3' Z-CCCGGACUGAGUCUGACUA 5'
antisense strand (SEQ ID NO: 32);
``` wherein each one of A, C, G, U is independently an unmodified ribonucleotide, a modified ribonucleotide, an unmodified deoxyribonucleotide, a modified deoxyribonucleotide, or an unconventional moiety selected from the group consisting of a mirror nucleotide, an unmodified deoxyribonucleotide, a modified deoxyribonucleotide, a threose nucleic acid (TNA), a nucleotide analogue and a ribonucleotide joined to an adjacent ribonucleotide by a 2'-5' internucleotide phosphate bond;

wherein each "|" represents base pairing between the antisense and the corresponding sense strand;

wherein the antisense strand comprises a 2'-O-methyl sugar modified ribonucleotide at position 3 from the 5' terminus; and wherein the sequence of the sense strand is complementary to the sequence of the antisense strand; with the proviso that not each nucleotide is a deoxyribonucleotide; or a pharmaceutically acceptable salt of such molecule wherein Z' is a non-nucleotide overhang covalently attached at the 3' terminus of the sense strand, comprising a 1,3-propanediol mono(dihydrogen phosphate), represented as C3;

wherein z" is a non-nucleotide overhang covalently attached at the 5' terminus of the sense strand, comprising a C3;

wherein Z is a non-nucleotide overhang covalently attached at the 3' terminus of the antisense strand, comprising a C3-C3; and wherein the 3' termini of the sense and antisense strands are phosphorylated, represented by pi.

2. The molecule or the pharmaceutically acceptable salt of such molecule of claim 1, wherein a modified ribonucleotide on the sense and antisense strand, in addition to the 2'-O-methyl sugar modified ribonucleotides at position 3 on the antisense strand, comprises a modification at the 2' position of the sugar moiety, in particular wherein the modified ribonucleotide is a 2'-O-methyl sugar modified ribonucleotide.

3. A composition comprising the molecule or the pharmaceutically acceptable salt of such molecule of claim 1; and a pharmaceutically acceptable carrier.

4. A method for treating a subject suffering from a disease or disorder associated with a p53 expression, comprising,
administering a composition comprising the molecule or the pharmaceutically acceptable salt of such molecule of claim 1 to the subject, wherein the molecule or pharmaceutically acceptable salt is administered in an amount sufficient to down-regulate expression of p53, thereby treating the disease or disorder.

5. The method of claim 4, wherein the disease or disorder is selected from the group consisting of ischemia-reperfusion injury, a hearing impairment, a hearing disorder, a balance impairment, a hearing loss, chemotherapy-induced alopecia, radiation therapy-induced alopecia, an acute renal failure, an acute kidney injury, a chronic kidney disease (CKD), a side effect associated with anti-cancer therapy, Delayed Graft Function (DGF) in a kidney transplant patient, a spinal cord injury, a brain injury, a seizure, a stroke, a neurodegenerative disorder, Parkinson's disease, Alzheimer's disease, a tumor, a burn, a wound, hyperthermia, hypoxia, ischemia, organ transplantation, bone marrow transplantation (BMT), myocardial infarction/heart attack, cardiotoxicity, a p53-positive cancer, and acute liver failure.

6. A method for treating a p53-positive cancer in a subject comprising administering a composition comprising the molecule or the pharmaceutically acceptable salt of such molecule of claim 1 to the subject, wherein the composition is administered in an amount sufficient to down-regulate expression of a p53 gene, and thereby sensitize the p53-positive cancer to chemotherapy in the subject.

7. A method for hematopoietic progenitor expansion or stimulation of hematopoiesis in a subject comprising administering to the subject a composition comprising the molecule or the pharmaceutically acceptable salt of such molecule of claim 1.

8. A method for homing of p53-null Hematopoietic Stem Cell (HSC) in a subject comprising administering to the subject the molecule or the pharmaceutically acceptable salt of such molecule of claim 1.

9. The composition of claim 1, wherein the antisense strand comprises at least three 2'-O-methyl sugar modified ribonucleotides.

10. The composition of claim 1, wherein the antisense strand comprises at least one ribonucleotide joined to an adjacent ribonucleotide by a 2'-5' internucleotide phosphate bond.

11. The composition of claim 10, wherein the ribonucleotide joined to an adjacent ribonucleotide by a 2'-5' internucleotide phosphate bond is at position 6 or 7 from the 5' terminus of the antisense strand.

* * * * *

```
                             SEQUENCE LISTING

<160> NUMBER OF SEQ ID NOS: 33

<210> SEQ ID NO 1
<211> LENGTH: 2586
<212> TYPE: RNA
<213> ORGANISM: Homo_Sapiens

<400> SEQUENCE: 1 gauuggguu   uuccccuccc   augugcucaa   gacuggcgcu   aaaaguuuug   agcuucucaa     60
aagucuagag   ccaccgucca   gggagcaggu   agcugcuggg   cuccggggac   acuuugcguu    120
cgggcuggga   gcgugcuuuc   cacgacggug   acacgcuucc   cuggauuggc   agccagacug    180
ccuuccgggu   cacugccaug   gaggagccgc   agucagaucc   uagcgucgag   cccccucuga    240
gucaggaaac   auuuucagac   cuauggaaac   uacuuccuga   aaacaacguu   cugucccccu    300
ugccguccca   agcaauggau   gauuugaugc   ugucccccgga   cgauauugaa   caaugguuca    360
cugaagaccc   agguccagau   gaagcucccca   gaaugccaga   ggcugcuccc   cccguggccc    420
cugcaccagc   agcuccuaca   ccggcggccc   cugcaccagc   ccccuccugg   ccccugucau    480 cuucugucccc   uucccagaaa   accaccagg   gcagcuacgg   uuuccgucug   ggcuucuugc    540
auucugggac   agccaagucu   gugacuugca   cguacucccc   ugcccucaac   aagauguuuu    600
gccaacuggc   caagaccugc   ccugugcagc   uguggguuga   uuccacaccc   ccgcccggca    660
cccgcguccg   cgccauggcc   aucuacaagc   agucacagca   caugacggag   guugugaggc    720 gcugcccccca   ccaugagcgc   ugcucagaua   gcgauggucu   ggcccccuccu   cagcaucuua    780 uccgagugga   aggaaauuug   cguguggagu   auuuggauga   cagaaacacu   uuucgacaua    840 guguggugu   gcccuaugag   ccgccugagg   uuggcucuga   cuuaccacc   auccacuaca    900 acuacaugug   uaacaguucc   ugcaugggcg   gcaugaaccg   gaggcccauc   cucaccauca    960
ucacacugga   agacuccagu   gguaaucuac   ugggacggaa   cagcuuugag   gugcguguuu   1020
gugccugucc   ugggagagac   cggcgcacag   aggaagagaa   ucuccgcaag   aaaggggagc   1080
cucaccacga   gcugccccca   gggagcacua   agcgagcacu   gcccaacaac   accagcuccu   1140
cuccccagcc   aaagaagaaa   ccacuggaug   gagaauauuu   cacccuucag   auccgugggc   1200
gugagcgcuu   cgagauguuc   cgagagcuga   augaggccuu   ggaacucaag   gaugcccagg   1260
cugggaagga   gccaggggg   agcagggcuc   acuccagcca   ccugaagucc   aaaaaggguc   1320
agucuaccuc   ccgccauaaa   aaacaugu   ucaagacaga   agggcugac   ucagacugac   1380 auucuccacu   ucuuguuccc   cacugacagc   cucccacccc   caucucuccc   ucccccugcca   1440
```

```
uuuuggguuu uggguucuuug aacccuugcu ugcaauaggu gugcgucaga agcacccagg    1500
acuuccauuu gcuuuguccc ggggcuccac ugaacaaguu ggccugcacu ggguguuuugu    1560 ugugggagg aggauggga guaggacaua ccagcuuaga uuuuaagguu uuuacuguga       1620 gggaugu uug ggagauguaa gaaauguucu ugcaguaaag gguuaguuua caaucagcca    1680
cauucuaggu aggggcccac uucaccguac uaaccaggga agcugucccu cacuguugaa    1740
uuuucucuaa cuucaaggcc cauaucugug aaaugcuggc auuugcaccu accucacaga    1800
gugcauugug aggguuaaug aaauaaugua caucuggccu ugaaaccacc uuuuauuaca    1860
uggggucuag aacuugaccc ccuugagggu gcuuguuccc ucccguu ggucggug gg       1920 uugguaguuu cuacaguugg gcagcugguu aggagaggg aguugucaag ucucugcugg     1980
cccagccaaa cccugucuga caaccucuug ugaaccuua guaccuaaaa ggaaaucuca     2040
ccccauccca cacccuggag gauuucaucu cuuguauaug augaucugga uccaccaaga    2100
cuuguuuuau gcucagggguc aauuucuuuu ucuuuuuuuu uuuuuuuuuu ucuuuuucuu    2160
ugagacuggg ucucgcuuug uugcccaggc uggaguggag uggcgugauc uuggcuuacu    2220
gcagccuuug ccuccccggc ucgagcaguc cugccucagc ucccgagua gcugggacca     2280 cagguucaug ccaccauggc cagccaacuu ugcauguuu uguagagaug gggucucaca     2340
guguugccca ggcuggucuc aaacuccugg gcucaggcga uccaccuguc ucagccuccc    2400
agagugcugg gauuacaauu gugagccacc acguccagcu ggaaggguca acaucuuuuuа   2460 cauucugcaa gcacaucugc auuuucaccc cacccuuccc cuccuuccc cuuuuuauau     2520 cccauuuuua uaucgaucuc uuauuuuaca auaaaacuuu gcugccaccu gugugucuga    2580
ggggug                                                                2586
```

\<210\> SEQ ID NO 2
\<211\> LENGTH: 2583
\<212\> TYPE: RNA
\<213\> ORGANISM: Homo_Sapiens

\<400\> SEQUENCE: 2

```
gauuggggu uucccucccc augugcucaa gacuggcgcu aaaaguuuug agcuucucaa      60
aagucuagag ccaccgucca gggagcaggu agcugcuggg cuccgggac acuuugcguu    120 cgggcuggga gcgugcuuuc cacgacgugu acacgcuucc cuggauuggc cagacugccu    180
uccgggucac ugccauggag gagccgcagu cagauccuag cgucgagccc ccucgagu с    240 aggaaacauu uucagaccua uggaaacuac uuccugaaaa caacguucug uccccccuugc   300 cgucccaagc aauggaugau uugaugcugu ccccggacga uauugaacaa agguucacug    360
aagacccagg uccagaugaa gcuccagaa ugccagaggc ugcucccccc guggccccug     420
caccagcagc uccuacaccg gcggcccccug caccagcccc cuccuggccc cugucaucuu    480
cugucccuuc ccagaaaacc uaccagggca gcuacgguuu ccgucgggc uucuugcauu     540 cuggacagc caagucugug acuugcacgu acuccccugc ccucaacaag auguuuugcc    600
aacuggccaa gaccugcccu gugcagcugu gggugauuc cacacccccg cccggcaccc     660
gcguccgcgc cauggccauc uacaagcagu cacagcacau gacggaggu u gugaggcgcu   720 gcccccacca ugagcgcugc ucagauagcg auggucuggc cccuccucag caucuuaucc    780
gaguggaagg aaauuugcgu guggaguauu uggaugacag aaaacacuuuu cgacauagug    840 uggguggugcc cuaugagccg ccugagguug gcucucugacg uaccaccauc cacuacaacu   900
```

| | |
|---|---|
| acauguguaa caguccugc augggcggca ugaaccggag gcccauccuc accaucauca | 960 |
| cacuggaaga cuccaguggu aaucuacugg gacggaacag cuuugaggug cguguuugug | 1020 |
| ccuguccugg gagagaccgg cgcacagagg aagagaaucu ccgcaagaaa ggggagccuc | 1080 |
| accacgagcu gccccaggg agcacuaagc gagcacugcc caacaacacc agcuccucuc | 1140 |
| cccagccaaa gaagaaacca cuggauggag aauauuucac ccuucagauc cgugggcgug | 1200 |
| agcgcuucga gauguccga gagcugaaug aggccuugga acuaaggau gcccaggcug | 1260 |
| ggaaggagcc aggggggagc agggcucacu ccagccaccu gaaguccaaa aagggucagu | 1320 |
| cuaccucccg ccauaaaaaa cucauguuca agacagaagg gccugacuca gacugacauu | 1380 |
| cuccacuucu uguuccccac ugacagccuc ccaccccau cucucccccc ccugccauuu | 1440 |
| uggguuuugg gucuuugaac ccuugcuugc aauaggugug cgucagaagc acccaggacu | 1500 |
| uccauugcu uugucccggg gcccacuga acaaguuggc cugcacuggu guuuguugu | 1560 |
| ggggaggagg augggagua ggacauacca gcuuagauu uaagguuuuu acugugaggg | 1620 |
| auguuuggga gauguaagaa auguucugc aguuaagggu uaguuuacaa ucagccacau | 1680 |
| ucuaggagg ggcccacuuc accguacuaa ccagggaagc uguccccac uguugaauuu | 1740 |
| ucucuaacuu caaggcccau aucgugaaaa ugcuggcauu ugcaccuacc ucacagagug | 1800 |
| cauugugagg guuaaugaaa uaauguacau cuggccuuga aaccaccuuu uauuacaugg | 1860 |
| ggucuagaac uugacccccu ugagggugcu uguucccucu cccguuggu cggggguuu | 1920 |
| guaguuucua caguugggca gcugguuagg uagagggagu ugucaagucu cugcuggccc | 1980 |
| agccaaaccc cugucugacaa ccucuuggug aaccuuagua ccuaaaagga aaucucaccc | 2040 |
| caucccacac ccuggaggau uucaucucuu guauaugaug aucuggaucc accaagacuu | 2100 |
| guuuuaugcu cagggucaau ucuuuuuuc uuuuuuuuuu uuuuuuucu uuucuuuga | 2160 |
| gacugggucu cgcuuuguug cccaggcugg aguggagugg cgugaucuug gcuuacugca | 2220 |
| gccuuugccu ccccggcucg agcaguccug ccucagccuc cggaguagcu gggaccacag | 2280 |
| guucaugcca ccauggccag ccaacuuuug caguguuugu agagauggg ucucacagug | 2340 |
| uugcccaggc uggucucaaa cuccuggcu caggcgaucc accugucuca gcccuccaga | 2400 |
| gugcuggau uacaauugug agccaccacg uccagcugga agggucaaca ucuuuuacau | 2460 |
| ucugcaagca caucugcauu uucaccccac ccuuccccuc cuucccccuu uuuauauccc | 2520 |
| auuuuuauau cgaucucuua uuuuacaaua aaacuuugcu gccaccugug ugucugaggg | 2580 |
| gug | 2583 |

<210> SEQ ID NO 3
<211> LENGTH: 2719
<212> TYPE: RNA
<213> ORGANISM: Homo_Sapiens

<400> SEQUENCE: 3

| | |
|---|---|
| gauuggggu uuccccuccc augugcucaa gacuggcgcu aaaaguuuug agcuucucaa | 60 |
| aagucuagag ccaccgucca gggagcaggu agcugcuggg cuccggggac acuuugcguu | 120 |
| cgggcuggga gcgugcuuuc cacgacggug acacgcuucc cuggauuggc agccagacug | 180 |
| ccuuccgggu cacugccaug gaggagccgc agucagaucc uagcgucgag ccccucuga | 240 |
| gucaggaaac auuuucagac cuauggaaac uacuuccuga aaacaacguu cugucccccu | 300 |
| ugccgucccca agcaauggau gauuugaugc uguccccgga cgauauugaa caaugguuca | 360 |
| cugaagaccc aggucccagau gaagcuccca gaaugccaga ggcugcuccc cccgugcccc | 420 |

-continued

```
cugcaccagc agcuccuaca ccggcggccc cugcaccagc ccccuccugg ccccugucau      480 cuucugucccc uucccagaaa accuaccagg gcagcuacgg uuccgucug ggcuucuugc      540 auucugggac agccaagucu gugacuugca cguacccccc ugcccucaac aagauguuuu      600
gccaacuggc caagaccugc ccugugcagc ugugggsuuga uuccacaccc cgcccggca     660 cccgcguccg cgccauggcc aucuacaagc agucacagca caugacggag guugugaggc     720
gcugccccca ccaugagcgc ugcucagaua gcgauggucu ggccccuccu cagcaucuua     780
uccgagugga aggaaauuug cguguggagu auuuggauga cagaaacacu uuucgacaua     840
gugugguggu gcccuaugag ccgccugagg uggcucuga cuuaccacc auccacuaca     900 acuacaugug uaacaguucc ugcaugggcg gcaugaaccg gaggcccauc cucaccauca     960
ucacacugga gacuccagu gguaaucuac ugggacggaa cagcuuugag gugcguguuu    1020
gugccugucc ugggagagac cggcgcacag aggaagagaa ucccgcaag aaagggagc    1080 cucaccacga gcugccccca gggagcacua agcgagcacu gcccaacaac accagcuccu    1140
cuccccagcc aaagaagaaa ccacuggaug gagaauauuu cacccuucag gaccagacca    1200
gcuuucaaaa agaaaauugu uaaagagagc augaaaaugg uucuaugacu ugccugaua    1260 cagaugcuac uugacuuacg augguguuac uuccugauaa acucgcguua aguugaaaau    1320
auuauccgug ggcgugagcg cuucgagaug uccgagagc ugaaugaggc cuggaacuc    1380 aaggaugccc aggcugggaa ggagccaggg gggagcaggg cucacuccag ccaccugaag    1440
uccaaaaagg gucagucuac cucccgccau aaaaaacuca uguucaagac agaagggccu    1500
gacucagacu gacauucucc acuucuuguu ccccacugac agccucccac ccccaucucu    1560
cccuccccug ccauuuuggg uuuugggucu uugaacccuu gcuugcaaua ggugugcguc    1620
agaagcaccc aggacuucca uuugcuuugu cccggggcuc cacugaacaa guuggccugc    1680
acugguguuu uguugugggg aggaggauggg ggaguaggac auaccagcuu agauuuuaag    1740
guuuuuacug ugagggaugu uugggagaug uaagaaaugu ucuugcaguu aagggguagu    1800
uuacaaucag ccacauucua gguaggggcc cacuucaccg uacuaaccag ggaagcuguc    1860
ccucacuguu gaauuuucuc uaacuucaag gcccauaucu gugaaaugcu ggcauuugca    1920
ccuaccucac agagugcauu gugagggguua augaaauaau guacaucugg ccuugaaacc    1980
accuuuuauu acauggggcu uagaacuuga cccccuugag ggugcuuguu cccucucccu    2040
guuggucggu ggguugguag uuucuacagu ugggcagcug guuagguaga gggaguuguc    2100
aagucucugc uggcccagcc aaacccuguc ugacaaccuc uuggugaacc uuaguaccua    2160
aaaggaaauc ucaccccauc ccacacccug gaggauuuca ucucuuguau augaugaucu    2220
ggauccacca agacuuguuu uaugcucagg gucaauuucu uuuucuuuu uuuuuuuuu    2280 uuuucuuuuu cuugagacu gggucucgcu uguugccca ggcuggagug gagugcgug    2340 aucuggcuu acugcagccu uugccucccc ggcucgagca guccgccuc agccuccgga    2400 guagcuggga ccacagguuc augccaccau ggccagccaa cuuuugcaug uuuuguagag    2460
auggggucuc acaguuugc ccaggcuggu cucaaacucc ugggcucagg cgauccaccu    2520
gucucagccu cccagagugc ugggauuaca auugugagcc accgucca gcuggaaggg    2580 ucaacaucuu uuacauucug caagcacauc ugcauuuuca ccccacccuu cccuccuuc    2640 ucccuuuuua uauccccauuu uuauaucgau cucuuauuuu acaauaaaac uuugcugcca    2700 ccugugugucc ugaggggug                                                 2719
```

<210> SEQ ID NO 4
<211> LENGTH: 2646
<212> TYPE: RNA
<213> ORGANISM: Homo_Sapiens

<400> SEQUENCE: 4

| | | | | | |
|---|---|---|---|---|---|
| gauuggggu | uucccucccc | augugcucaa | gacuggcgcu | aaaaguuuug | agcuucucaa | 60 |
| aagucuagag | ccaccgucca | gggagcaggu | agcugcuggg | ucccgggac | acuuugcguu | 120 |
| cgggcuggga | gcgugcuuuc | cacgacggug | acacgcuucc | cuggauuggc | agccagacug | 180 |
| ccuuccgggu | cacugccaug | gaggagccgc | agucagaucc | uagcgucgag | cccccucuga | 240 |
| gucaggaaac | auuuucagac | cuauggaaac | uacuuccuga | aaacaacguu | cugucccccu | 300 |
| ugccgucca | agcaauggau | gauuugaugc | ugucccgga | cgauauugaa | caugguuca | 360 |
| cugaagaccc | agguccagau | gaagcuccca | gaaugccaga | ggcugcuccc | ccgguggccc | 420 |
| cugcaccagc | agcccuaca | ccggcggccc | cugcaccagc | ccccuccugg | cccugucau | 480 |
| cuucugucc | uucccagaaa | accuaccagg | gcagcuacgg | uuccgucug | ggcuucuugc | 540 |
| auucugggac | agccaagucu | ugacacugca | cguaccccc | ugcccucaac | aagauguuu | 600 |
| gccaacuggc | caagaccugc | ccugugcagc | ugugggua | uccacaccc | ccgcccggca | 660 |
| cccgcguccg | cgccauggcc | aucuacaagc | agucacagca | caugacggag | guugugaggc | 720 |
| gcugccccca | ccaugagcgc | ugcucagaua | gcgauggucu | ggccccuccu | cagcaucuua | 780 |
| uccgagugga | aggaaauuug | cgugugagu | auuuggauga | cagaaacacu | uucgacaua | 840 |
| guguggugu | gcccuaugag | ccgccugagg | uuggcucuga | cuuaccacc | auccacuaca | 900 |
| acuacaugug | uaacaguucc | ugcaugggcg | gcaugaaccg | gaggcccauc | cucaccauca | 960 |
| ucacacugga | agacuccagu | gguaaucuac | ugggacggaa | cagcuuugag | gugcguguuu | 1020 |
| gugccugucc | ugggagagac | cggcgcacag | aggaagagaa | ucuccgcaag | aaaggggagc | 1080 |
| cucaccacga | gcugccccca | gggagcacua | agcgagcacu | gcccaacaac | accagcuccu | 1140 |
| cuccccagcc | aaagaagaaa | ccacuggaug | gagaauauuu | cacccuucag | augcuacuug | 1200 |
| acuuacgaug | uguuacuuc | cugauaaacu | cgucguaagu | ugaaaauauu | auccgugggc | 1260 |
| gugagcgcuu | cgagauguuc | cgagagcuga | augaggccuu | ggaacucaag | gaugcccagg | 1320 |
| cuggaaggaa | gccaggggg | agcagggcuc | acuccagcca | ccugaagucc | aaaaagggguc | 1380 |
| agucuaccuc | ccgccauaaa | aaacucaugu | ucaagacaga | agggccugac | ucagacugac | 1440 |
| auucuccacu | ucuuguccc | cacugacagc | cucccaccc | caucucccc | ucccugcca | 1500 |
| uuuuggguuu | uggguucuuug | aacccuugcu | ugcaauaggu | gugcgucaga | agcacccagg | 1560 |
| acuuccauuu | gcuuugucc | ggggucccac | ugaacaaguu | ggccugcacu | gguguuuugu | 1620 |
| uguggggagg | aggauggga | guaggacaua | ccagcuuaga | uuuuaagguu | uuuacuguga | 1680 |
| gggauguuug | ggagauguaa | gaaauguucu | ugcaguuaag | gguuaguuua | caaucagcca | 1740 |
| cauucuaggu | agggggccccac | uucaccguac | uaaccaggga | agcugucccu | cacuguuaa | 1800 |
| uuuucucuaa | cuucaaggcc | cauaucugug | aaaugcuggc | auuugcaccu | accucacaga | 1860 |
| gugcauugug | aggguuaaug | aaauaaugua | caucuggccu | ugaaaccacc | uuuuauuaca | 1920 |
| uggggucuag | aacuugaccc | ccuugagggu | gcuuguuccc | ucucccuguu | ggucgguggg | 1980 |
| uugguaguuu | cuacaguugg | gcagcugguu | agguagaggg | aguugucaag | ucucugcugg | 2040 |
| cccagccaaa | cccugucuga | caaccucuug | gugaaccuua | guaccuaaaa | ggaaaucuca | 2100 |
| ccccauccca | cacccuggag | gauuucaucu | cuuguauaug | augaucugga | uccaccaaga | 2160 |

| | | |
|---|---|---|
| cuuguuuuau gcucaggguc aauuucuuuu uucuuuuuuu uuuuuuuuuu ucuuuuucuu | 2220 | |
| ugagacuggg ucucgcuuug uugcccaggc uggaguggag uggcgugauc uuggcuuacu | 2280 | |
| gcagccuuug ccuccccggc ucgagcaguc cugccucagc cuccggagua gcugggacca | 2340 | |
| cagguucaug ccaccauggc agccaacauu ugcauguuu uguagagaug ggucucaca | 2400 | |
| guguugccca ggcuggucuc aaacuccugg gcucaggcga uccaccuguc ucagccuccc | 2460 | |
| agagugcugg gauuacaauu gugagccacc acguccagcu ggaagggauca acaucuuuua | 2520 | |
| cauucugcaa gcacaucugc auuucacccc cacccuuccc cuccuucucc cuuuuuauau | 2580 | |
| cccauuuuua uaucgaucuc uuauuuuaca auaaaacuuu gcugccaccu gugugucuga | 2640 | |
| gggggug | 2646 | |

<210> SEQ ID NO 5
<211> LENGTH: 2271
<212> TYPE: RNA
<213> ORGANISM: Homo_Sapiens

<400> SEQUENCE: 5

| | | |
|---|---|---|
| ugaggccagg agauggaggc ugcagugagc ugugaucaca ccacugugcu ccagccugag | 60 | |
| ugacagagca agacccuauc ucaaaaaaaa aaaaaaaaa gaaaagcucc ugagguguag | 120 | |
| acgccaacuc ucucuagcuc gcuaguggu ugcaggaggu gcuuacgcau guuuguuucu | 180 | |
| uugcugccgu cuuccaguug cuuuaucugu ucacuugugc ccgacuuuc aacucugucu | 240 | |
| ccuuccucuu ccuacaguac uccccugccc ucaacaagau guuuugccaa cuggccaaga | 300 | |
| ccugcccugu gcagcugugg guugauucca caccccgcc cggcacccgc guccgcgcca | 360 | |
| uggccaucua caagcaguca cagcacauga cggagguugu gaggcgcugc ccccaccaug | 420 | |
| agcgcugcuc agauagcgau ggucuggccc cuccucagca ucuuauccga guggaaggaa | 480 | |
| auuugcugugu ggaguauuug gaugacagaa acacuuuucg acauagugug ugggugcccu | 540 | |
| augagccgcc ugagguuggc ucugacugua ccaccaucca cuacaacuac augguguaaca | 600 | |
| guuccugcau gggcggcaug aaccggaggc ccauccucac caucaucaca cuggaagacu | 660 | |
| ccagugguaa ucuacuggga cggaacagcu uugaggugcg uguuugugcc uguccuggga | 720 | |
| gagaccggcg cacagaggaa gagaaucucc gcaagaaagg ggagccucac cacgagcugc | 780 | |
| ccccagggag cacuaagcga gcacugccca acaacaccag cuccucuccc cagccaaaga | 840 | |
| agaaaccacu ggauggagaa uauucacccc uucagauccg ugggcgugag cgcuucgaga | 900 | |
| uguccgaga gcugaaugag gccuuggaac ucaaggaugc ccaggcuggg aaggagccag | 960 | |
| ggggggagcag ggcucacucc agccaccuga aguccaaaaa gggucaguc accucccgcc | 1020 | |
| auaaaaaacu cauguucaag acagaagggc cugacacaga cugacauucu ccacuucuug | 1080 | |
| uuccccacug acagccuccc accccaucu cuccucuccc ugccauuuug gguuuggguu | 1140 | |
| cuuugaaccc uugcuugcaa uaggugugcg ucagaagcac ccaggacuuc cauuugcuuu | 1200 | |
| guccggggc uccacugaac aaguuggccu gcacuggugu uuguugugg ggaggaggau | 1260 | |
| gggagauagg acauaccagc uuagauuuua agguuuuuac ugugagggau guuugggaga | 1320 | |
| uguaagaaau guucuugcag uuaaggguua guuacaauc agccacauuc uaggaugggg | 1380 | |
| cccacuucac cguacuaacc agggaagcug ucccucacug uugaauuuuc ucaacuuca | 1440 | |
| aggcccauau cugugaaaug cuggcauuug caccuaccuc acagagugca uugugagggu | 1500 | |
| uaaugaaaua auguacaucu ggccuugaaa ccaccuuuua uuacaugggg ucuagaaacuu | 1560 | |

| | |
|---|---|
| gaccccccuug agggugcuug uucccucucc cuguuggucg gugggguuggu aguuucuaca | 1620 |
| guugggcagc ugguuaggua gagggaguug ucaagucucu gcuggcccag ccaaacccug | 1680 |
| ucugacaacc ucuuggugaa ccuuaguacc uaaaaggaaa ucucacccca ucccacaccc | 1740 |
| uggaggauuu caucucuugu auaugaugau cuggauccac caagacuugu uuuaugcuca | 1800 |
| gggucaauuu cuuuuuucuu uuuuuuuuu uuuuucuuu uucuuugaga cugggucucg | 1860 |
| cuuuguugcc caggcuggag uggaguggcg ugaucuuggc uuacgcagc cuuuccucc | 1920 |
| ccggcucgag caguccugcc ucagccuccg gaguagcugg gaccacaggu caugccacc | 1980 |
| auggccagcc aacuuuugca uguuuugaug agaugggguc ucacagguguu gcccaggcug | 2040 |
| gucucaaacu ccugggcuca ggcgauccac cugucucagc cucccagagu gcugggauua | 2100 |
| caauugugag ccaccacguc cagcuggaag ggucaacauc uuuuacauuc ugcaagcaca | 2160 |
| ucugcauuuu caccccaccc uuccccuccu ucucccuuuu uauauccccau uuuuauaucg | 2220 |
| aucucuuauu uuacaauaaa acuuugcugc caccugugug ucugaggggu g | 2271 |

<210> SEQ ID NO 6
<211> LENGTH: 2404
<212> TYPE: RNA
<213> ORGANISM: Homo_Sapiens

<400> SEQUENCE: 6

| | |
|---|---|
| ugaggccagg agauggaggc ugcagugagc ugugaucaca ccacugugcu ccagccugag | 60 |
| ugacagagca agacccuauc ucaaaaaaaa aaaaaaaaa gaaaagcucc ugagguguag | 120 |
| acgccaacuc ucucuagcuc gcuaguggu ugcaggaggu gcuuacgcau guuuguuucu | 180 |
| uugcugccgu cuuccaguug cuuuaucugu ucacuugugc ccugacuuuc aacucugucu | 240 |
| ccuuccucuu ccuacaguac uccccugccc ucaacaagau guuuugccaa cuggccaaga | 300 |
| ccugcccugu gcagcugugg guugauucca caccccgcc cggcacccgc gucgcgcca | 360 |
| uggccaucua caagcaguca cagcacauga cggagguugu gaggcgcugc ccccaccaug | 420 |
| agcgcugcuc agauagcgau ggucuggccc cuccucagca ucuuauccga guggaaggaa | 480 |
| auuugcgugu ggaguauuug gaugacagaa acacuuuucg acauagugug gugguugcccu | 540 |
| augagccgcc ugagguuggc ucugacugua ccaccaucca cuacaacuac auguguaaca | 600 |
| guuccugcau gggcggcaug aaccggaggc ccauccucac caucaucaca cuggaagacu | 660 |
| ccaggguaa ucuacuggga cggaacagcu uugaggugcg uguuugugcc uguccuggga | 720 |
| gagaccggcg cacagaggaa gagaaucucc gcaagaaagg ggagcccuac cacgagcugc | 780 |
| ccccagggag cacuaagcga gcacugccca acaacaccag cuccucuccc cagccaaaga | 840 |
| agaaaccacu ggauggagaa uauuucaccc uucaggacca gaccagcuuu caaaagaaa | 900 |
| auuguuaaag agagcaugaa aaugguucua ugacuuugcc ugauacagau gcuacuugac | 960 |
| uuacgauggu guuacuuccu gauaaacucg ucgaaguug aaaauauuau ccguggggcgu | 1020 |
| gagcgcuucg agauguuccg agagcugaau gaggccuugg aacucaagga ugcccaggcu | 1080 |
| gggaaggagc cagggggggag cagggcucac uccagccacc ugaaguccaa aaagggucag | 1140 |
| ucuaccuccc gccauaaaaa acucauguuc aagacagaag ggccgacuc agacugacau | 1200 |
| ucuccacuuc uuguucccca cugacagccu cccaccccca ucucucccuc ccugccauu | 1260 |
| uugggguuuu ggucuuugaa cccuugccuug caauagugu gcgucagaag cacccaggac | 1320 |
| uuccauuugc uuugucccgg ggcuccacug aacaaguugg ccugcacugg guuuugguug | 1380 |
| uggggaggag gauggggagu aggacauacc agcuuagauu uuaagguuuu uacugugagg | 1440 |

-continued

| | |
|---|---|
| gauguuuggg agauguaaga aauguucuug caguuaaggg uuaguuuaca aucagccaca | 1500 |
| uucuagguag gggcccacuu caccguacua accagggaag cuguccccuca cuguugaauu | 1560 |
| uucucuaacu ucaaggccca uaucugugaa augcuggcau uugcaccuac cucacagagu | 1620 |
| gcauugugag gguuaaugaa auaauguaca ucuggccuug aaaccaccuu uauuacaug | 1680 |
| gggucuagaa cuugacccccc uugagggugc uguuccccuc ucccguuggg ucgguggguu | 1740 |
| gguaguuucu acaguugggc agcugguuag guagagggag uugucaaguc ucugcuggcc | 1800 |
| cagccaaacc cugucugaca accucuuggu gaaccuuagu accuaaaagg aaaucucacc | 1860 |
| ccaucccaca cccuggagga uuucaucucu uguauaugau gaucuggauc caccaagacu | 1920 |
| uguuuuaugc ucagggucaa uucuuuuuu cuuuuuuuu uuuuuuuuc uuuucuuug | 1980 |
| agacuggguc ucgcuuuguu gcccaggcug gaguggagug gcgugaucuu ggcuuacugc | 2040 |
| agccuuugcc uccccggcuc gagcagaccu gccucagccu ccggaguagc ugggaccaca | 2100 |
| gguucaugcc accauggcca gccaacuuuu gcauguuuu uagagauggg gucucacagu | 2160 |
| guugcccagg cuggucucaa acuccugggc ucaggcgauc caccugucuc agccucccag | 2220 |
| agucugggga uuacaauugu gagccaccac guccagcugg aagggucaac aucuuuuaca | 2280 |
| uucugcaagc acaucugcau uuucaccccca cccuucccccu ccuucccccu uuuuauaucc | 2340 |
| cauuuuaua ucgaucucuu auuuuacaau aaaacuuugc ugccaccgu gugucugagg | 2400 |
| ggug | 2404 |

<210> SEQ ID NO 7
<211> LENGTH: 2331
<212> TYPE: RNA
<213> ORGANISM: Homo_Sapiens

<400> SEQUENCE: 7

| | |
|---|---|
| ugaggccagg agauggaggc ugcagugagc ugugaucaca ccacugugcu ccagccugag | 60 |
| ugacagagca agacccuauc ucaaaaaaaa aaaaaaaaa gaaaagcucc ugagguguag | 120 |
| acgccaacuc ucucuagcuc gcuaguggu ugcaggaggu gcuuacgcau guuuguuucu | 180 |
| uugcugccgu cuuccaguug cuuuaucugu ucacuugugc ccugacuuuc aacucugucu | 240 |
| ccuuccucuu ccuacaguac uccccugccc ucaacaagau guuuugccaa cuggccaaga | 300 |
| ccugcccugu gcagcugugg guugauucca caccccccgcc cggcacccgc guccgcgcca | 360 |
| uggccaucua caagcaguca cagcacauga cggagguugu gaggcgcugc ccccaccaug | 420 |
| agcgcugcuc agauagcgau ggucuggccc cuccucagca ucuuauccga guggaaggaa | 480 |
| auuugcgugu ggaguauuug gaugacagaa acacuuuucg acauagugug guggugcccu | 540 |
| augagccgcc ugagguugc ucugacugua ccaccaucca cuacaacuac auguguaaca | 600 |
| guuccugcau gggcggcaug aaccggaggc ccauccucac caucaucaca cuggaagacu | 660 |
| ccagugguaa ucuacuggga cggaacagcu uugaggugcg uguuugugcc uguccuggga | 720 |
| gagaccggcg cacagaggaa gagaaucucc gcaagaaagg ggagccucac cacgagcugc | 780 |
| ccccagggag cacuaagcga gcacugccca caacaccag cuccucuccc cagccaaaga | 840 |
| agaaaccacu ggauggagaa uauuucaccc uucagaugcu acuugacuua cgauggugu | 900 |
| acuuccugau aaacucgucg uaaguugaaa auauuauccg ugggcgugag cgcuucgaga | 960 |
| uguuccgaga gcugaaugag gccuggaac ucaaggaugc ccaggcuggg aaggagccag | 1020 |
| gggggagcag ggcucacucc agccaccuga agucaaaaaa gggucagucu accucccgcc | 1080 |

```
auaaaaaacu cauguucaag acagaagggc cugacucaga cugacauucu ccacuucuug    1140
uuccccacug acagccuccc accccccaucu cucccuccccc ugccauuuug gguuuuggggu    1200
```

```
auaaaaaacu cauguucaag acagaagggc cugacucaga cugacauucu ccacuucuug    1140
uuccccacug acagccuccc accccccaucu cucccucccc ugccauuuug gguuuugggu    1200
cuuugaaccc uugcuugcaa uaggugugcg ucagaagcac ccaggacuuc cauuugcuuu    1260
gucccgggc uccacugaac aaguuggccu gcacuggugu uuuguuguuugugg ggaggaggau    1320
ggggaguagg acauaccagc uuagauuuua agguuuuac ugugagggau guuugggaga    1380
uguaagaaau guucuugcag uuaagggua guuuacaauc agccacauuc uaggaugggg    1440
cccacuucac cguacuaacc agggaagcug ucccucacug uugaauuuuc ucaacuuca    1500
aggcccauau cugugaaaug cuggcauuug caccuaccuc acagagugca uugugagggu    1560
uaaugaaaua auguacaucu ggccuugaaa ccaccuuuua uuacauggggg ucuagaacuu    1620
gaccccuug agggugcuug uucccucucc cguuggucg gugggguuggu aguuucuaca    1680
guuggggcagc ugguuaggua gagggaguug ucaagucucu gcuggccag ccaaacccug    1740
ucugacaacc ucuuggugaa ccuuaguacc uaaaaggaaa ucucaccccu ucccacaccc    1800
uggaggauuu caucucuugu auaugaugau cuggauccac caagacugu uuuaugcuca    1860
gggucaauuu cuuuuucuu uuuuuuuu uuuucuuu ucuuugaga cugggucucg    1920
cuuuguugcc caggcuggag uggaguggcg ugaucuuggc uuacgcagc cuuugccucc    1980
ccggcucgag cagccugcc ucagccuccg gaguagcugg gaccacaggu ucaugccacc    2040
auggccagcc aacuuuugca uguuuuguag agauggggguc ucacaguguu gcccaggcug    2100
gucucaaacu ccugggcuca ggcgauccac cugucucagc cucccagagu gcuggauua    2160
caauugugag ccaccacguc cagcuggaag ggucaacauc uuuuacauuc ugcaagcaca    2220
ucugcauuuu caccccaccc uucccccuccu ucucccuuuu uauaucccau uuuuauaucg    2280
aucucuuauu uuacaauaaa acuuugcugc caccugugug ucugaggggu g              2331
```

<210> SEQ ID NO 8
<211> LENGTH: 19
<212> TYPE: RNA
<213> ORGANISM: artificial
<220> FEATURE:
<223> OTHER INFORMATION: Chemically Synthesized

<400> SEQUENCE: 8
cagaccuaug gaaacuacu                                                19

<210> SEQ ID NO 9
<211> LENGTH: 19
<212> TYPE: RNA
<213> ORGANISM: artificial
<220> FEATURE:
<223> OTHER INFORMATION: Chemically Synthesized

<400> SEQUENCE: 9
ggauguuugg gagauguaa                                                19

<210> SEQ ID NO 10
<211> LENGTH: 19
<212> TYPE: RNA
<213> ORGANISM: artificial
<220> FEATURE:
<223> OTHER INFORMATION: Chemically Synthesized

<400> SEQUENCE: 10
gacucagacu gacauucua                                                19

```
<210> SEQ ID NO 11
<211> LENGTH: 19
<212> TYPE: RNA
<213> ORGANISM: artificial
<220> FEATURE:
<223> OTHER INFORMATION: Chemically Synthesized

<400> SEQUENCE: 11
ggguugguag uuucuacaa                                               19

<210> SEQ ID NO 12
<211> LENGTH: 19
<212> TYPE: RNA
<213> ORGANISM: artificial
<220> FEATURE:
<223> OTHER INFORMATION: Chemically Synthesized

<400> SEQUENCE: 12
gggauguuug ggagaugua                                               19

<210> SEQ ID NO 13
<211> LENGTH: 19
<212> TYPE: RNA
<213> ORGANISM: artificial
<220> FEATURE:
<223> OTHER INFORMATION: Chemically Synthesized

<400> SEQUENCE: 13
ggauccacca agacuugua                                               19

<210> SEQ ID NO 14
<211> LENGTH: 19
<212> TYPE: RNA
<213> ORGANISM: artificial
<220> FEATURE:
<223> OTHER INFORMATION: Chemically Synthesized

<400> SEQUENCE: 14
gagggauguu ugggagaua                                               19

<210> SEQ ID NO 15
<211> LENGTH: 19
<212> TYPE: RNA
<213> ORGANISM: artificial
<220> FEATURE:
<223> OTHER INFORMATION: Chemically Synthesized

<400> SEQUENCE: 15
gggccugacu cagacugaa                                               19

<210> SEQ ID NO 16
<211> LENGTH: 19
<212> TYPE: RNA
<213> ORGANISM: artificial
<220> FEATURE:
<223> OTHER INFORMATION: Chemically Synthesized

<400> SEQUENCE: 16
gacucagacu gacauucuu                                               19

<210> SEQ ID NO 17
<211> LENGTH: 19
<212> TYPE: RNA
<213> ORGANISM: artificial
<220> FEATURE:
<223> OTHER INFORMATION: Chemically Synthesized
```

<400> SEQUENCE: 17
gcauuugcac cuaccucaa                                                19

<210> SEQ ID NO 18
<211> LENGTH: 19
<212> TYPE: RNA
<213> ORGANISM: artificial
<220> FEATURE:
<223> OTHER INFORMATION: Chemically Synthesized

<400> SEQUENCE: 18
ggauguuugg gagauguau                                                19

<210> SEQ ID NO 19
<211> LENGTH: 19
<212> TYPE: RNA
<213> ORGANISM: artificial
<220> FEATURE:
<223> OTHER INFORMATION: Chemically Synthesized

<400> SEQUENCE: 19
gggccugacu cagacugau                                                19

<210> SEQ ID NO 20
<211> LENGTH: 19
<212> TYPE: RNA
<213> ORGANISM: artificial
<220> FEATURE:
<223> OTHER INFORMATION: Chemically Synthesized

<400> SEQUENCE: 20
cagaccuaug gaaacuaca                                                19

<210> SEQ ID NO 21
<211> LENGTH: 19
<212> TYPE: RNA
<213> ORGANISM: artificial
<220> FEATURE:
<223> OTHER INFORMATION: Chemically Synthesized

<400> SEQUENCE: 21
aguaguuucc auaggucug                                                19

<210> SEQ ID NO 22
<211> LENGTH: 19
<212> TYPE: RNA
<213> ORGANISM: artificial
<220> FEATURE:
<223> OTHER INFORMATION: Chemically Synthesized

<400> SEQUENCE: 22
uuacaucucc caaacaucc                                                19

<210> SEQ ID NO 23
<211> LENGTH: 19
<212> TYPE: RNA
<213> ORGANISM: artificial
<220> FEATURE:
<223> OTHER INFORMATION: Chemically Synthesized

<400> SEQUENCE: 23
uagaauguca gucugaguc                                                19

<210> SEQ ID NO 24
<211> LENGTH: 19

```
<212> TYPE: RNA
<213> ORGANISM: artificial
<220> FEATURE:
<223> OTHER INFORMATION: Chemically Synthesized

<400> SEQUENCE: 24
uuguagaaac uaccaaccc                                                      19

<210> SEQ ID NO 25
<211> LENGTH: 19
<212> TYPE: RNA
<213> ORGANISM: artificial
<220> FEATURE:
<223> OTHER INFORMATION: Chemically Synthesized

<400> SEQUENCE: 25
uacaucuccc aaacauccc                                                      19

<210> SEQ ID NO 26
<211> LENGTH: 19
<212> TYPE: RNA
<213> ORGANISM: artificial
<220> FEATURE:
<223> OTHER INFORMATION: Chemically Synthesized

<400> SEQUENCE: 26
uacaagucuu gguggaucc                                                      19

<210> SEQ ID NO 27
<211> LENGTH: 19
<212> TYPE: RNA
<213> ORGANISM: artificial
<220> FEATURE:
<223> OTHER INFORMATION: Chemically Synthesized

<400> SEQUENCE: 27
uaucucccaa acaucccuc                                                      19

<210> SEQ ID NO 28
<211> LENGTH: 19
<212> TYPE: RNA
<213> ORGANISM: artificial
<220> FEATURE:
<223> OTHER INFORMATION: Chemically Synthesized

<400> SEQUENCE: 28
uucagucuga gucaggccc                                                      19

<210> SEQ ID NO 29
<211> LENGTH: 19
<212> TYPE: RNA
<213> ORGANISM: artificial
<220> FEATURE:
<223> OTHER INFORMATION: Chemically Synthesized

<400> SEQUENCE: 29
aagaauguca gucugaguc                                                      19

<210> SEQ ID NO 30
<211> LENGTH: 19
<212> TYPE: RNA
<213> ORGANISM: artificial
<220> FEATURE:
<223> OTHER INFORMATION: Chemically Synthesized

<400> SEQUENCE: 30
```

```
uugagguagg ugcaaaugc                                                19

<210> SEQ ID NO 31
<211> LENGTH: 19
<212> TYPE: RNA
<213> ORGANISM: artificial
<220> FEATURE:
<223> OTHER INFORMATION: Chemically Synthesized

<400> SEQUENCE: 31
auacaucucc caaacaucc                                                19

<210> SEQ ID NO 32
<211> LENGTH: 19
<212> TYPE: RNA
<213> ORGANISM: artificial
<220> FEATURE:
<223> OTHER INFORMATION: Chemically Synthesized

<400> SEQUENCE: 32
aucagucuga gucaggccc                                                19

<210> SEQ ID NO 33
<211> LENGTH: 19
<212> TYPE: RNA
<213> ORGANISM: Artificial Sequence
<220> FEATURE:
<223> OTHER INFORMATION: Chemically Synthesized

<400> SEQUENCE: 33
uguaguuucc auaggucug                                                19
```